(12) United States Patent
Mortarino

(10) Patent No.: US 9,204,953 B2
(45) Date of Patent: Dec. 8, 2015

(54) BIOCOMPATIBLE SURGICAL SCAFFOLD WITH VARYING STRETCH

(75) Inventor: Enrico Mortarino, Hickory, NC (US)

(73) Assignee: Allergan, Inc., Irvine, CA (US)

( * ) Notice: Subject to any disclaimer, the term of this patent is extended or adjusted under 35 U.S.C. 154(b) by 340 days.

(21) Appl. No.: 13/088,833

(22) Filed: Apr. 18, 2011

(65) Prior Publication Data

US 2011/0257761 A1  Oct. 20, 2011

Related U.S. Application Data

(63) Continuation-in-part of application No. 12/680,404, filed as application No. PCT/US2009/063717 on Nov. 9, 2009.

(60) Provisional application No. 61/122,520, filed on Dec. 15, 2008.

(51) Int. Cl.

| A61F 2/00 | (2006.01) |
|---|---|
| A61F 2/12 | (2006.01) |
| A61L 27/36 | (2006.01) |
| D04B 1/22 | (2006.01) |
| D04B 21/12 | (2006.01) |

(52) U.S. Cl.
CPC ............. *A61F 2/0063* (2013.01); *A61F 2/12* (2013.01); *A61L 27/3604* (2013.01); *D04B 1/22* (2013.01); *D04B 21/12* (2013.01); *A61F 2002/0068* (2013.01); *A61F 2250/0017* (2013.01); *D10B 2509/08* (2013.01)

(58) Field of Classification Search
CPC .......... A61F 2/0063; A61F 2/12; A61F 2/90; D04B 1/22; A04B 21/00; A04B 21/12; A04B 21/14; A04B 21/145; A04B 21/16; A04B 21/165; A04B 21/18; A04B 21/08
USPC ........ 606/151; 623/23.72, 23.74; 66/191–195
See application file for complete search history.

(56) References Cited

U.S. PATENT DOCUMENTS

| 848,605 | A |   | 3/1907 | Schmic |
|---|---|---|---|---|
| 955,541 | A | * | 4/1910 | Petersen .................... 139/387 R |
| 1,300,696 | A | * | 4/1919 | Branson .......................... 66/193 |

(Continued)

FOREIGN PATENT DOCUMENTS

| DE | 3917174 | 12/1990 |
|---|---|---|
| DE | 19928635 | 10/2000 |

(Continued)

OTHER PUBLICATIONS

Altman et al., Silk based biomaterials, *Biomaterials* (2003) 24:401-416.

(Continued)

*Primary Examiner* — Dianne Dornbusch
(74) *Attorney, Agent, or Firm* — Linda Allyson Nassif

(57) ABSTRACT

A biocompatible surgical scaffold made from a multi-filament silk yarn for soft tissue reconstruction. The scaffold incorporates regions of varying stretch having different physical and mechanical properties that allow contouring to the required soft tissue shape to be replaced or repaired. The porous structure allows tissue in-growth, while the mesh degrades at a rate which allows for a smooth transfer of mechanical properties to the new tissue from the silk scaffold.

10 Claims, 67 Drawing Sheets

(56) References Cited

U.S. PATENT DOCUMENTS

| | | | |
|---|---|---|---|
| 1,709,662 A | 4/1929 | Ellis | |
| 1,815,279 A | 7/1931 | Takamine, Jr | |
| 1,828,736 A | 10/1931 | Harvey, Jr. | |
| 1,896,494 A | 2/1933 | Myers et al. | |
| 1,921,022 A | 9/1933 | Fink et al. | |
| 1,990,588 A | 2/1935 | Bueno | |
| 2,040,949 A | 5/1936 | Olpin et al. | |
| 3,314,123 A * | 4/1967 | Groebli | 28/165 |
| 3,552,154 A * | 1/1971 | Lesley | 66/192 |
| 3,595,276 A | 7/1971 | Wrzesieo | |
| 3,672,187 A * | 6/1972 | Simpson | 66/192 |
| 3,922,888 A * | 12/1975 | Patterson | 66/192 |
| 3,931,721 A * | 1/1976 | Adamson | 66/195 |
| 3,952,555 A * | 4/1976 | Lesley | 66/195 |
| 3,999,407 A * | 12/1976 | Odham | 66/193 |
| 4,089,071 A * | 5/1978 | Kalnberz et al. | 623/23.61 |
| 4,118,842 A | 10/1978 | Norris et al. | |
| 4,141,207 A | 2/1979 | Mizushima et al. | |
| 4,248,064 A * | 2/1981 | Odham | 66/192 |
| 4,340,091 A * | 7/1982 | Skelton et al. | 139/383 R |
| 4,388,364 A * | 6/1983 | Sanders | 442/313 |
| 4,518,640 A * | 5/1985 | Wilkens | 428/102 |
| 4,530,113 A * | 7/1985 | Matterson | 623/1.51 |
| 4,792,336 A | 12/1988 | Hlavacek et al. | |
| 4,816,028 A * | 3/1989 | Kapadia et al. | 623/1.52 |
| 4,942,875 A | 7/1990 | Hlavacek et al. | |
| 4,984,570 A * | 1/1991 | Langen et al. | 602/44 |
| 5,120,829 A | 6/1992 | Pierschbacher et al. | |
| 5,134,006 A * | 7/1992 | Irvin | 428/68 |
| 5,171,505 A | 12/1992 | Lock | |
| 5,178,630 A * | 1/1993 | Schmitt | 623/1.52 |
| 5,191,777 A * | 3/1993 | Schnegg | 66/195 |
| 5,250,077 A | 10/1993 | Fuse et al. | |
| 5,252,285 A | 10/1993 | Lock | |
| 5,366,504 A * | 11/1994 | Andersen et al. | 623/1.5 |
| 5,385,836 A | 1/1995 | Kimura et al. | |
| 5,456,697 A | 10/1995 | Chesterfield et al. | |
| 5,490,602 A * | 2/1996 | Wilson et al. | 216/56 |
| 5,509,931 A * | 4/1996 | Schmitt | 623/1.52 |
| 5,569,273 A | 10/1996 | Titone et al. | |
| 5,587,456 A | 12/1996 | Pierschbacher et al. | |
| 5,591,822 A | 1/1997 | Pierschbacher et al. | |
| 5,598,615 A | 2/1997 | Takada | |
| 5,606,019 A | 2/1997 | Cappello | |
| 5,674,276 A * | 10/1997 | Andersen et al. | 623/1.5 |
| 5,760,176 A | 6/1998 | Pierschbacher et al. | |
| 5,771,716 A | 6/1998 | Schlussel | |
| 5,795,835 A * | 8/1998 | Bruner et al. | 442/310 |
| 5,849,040 A | 12/1998 | Kanehisa | |
| 5,919,232 A | 7/1999 | Chaffringeon et al. | |
| 5,951,506 A | 9/1999 | Tsubouchi | |
| 5,990,378 A | 11/1999 | Ellis | |
| 6,004,888 A * | 12/1999 | Sugimoto et al. | 442/60 |
| 6,006,552 A * | 12/1999 | Matsuda et al. | 66/193 |
| 6,042,592 A | 3/2000 | Schmitt | 606/151 |
| 6,074,722 A * | 6/2000 | Cuccias | 428/107 |
| 6,076,448 A * | 6/2000 | Rexroad | 87/12 |
| 6,090,116 A | 7/2000 | D'Aversa et al. | |
| 6,110,590 A | 8/2000 | Zarkoob et al. | |
| 6,113,623 A | 9/2000 | Sgro | |
| 6,136,022 A * | 10/2000 | Nunez et al. | 623/1.1 |
| 6,146,418 A | 11/2000 | Berman | |
| 6,164,339 A * | 12/2000 | Greenhalgh | 139/1 R |
| 6,171,984 B1* | 1/2001 | Paulson et al. | 442/331 |
| 6,175,053 B1 | 1/2001 | Tsubouchi | |
| 6,228,132 B1 | 5/2001 | Prince et al. | |
| 6,233,978 B1* | 5/2001 | Gehring et al. | 66/195 |
| 6,287,316 B1* | 9/2001 | Agarwal et al. | 606/151 |
| 6,287,340 B1 | 9/2001 | Altman et al. | |
| 6,302,922 B1 | 10/2001 | Kanehisa | |
| 6,303,136 B1 | 10/2001 | Li et al. | |
| 6,389,851 B1* | 5/2002 | Groshens | 66/192 |
| 6,408,656 B1 | 6/2002 | Ory et al. | |
| 6,440,740 B1 | 8/2002 | Tsubouchi et al. | |
| 6,443,964 B1 | 9/2002 | Ory et al. | |
| 6,540,773 B2* | 4/2003 | Dong | 623/1.13 |
| 6,592,617 B2* | 7/2003 | Thompson | 623/1.53 |
| 6,638,284 B1 | 10/2003 | Rousseau et al. | |
| 6,729,356 B1 | 5/2004 | Baker et al. | |
| 6,737,371 B1 | 5/2004 | Planck et al. | |
| 6,773,459 B2 | 8/2004 | Dauner et al. | |
| 6,783,554 B2 | 8/2004 | Amara et al. | |
| 6,827,743 B2* | 12/2004 | Eisermann et al. | 623/23.54 |
| 6,848,281 B2 | 2/2005 | Ishihara et al. | |
| 6,856,715 B1* | 2/2005 | Ebbesen et al. | 385/14 |
| 6,866,681 B2 | 3/2005 | Laboureau et al. | |
| 6,902,932 B2 | 6/2005 | Altman et al. | |
| 6,946,003 B1* | 9/2005 | Wolowacz et al. | 623/23.72 |
| 6,966,918 B1 | 11/2005 | Schuldt-Hempe et al. | |
| 6,971,252 B2 | 12/2005 | Therin et al. | |
| 7,021,086 B2 | 4/2006 | Ory et al. | |
| 7,025,063 B2* | 4/2006 | Snitkin et al. | 128/885 |
| 7,115,388 B2 | 10/2006 | Tsubouchi | |
| 7,156,858 B2 | 1/2007 | Schuldt-Hempe et al. | |
| 7,166,570 B2 | 1/2007 | Hunter et al. | |
| 7,285,637 B2 | 10/2007 | Armato et al. | |
| 7,293,433 B1 | 11/2007 | McMurray | |
| 7,331,199 B2 | 2/2008 | Ory et al. | |
| 7,338,531 B2 | 3/2008 | Ellis et al. | |
| 7,341,601 B2 | 3/2008 | Eisermann et al. | |
| 7,476,249 B2 | 1/2009 | Frank et al. | |
| 7,614,258 B2* | 11/2009 | Cherok et al. | 66/192 |
| 7,824,701 B2 | 11/2010 | Binette et al. | |
| 7,828,855 B2 | 11/2010 | Ellis et al. | |
| 7,842,780 B2 | 11/2010 | Kaplan et al. | |
| 7,875,074 B2 | 1/2011 | Chen et al. | |
| 7,900,484 B2 | 3/2011 | Cherok et al. | |
| 8,007,531 B2 | 8/2011 | Frank | |
| 8,177,834 B2* | 5/2012 | Carlson et al. | 623/1.51 |
| 8,197,542 B2 | 6/2012 | Becker | |
| 8,202,317 B2 | 6/2012 | Becker | |
| 8,226,715 B2* | 7/2012 | Hwang et al. | 623/13.14 |
| 2002/0156437 A1 | 10/2002 | McDevitt et al. | |
| 2003/0044155 A1* | 3/2003 | Maiden | 385/137 |
| 2003/0061839 A1* | 4/2003 | Kost | 66/192 |
| 2003/0087433 A1 | 5/2003 | Tsubouchi et al. | |
| 2003/0106346 A1* | 6/2003 | Matsumoto | 66/195 |
| 2003/0106347 A1* | 6/2003 | Kost | 66/195 |
| 2003/0165548 A1 | 9/2003 | Tsubouchi et al. | |
| 2003/0183978 A1 | 10/2003 | Asakura | |
| 2003/0228815 A1* | 12/2003 | Bhatnagar et al. | 442/164 |
| 2004/0005363 A1 | 1/2004 | Tsukada et al. | |
| 2004/0029478 A1 | 2/2004 | Planck et al. | |
| 2004/0170827 A1 | 9/2004 | Crighton | |
| 2004/0211225 A1* | 10/2004 | Dickerson | 66/142 |
| 2004/0219630 A1 | 11/2004 | Tsubouchi | |
| 2004/0224406 A1 | 11/2004 | Altman et al. | |
| 2005/0089552 A1 | 4/2005 | Altman et al. | |
| 2005/0240261 A1* | 10/2005 | Rakos et al. | 623/1.51 |
| 2005/0260706 A1 | 11/2005 | Kaplan et al. | |
| 2005/0288797 A1* | 12/2005 | Howland | 623/23.74 |
| 2006/0009835 A1* | 1/2006 | Osborne et al. | 623/1.13 |
| 2006/0013950 A1 | 1/2006 | Porter et al. | |
| 2006/0015184 A1* | 1/2006 | Winterbottom et al. | 623/18.11 |
| 2007/0088434 A1 | 4/2007 | Frank et al. | |
| 2007/0207186 A1* | 9/2007 | Scanlon et al. | 424/424 |
| 2008/0038236 A1 | 2/2008 | Gimble et al. | |
| 2008/0131509 A1 | 6/2008 | Hossainy et al. | |
| 2008/0176960 A1 | 7/2008 | Tsukada et al. | |
| 2008/0200086 A1* | 8/2008 | Porter et al. | 442/189 |
| 2008/0206302 A1 | 8/2008 | Sittinger et al. | |
| 2008/0228028 A1* | 9/2008 | Carlson et al. | 600/36 |
| 2008/0300683 A1 | 12/2008 | Altman et al. | |
| 2009/0024162 A1 | 1/2009 | Shalaby et al. | |
| 2009/0030454 A1 | 1/2009 | Knight et al. | |
| 2009/0214649 A1 | 8/2009 | Gazit et al. | |
| 2010/0023029 A1 | 1/2010 | Young et al. | |
| 2010/0145367 A1 | 6/2010 | Ratcliffe | |
| 2010/0209405 A1 | 8/2010 | Altman et al. | |
| 2010/0249924 A1 | 9/2010 | Powell et al. | |
| 2010/0256756 A1 | 10/2010 | Altman et al. | |
| 2011/0009960 A1 | 1/2011 | Altman et al. | |
| 2011/0022171 A1 | 1/2011 | Richter et al. | |
| 2011/0054604 A1 | 3/2011 | Becker et al. | |

(56) References Cited

U.S. PATENT DOCUMENTS

| | | |
|---|---|---|
| 2011/0054605 A1 | 3/2011 | Becker et al. |
| 2011/0106249 A1 | 5/2011 | Becker et al. |
| 2011/0167602 A1 | 7/2011 | Altman et al. |
| 2011/0171453 A1 | 7/2011 | Altman et al. |
| 2011/0184227 A1 | 7/2011 | Altman et al. |
| 2011/0189773 A1 | 8/2011 | Altman et al. |
| 2011/0190795 A1 | 8/2011 | Hotter et al. |
| 2011/0224703 A1 | 9/2011 | Mortarino et al. |
| 2011/0257665 A1 | 10/2011 | Mortarino et al. |
| 2011/0257761 A1 | 10/2011 | Mortarino et al. |
| 2011/0282365 A1 | 11/2011 | Hadba et al. |
| 2011/0301717 A1 | 12/2011 | Becker |
| 2012/0053690 A1 | 3/2012 | Frank |
| 2012/0165957 A1 | 6/2012 | Everland et al. |
| 2012/0184974 A1 | 7/2012 | Becker |
| 2012/0226352 A1 | 9/2012 | Becker |
| 2012/0244143 A1 | 9/2012 | Lo et al. |

FOREIGN PATENT DOCUMENTS

| | | |
|---|---|---|
| EP | 0677297 | 10/1995 |
| EP | 0889156 A1 | 12/1996 |
| EP | 1241178 | 9/2002 |
| EP | 2016956 | 1/2009 |
| EP | 2068766 | 10/2011 |
| JP | H06-245989 | 9/1994 |
| WO | 95-25550 | 9/1995 |
| WO | 00-57812 | 10/2000 |
| WO | WO 00/72782 | 12/2000 |
| WO | WO 02/29141 | 4/2002 |
| WO | WO 2004/062697 | 7/2004 |
| WO | WO 2005/123114 | 12/2005 |
| WO | 2006102477 | 9/2006 |
| WO | WO 2009/023615 | 2/2009 |
| WO | WO 2010/074827 | 7/2010 |
| WO | WO 2010/141133 | 12/2010 |

OTHER PUBLICATIONS

Cappello et al., In-situ self-assembling protein polymer gel systems for administration, delivery, and release of drugs, *USA Journal of controlled release: official journal of the Controlled Release Society* (Apr. 30, 1998), 53(1-3):105-17, San Diego, CA 92121.

Horan et al., In vitro degradation of silk fibroin, *USA Biomaterials* (Jun. 2005), 26(17):3385-93.

Horan, et al., Biological and biomechanical assessment of a long-term bioresorbable silk-derived surgical mesh in an abdominal body wall defect model, *Hernia* (2009) 13(2):189-99.

Kardestuncer et al., RGD-tethered silk substrate stimulates the differentiation of human tendon cells, *Clinical Orthopaedics and Related Research* (2006), No. 448:pp. 234-239.

Kundu et al., Natural protective glue protein, sericin bioengineered by silkworms: Potential for biomedical and biotechnological applications, *Progress in Polymer Science* (2008) 33:998-1012.

Panilaitis et al., Macrophage responses to silk, *Biomaterials* (2003) 24(18):3079-3085.

Tamada, Y., Symposium Preprints, *The Society of Fiber Science and Technology* (1998) p. S-51.

Tsukada, Preparation and application of porous silk fibroin materials, *Journal of Applied Polymer Science* (1994).

Yanagisawa et al., Improving cell-adhesive properties of recombinant bombyx mori silk by incorporation of collagen or fibronectin derived peptides produced by transgenic silkworms, *Biomacromolecules* (2007), 8 (11):3487-3492.

Zhu et al., Preparation and Characterization of Regenerated Bombyx mori silk fibroin fiber containing recombinant cell-adhesive proteins; nonwoven fiber and monofilament, *Journal of Applied Polymer Science* (2008), vol. 109:2956-2963.

\* cited by examiner

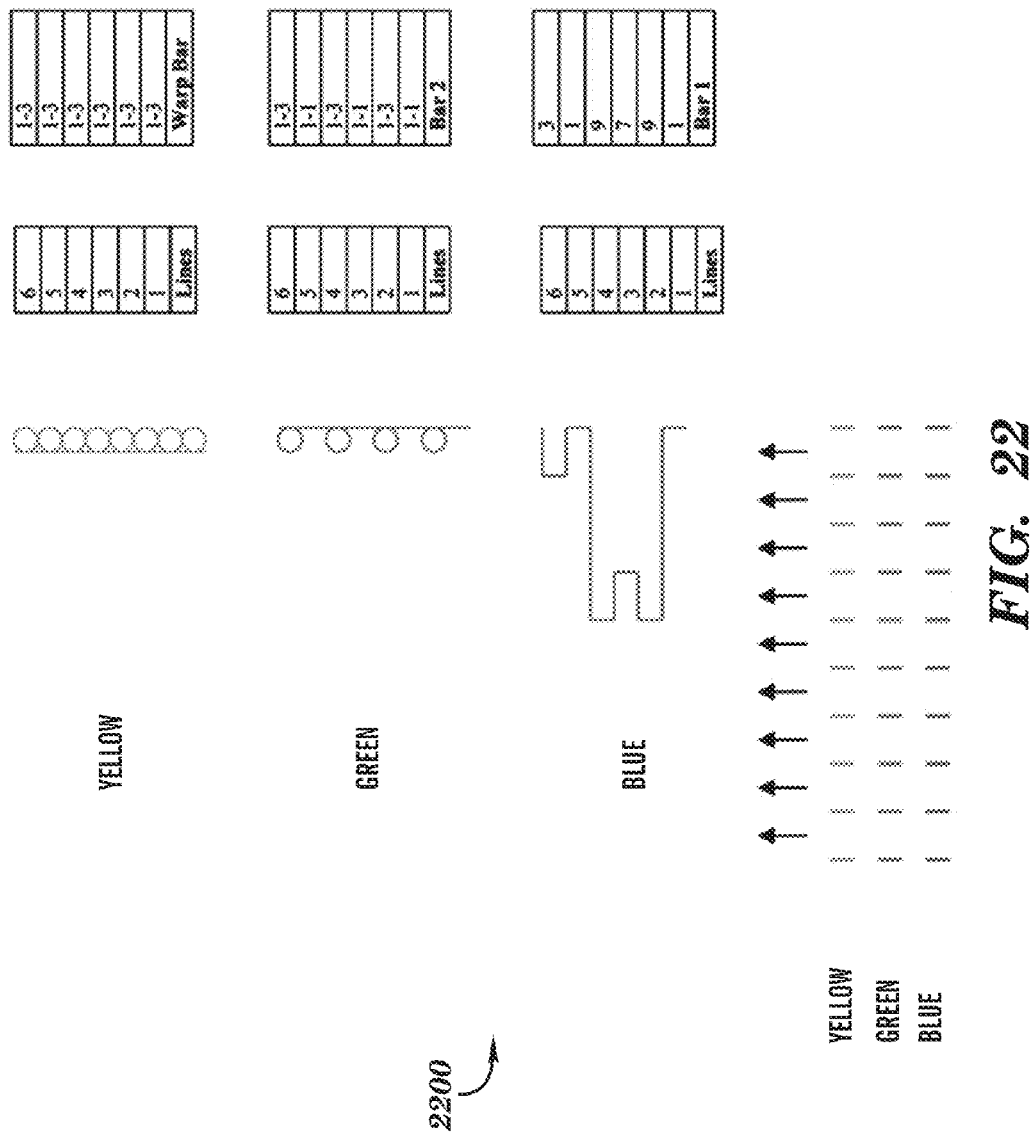

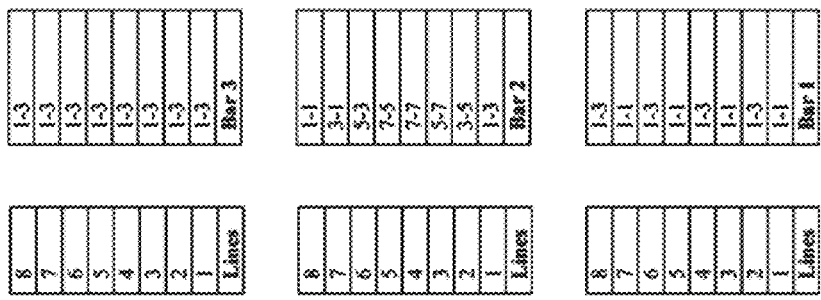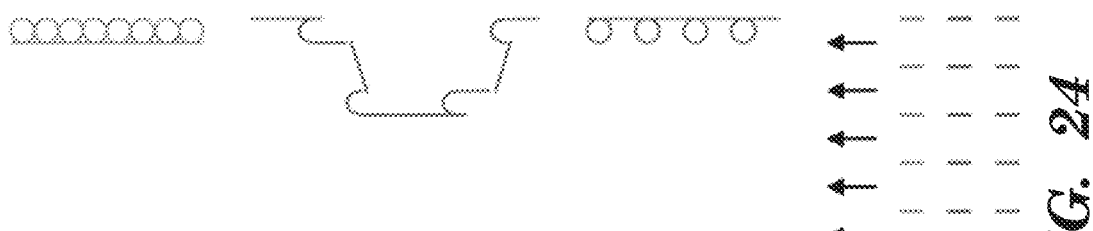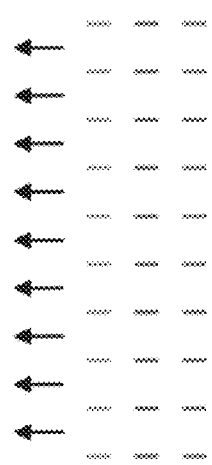
FIG. 24

BIOCOMPATIBLE SURGICAL SCAFFOLD WITH VARYING STRETCH

CROSS-REFERENCE TO RELATED APPLICATIONS

This application is a continuation-in-part application which claims priority to U.S. utility patent application Ser. No. 12/680,404, filed Mar. 26, 2010, which is a national stage entry of PCT/US09/63717, filed Nov. 9, 2009, which claims priority to U.S. provisional patent application No. 61/122,520, filed Dec. 15, 2008, all of which applications are hereby expressly incorporated by reference herein in their entireties.

FIELD OF THE INVENTION

The present invention generally relates to a prosthetic device for tissue repair, and, more particularly, to a surgical silk mesh device employing a stable knit structure.

BACKGROUND OF THE INVENTION

Surgical mesh initially used for hernia and abdominal wall defects are now being used for other types of tissue repair, such as rotator cuff repair, pelvic floor dysfunction, and reconstructive or cosmetic surgeries. It is projected that in 2010, there will be more than 8 million hernia procedures, 800,000 rotator cuff repairs, 3 million pelvic prolapse repairs, 600,000 urinary incontinence repairs, and 1.5 million reconstructive or aesthetic plastic surgeries. Most of these procedures will likely employ implantable surgical mesh devices currently on the market, including: Bard Mesh (polypropylene) by C. R. Bard; Dexon (polyglycolic acid) by Synecture/US Surgical; Gore-Tex (polytetrafluoroethylene) by W. L. Gore; Prolene (polypropylene), Prolene Soft (polypropylene), Mersilene Mesh (polyester), Gynemesh (polypropylene), Vicryl Knitted Mesh (polyglactin 910), TVT (polypropylene) by Ethicon; Sparc tape (polypropylene) by American Medical Systems; and IVS tape (polypropylene) by TYCO Healthcare International.

Surgical mesh devices are typically biocompatible and may be formed from bioresorbable materials and/or non-bioresorbable materials. For example, polypropylene, polyester, and polytetrafluoroethylene (PTFE) are biocompatible and non-bioresorbable, while polyglactin 910 and polyglycolic acid are biocompatible and bioresorbable.

Though current surgical mesh devices may be formed from different materials, they have various similar physical and mechanical characteristics beneficial for tissue repair. However, despite the benefits provided by current surgical mesh devices, their use may be accompanied by a variety of complications. Such complications, for example, may include scar encapsulation and tissue erosion, persistent infection, pain, and difficulties associated with revision surgery. In addition, the use of an absorbable material may result in reoccurrence due to rapid resorption of the implant material and loss of strength.

Although polypropylene monofilament may be a highly regarded material for surgical mesh devices, polypropylene mesh devices can induce intense scar formations and create a chronic foreign body reaction with the formation of a fibrous capsule, even years after implantation. Minor complaints of seromas, discomfort, and decreased wall mobility are frequent and observed in about half of the patients implanted with polypropylene mesh devices. Moreover, polypropylene generally cannot be placed next to the bowel due to the propensity of adhesion formation.

Although the use of multifilament polyester may improve conformity with the abdominal wall, it is also associated with a variety of disadvantages. For example, higher incidences of infection, enterocutaneous fistula formation, and small bowel obstruction have been reported with the use of multifilament polyester compared to other materials. Indeed, the small interstices of the multifilament yarn make it more susceptible to the occurrence of infection, and thus multifilament polyester is not commonly used within the United States.

The use of polytetrafluoroethylene (PTFE) may be advantageous in minimizing adhesions to the bowel. However, the host tissue encapsulates the PTFE mesh, resulting in weak in-growth in the abdominal wall and weaker hernia repair. This material, though not a good mesh material on its own, has found its place as an adhesion barrier.

Absorbable materials, such as Vicryl and Dexon, used for hernia repair have the advantage of being placed in direct contact with the bowel without adhesion or fistula formation. A study has observed that Vicryl has comparable burst strength to nonabsorbable mesh at three weeks but is significantly weaker at twelve weeks due to a quick absorption rate. Meanwhile, the same study observed that Dexon has more in-growth at twelve weeks with less absorption of the mesh. The concern with absorbable meshes is that the rate of absorption is variable, possibly leading to hernia recurrence if the proper amount of new tissue is not there to withstand the physiologic stresses placed on the hernia defect.

A significant characteristic of a biomaterial is its porosity, because porosity is the main determinant for tissue reaction. Pore sizes of >500-600 μm permit in-growth of soft tissue; pore sizes of >200-300 μm favor neo-vascularisation and allow mono-morphological restitution of bony defects; pore sizes of <200 μm are considered to be almost watertight, hindering liquid circulation at physiological pressures; and pores of <100 μm only lead to in-growth of single cell types instead of building new tissues. Finally, a pore size of <10 μm hinders any in-growth and increases the chance of infection, sinus tract formation, and encapsulation of the mesh. Bacteria averaging 1 μm in size can hide in the small interstices of the mesh and proliferate while protected from neutrophilic granulocytes averaging 10-15 μm.

Other important physical characteristics for surgical mesh devices include thickness, burst strength, and material stiffness. The thickness of surgical mesh devices vary according to the particular repair procedure. For example, current surgical mesh device hernia, pelvic floor dysfunction, and reconstructive/cosmetic procedures range in thickness from approximately 0.635 mm to 1.1 mm. For rotator cuff repair, a thickness of 0.4 mm to 5 mm is typically employed.

Intra-abdominal pressures of 10-16 N, with a mean distension of 11-32% results in the need for a surgical mesh with a burst strength that can resist the stress of the inner abdomen before healthy tissue comes into being.

Material stiffness is an important mechanical characteristic for surgical mesh, especially when used for pelvic floor dysfunction, because material stiffness has been associated with the likelihood of tissue erosion. Surgical mesh devices formed from TVT, IVS, Mersilene, Prolene, Gynemesh, Sparc tape, for example, currently have an ultimate tensile strength (UTS) that exceeds the forces exerted by intra-abdominal pressures of 10-16 N. With the low force in the abdomen, the initial stiffness of the material is an important consideration. Moreover, the stiffness may exhibit non-linear behavior most likely due to changes in the fabric structure, e.g., unraveling of the knit, weave, etc. A surgical mesh device of lesser stiffness may help reduce tissue erosion and may conform to the contours of the body more effectively.

With regard to soft tissue repair, in particular, surgical meshes and scaffolds have been used historically in a variety of applications to reinforce soft tissue where defects or weakness exist. They are widely used for breast and chest wall reconstruction, strengthening tissues, providing support for internal organs, and treating surgical or traumatic wounds. They are usually made of inert materials and polymers such as Teflon®, polypropylene, polyglycolic acid, polyester, polyglactin 910, etc., although a titanium mesh has been used in some spinal surgeries. But the use of tissue based materials such as acellular dermal matrix (ADM) from human and animal derived dermis is also becoming more popular.

Some examples of the surgical mesh devices that are currently available in the market are Bard Mesh by C. R. Bard; Dexon by Synecture/US surgical; Gore-Tex by W. L. Gore; Prolene, Prolene Soft, Mersilene Mesh, Gynemesh, Vicryl Knitted Mesh, and TVT by Ethicon. Some examples of the surgical acellular dermal matrix devices that are currently available are Alloderm and Strattice by Lifecell, FlexHD by Ethicon, DermaMatrix by Synthes and Permacol by Covidien.

Surgical mesh devices are typically biocompatible and can be made from bioresorbable and/or non-bioresorbable material. For example, Teflon®, polypropylene and polyester are biocompatible and non-bioresorbable while polyglycolic acid and polyglactin 910 are biocompatible and bioresorbable. ADM is processed by removing the cells and epidermis, if applicable, from the donor tissue and leaving only natural biologic components. The most common tissue based materials are human, porcine or equine derived dermal matrix.

One application for soft tissue reconstruction that uses surgical mesh or ADM is breast reconstruction post mastectomy. The aim of breast reconstructive surgery is to restore a woman's breasts to a near normal appearance and shape following the surgical removal of a breast (mastectomy), a crucial step towards emotional healing in women who have been faced with losing their breast as a result of a medical condition such as breast cancer. According to the American Society of Plastic Surgeons (ASPS), approximately 60,000 surgical procedures occur in the US related to non-cosmetic breast reconstruction. Internationally, that number surpasses 80,000 procedures when major industrialized countries are taken into consideration. A contoured, structural and tailored scaffold device designed to meet the unique needs of the breast reconstruction population where a massive loss of tissue occurs and which would work with the body's own immune process to restore the environment to a more natural state would provide a compassionate solution to a significant unmet need.

The breast reconstruction surgical procedure is commonly performed with two different methods, both using ADM as the preferred matrix. The main advantage of ADM over other available surgical meshes is the higher rate of revascularization, providing support and coverage of the defect while preventing infection and capsular contraction. The first method, a one stage reconstruction uses ADM to fully reconstruct the shape of the breast in conjunction with a breast implant at the time of the surgical procedure. The second method, a two stages reconstruction; the first stage consisting of the placement of (a) tissue expander(s) (at the time of mastectomy or later) with ADM to reconstruct the breast; follow by tissue expander expansion with saline solution to expand the muscle and skin tissue; the second and final stage consisting of the replacement of the tissue expander with an implant. In both procedures the pocket for the tissue expander or the implant is created by releasing the inferior origin of the pectoralis muscle and electrocauterizing a subpectoral pocket. A sheet of ADM is centered over the defect and it is sutured to the inframammary fold with continuous or interrupted sutures. The tissue expander or implant is inserted and positioned inside the subpectoralis pocket created. The rest of the ADM is cut to the necessary shape and it is sutured to the inferior edge of the pectoralis muscles, while on the lateral border is sutured to the *pectoralis* and serratus muscles.

A breast reconstruction procedure alternative to the one described above using ADM is performed with autologous tissue such as TRAM flap. In this surgical procedure, the breast is reconstructed by using a portion of the abdomen tissue group that has been surgically removed, including the skin, the adipose tissue, minor muscles and connective tissue. This abdomen tissue group is taken from the patient's abdomen and transplanted onto the breast site using a similar method as described above with ADM.

The quality of the resulting reconstruction is impacted by subsequent treatment, e.g. post-mastectomy radiation weakens skin tissue, the amount of tissue available e.g. thinner women often lack sufficient tissue, and the overall health and habits (smoking) of the individual. Tissue expanders, balloon type devices, are frequently used in an attempt to stretch the harvested skin to accommodate the breast implant. However, harvested tissue has limitations in its ability to conform to the natural breast contour resulting in unacceptable results, including a less than ideal positioning or feel of the breast implant. A scaffold device that can be used as an internal scaffold to act as a "bra" to immediately support a geometrically complex implantation site at the time of surgery would ideally provide the body both the time and structure necessary for optimal healing.

Breast reconstruction in two stages with a tissue expander and ADM followed by the replacement of the tissue expander with an implant has become the most common technique adopted by surgeons. A main advantage is the lengthening of the pectoralis major muscle therefore preventing the commonly referred to as "window shading" after the muscle is released. Another main advantage is the control of the inframammary fold position and shape as well as the lateral breast border.

The use of ADM has advantages against the common surgical mesh devices by lowering the rate of capsular contraction and infection; however despite its low overall complication rate, the procedure is not without risk since ADM can generate a host inflammatory reaction and sometimes present infection. Also, it is very important to note that the properties of ADM are limited to the properties of the tissue that is harvested which can result in variability.

SUMMARY OF THE INVENTION

In view of the disadvantages of current surgical mesh devices, there continues to be a need for a surgical mesh that is biocompatible and absorbable, has the ability to withstand the physiological stresses placed on the host collagen, and minimizes tissue erosion, fistulas, or adhesions. Thus, embodiments according to aspects of the present invention provide a biocompatible surgical silk mesh prosthetic device for use in soft and hard tissue repair. Examples of soft tissue repair include hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open structure of these embodiments allows tissue in-growth while the mesh device degrades at a rate which allows for a smooth transfer of mechanical properties to the new tissue from the silk scaffold. According to a particular aspect of the present invention, embodiments employ a knit pattern, referred to as a "node-lock" design. The "node-lock" design substantially prevents unraveling and preserves the stability of the mesh device, especially when the mesh device is cut.

In a particular embodiment, a prosthetic device includes a knitted mesh including at least two yarns laid in a knit direction and engaging each other to define a plurality of nodes, the at least two yarns including a first yarn and a second yarn extending between and forming loops about two nodes, the second yarn having a higher tension at the two nodes than the first yarn, the second yarn substantially preventing the first yarn from moving at the two nodes and substantially preventing the knitted mesh from unraveling at the nodes.

In an example of this embodiment, the first yarn and the second yarn are formed from different materials. In another example of this embodiment, the first yarn and the second yarn have different diameters. In further embodiments, wherein the first yarn and the second yarn have different elastic properties. In yet a further example of this embodiment, the at least two yarns are formed from silk.

In another example of this embodiment, a first length of the first yarn extends between the two nodes and a second length of the second yarn extends between the two nodes, the first length being greater than the second length. For instance, the first yarn forms an intermediate loop between the two nodes and the second yarn does not form a corresponding intermediate loop between the two nodes. The first length of the first yarn is greater than the second length of the second yarn.

In yet another example of this embodiment, the first yarn is included in a first set of yarns and the second yarn is included in a second set of yarns, the first set of yarns being applied in a first wale direction, each of the first set of yarns forming a first series of loops at each of a plurality of courses for the knitted mesh, the second set of yarns being applied in a second wale direction, the second wale direction being opposite from the first wale direction, each of the second set of yarns forming a second series of loops at every other of the plurality of courses for the knitted mesh, the first set of yarns interlacing with the second set of yarns at the every other course to define the nodes for the knitted mesh, the second set of yarns having a greater tension than the first set of yarns, the difference in tension substantially preventing the knitted mesh from unraveling at the nodes.

In a further example of this embodiment, the first yarn is included in a first set of yarns and the second yarn is included in a second set of yarns, the first set of yarns and the second set of yarns being alternately applied in a wale direction to form staggered loops, the first set of yarns interlacing with the second set of yarns to define the nodes for the knitted mesh, the alternating application of the first set of yarns and the second set of yarns causing the first set of yarns to have different tensions relative to the second set of yarns at the nodes, the difference in tension substantially preventing the knitted mesh from unraveling at the nodes.

In yet a further example of this embodiment, the first yarn is included in a first set of yarns and the second yarn is included in a second set of yarns, the first set of yarns forming a series of jersey loops along each of a first set of courses for a knitted mesh, the second set of yarns forming a second series of alternating tucked loops and jersey loops along each of a second set of courses for the knitted mesh, the second set of courses alternating with the first set of courses, the second set of yarns having a greater tension than the first set of yarns, the tucked loops of the second set of yarns engaging the jersey loops of the first set of yarns to define nodes for the knitted mesh, the tucked loops substantially preventing the knitted mesh from unraveling at the nodes.

In another particular embodiment, a method for making a knitted mesh for a prosthetic device, includes: applying a first set of yarns in a first wale direction on a single needle bed machine, each of the first set of yarns forming a first series of loops at each of a plurality of courses for a knitted mesh; applying a second set of yarns in a second wale direction on the single needle bed machine, the second wale direction being opposite from the first wale direction, each of the second set of yarns forming a second series of loops at every other of the plurality of courses for the knitted mesh; and applying a third set of yarns in every predetermined number of courses for the knitted mesh, the application of the third set of yarns defining openings in the knitted mesh, wherein the first set of yarns interlaces with the second set of yarns at the every other course to define nodes for the knitted mesh, and the second set of yarns has a greater tension than the first set of yarns, the difference in tension substantially preventing the knitted mesh from unraveling at the nodes.

In yet another embodiment, a method for making a knitted mesh for a prosthetic device, includes: applying a first set of yarns to a first needle bed of a double needle bed machine in a wale direction; applying a second set of yarns to a second needle bed of the double needle bed machine in a wale direction; and applying a third set of yarns in every predetermined number of courses for the knitted mesh, the application of the third set of yarns defining openings in the knitted mesh, wherein the first set of yarns and the second set of yarns are alternately applied to form staggered loops at the first needle bed and the second needle bed, respectively, and the first set of yarns interlaces with the second set of yarns to define nodes for the knitted mesh, the alternating application of the first set of yarns and the second set of yarns causing the first set of yarns to have a different tension relative to the second set of yarns at the nodes, the difference in tension substantially preventing the knitted mesh from unraveling at the nodes.

In a further particular embodiment, a method for making a knitted mesh for a prosthetic device, includes: forming, on a flat needle bed machine, a first series of jersey loops along each of a first set of courses for a knitted mesh; and forming, on the flat needle bed machine, a second series of alternating tucked loops and jersey loops along each of a second set of courses for the knitted mesh, the second set of courses alternating with the first set of courses; wherein the second set of courses has a greater tension than the first set of courses, and the tucked loops along the second set of courses engage the jersey loops of the first set of courses and substantially prevents the knitted mesh from unraveling at the tucked loops. In an example of this embodiment, a continuous yarn forms the first set of courses and the second set of courses. In another example of this embodiment, the first set of courses and the second set of courses are formed by different yarns. In yet another example of this embodiment, the first set of courses and the second set of courses are formed by different yarns having different diameters.

In the view of the current commercial surgical meshes and ADM with the current surgical procedure, there continues to be a need for a bioresorbable and biocompatible surgical scaffold that has the ability to withstand the physiological stress and minimize infection, capsular contraction and host tissue response. The embodiments according to the present invention provide a silk based surgical scaffold with different stretch regions that degrades at a rate where smooth transfer of mechanical properties from the scaffold to new tissue is possible.

In a preferred embodiment this invention is a knitted scaffold prepared from a multifilament silk yarn. This scaffold has two regions parallel to each other that differ in the mechanical properties consisting of a stretchy region and a stiffer region.

Furthermore scaffolds constructed in accordance with the present embodiments may demonstrate superior performance with breast reconstruction surgery when a scaffold with variable stretch is desired. The high stretch region of the scaffold with low stiffness and high flexibility provides projection of the breast while offering shapeability. The low stretch region of the scaffold with high stiffness and low flexibility provides definition of the inframammary fold with the initial support for the tissue expander. Furthermore, the low stretch region will provide better support for suture anchoring than the high stretch region.

In another preferred embodiment the scaffold has two regions that follow the shape of the inframammary fold differing in the mechanical properties consisting of a stretchy region and a stiffer region as described in the previous embodiment. The low stretch region of the scaffold with high stiffness and low flexibility provides definition of the inframammary fold around its lateral and lower border with the initial support for the tissue expander.

In another preferred embodiment the scaffold is formed by one region that is shaped at its perimeter to follow the contour of the defect to be repaired. For breast reconstruction applications the preferred shape is represented by an elliptical form. The mechanical properties of the scaffold may be selected to better enhance the breast shape and size requirement.

The mesh or scaffold designs of the present invention are suitable for use in a variety or reconstructive or support applications including, but not limited to, breast reconstruction, mastopexy, breast augmentation revision, breast augmentation support, standard breast augmentation, chest wall repair, organ support, body contouring, abdominoplasty, facial reconstruction, hernia repair, and pelvic floor repair.

All these intelligent designs offer significant improvement over the ADM since they offer the ability to manipulate the properties based on the specific area of use such as laying load bearing members in a specific area. With ADM the properties are only dictated by the harvest tissue properties which can be variable.

All these and other aspects of the present invention will become more apparent from the following detailed description of the preferred embodiments of the present invention when viewed in conjunction with the accompanying drawings.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 2 illustrates an example mesh produced on a double needle bed warp knitting machine according to aspects of the present invention. Thus.

FIG. 22 illustrates an example pattern layout for a single needle bed mesh according to aspects of the present invention.

FIG. 24 illustrates an example pattern layout for a single needle bed mesh according to aspects of the present invention.

FIGS. 37A and 37B illustrate an example pattern layout for a double needle bed scaffold according to aspects of the present invention from FIG. 35 for ground bar #2.

As shown in FIG. 42, the scaffold is shaped in order to create a three-dimensional shape such as for use in breast reconstruction or other such applications. The design is created by using a double needle bed knitter and changing the picks per unit length and the feed rate. This shaped design may allow surgeons to create a more normal looking breast.

FIGS. 45A and 45B illustrate an example pattern layout for a double needle bed scaffold according to aspects of the present invention from FIG. 42 for elliptical effect bar #2.

FIGS. 46A and 46B illustrate an example pattern layout for a double needle bed scaffold according to aspects of the present invention from FIG. 42 for ground bar #3.

FIGS. 47A and 47B illustrate an example pattern layout for a double needle bed scaffold according to aspects of the present invention from FIG. 42 for pattern bar #4.

DETAILED DESCRIPTION

Figure 1A:
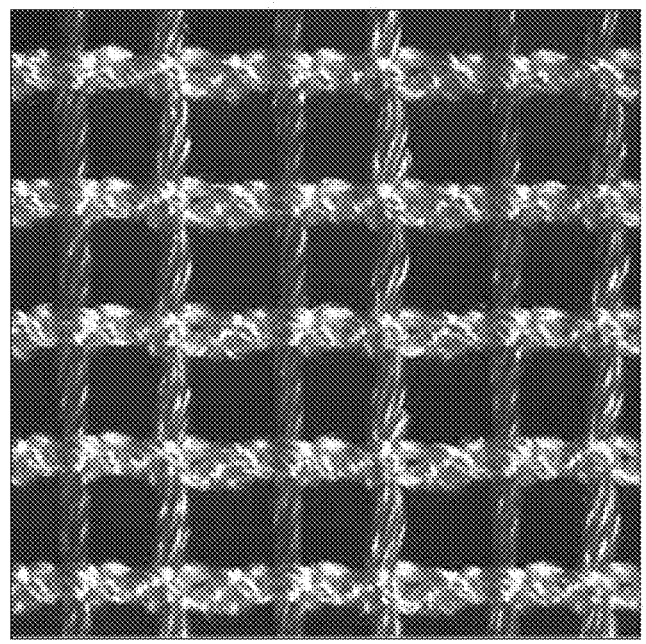
FIG. 1A illustrates the technical back of an example mesh produced on a single needle bed warp knitting machine according to aspects of the present invention.

Embodiments according to aspects of the present invention provide a biocompatible surgical silk mesh device for use in soft or hard tissue repair. Examples of soft tissue repair include breast reconstruction, hernia repair, rotator cuff repair, cosmetic surgery, implementation of a bladder sling, or the like. Examples of hard tissue repair, such as bone repair, involve reconstructive plastic surgery, ortho trauma, or the like.

Advantageously, the open and porous structure of these embodiments allows tissue in-growth while the mesh bioresorbs at a rate which allows for a smooth transfer of mechanical properties to the new tissue from the silk scaffold. It also allows tissue in-growth along the open pore area as well as the scaffold area. Furthermore, embodiments employ a knit pattern that substantially prevents unraveling under tension, especially when the mesh device is cut such as by a surgeon. In particular, embodiments may preserve the stability of the mesh device by employing a knit pattern that takes advantage of variations in tension between at least two yarns laid in a knit direction. For example, a first yarn and a second yarn may be laid in a knit direction to form "nodes" for a mesh device. The knit direction for the at least two yarns, for example, may be vertical during warp knitting or horizontal during weft knitting. The nodes of a mesh device, also known as inter-mesh loops, refer to intersections in the mesh device where the two yarns form a loop around a knitting needle. In some embodiments, the first yarn is applied to include greater slack than the second yarn, so that, when a load is applied to the mesh device, the first yarn is under a lower tension than the second device. A load that places the at least two yarns under tension may result, for example, when the mesh device is sutured or if there is pulling on the mesh device. The slack in the first yarn causes the first yarn to be effectively larger in diameter than the second yarn, so that the first yarn experiences greater frictional contact with the second yarn at a node and cannot move, or is "locked," relative to the second yarn. Accordingly, this particular knit design may be referred to as a "node-lock" design.

In general, node-lock designs according to aspects of the present invention employ at least two yarns under different tensions, where a higher tension yarn restricts a lower tension yarn at the mesh nodes. To achieve variations in tension between yarns, other node-lock designs may vary the yarn diameter, the yarn materials, the yarn elastic properties, and/or the knit pattern. For example, the knit pattern described previously applies yarns in varying lengths to create slack in some yarns so that they experience less tension. Because the lower tension yarn is restricted by the higher tension yarn, node-lock designs substantially prevent unraveling of the mesh when the mesh is cut. As such, the embodiments allow the mesh device to be cut to any shape or size while maintaining the stability of the mesh device. In addition, node-lock designs provide a stability that makes it easy to pass the mesh device through a cannula for laparoscopic or arthroscopic surgeries without damaging the material.

Although the node-lock design may employ a variety of polymeric biocompatible materials, a scaffold device using silk is the preferred material. A mesh device using silk according to aspects of the present invention can bioresorb at a rate sufficient to allow tissue in-growth while slowly transferring the load-bearing responsibility to the native tissue. Particular embodiments may be formed from *Bombyx mori* silkworm silk fibroin. The raw silk fibers have a natural globular protein coating known as sericin, which may have antigenic properties and must be depleted before implantation. Accordingly, the yarn is taken through a depletion process. The depletion of sericin is further described, for example, by Gregory H. Altman et al., "Silk matrix for tissue engineered anterior cruciate ligaments," Biomaterials 23 (2002), pp. 4131-4141, the contents of which are incorporated herein by reference. As a result, the silk material used in the device embodiments contains substantially no sensitizing agents, in so far as can be measured or predicted with standardized biomaterials test methods.

A surgical mesh device according to aspects of the present invention may be created on a single needle bed Comez Acotronic/600-F or a Comez 410 ACO by the use of three movements as shown in the pattern layout 2200 in FIG. 22: two movements in the wale direction, the vertical direction within the fabric, and one in the course direction, the horizontal direction of the fabric. The movements in the wale direction go in opposing directions; a first yarn moving in one direction loops every course while the second yarn moving in the opposite direction loops every other course. The yarns follow a repeated pattern of 3-1 and 1-1/1-3 on a 20 gauge knitting machine, using only half of the needles available on the needle bed. The interlacing of the loops within the fabric allow for one yarn to become under more tension than the other under stress, locking it around the less tensioned yarn; keeping the fabric from unraveling when cut. The other movement within the fabric occurs in every few courses creating the openings in the mesh. These yarns follow a pattern of 1-9/9-7/7-9/9-1/1-3/3-1. These yarns create tension within the fabric when under stress, locking the yarns in the fabric; preventing the fabric from unraveling.

Figure 26:
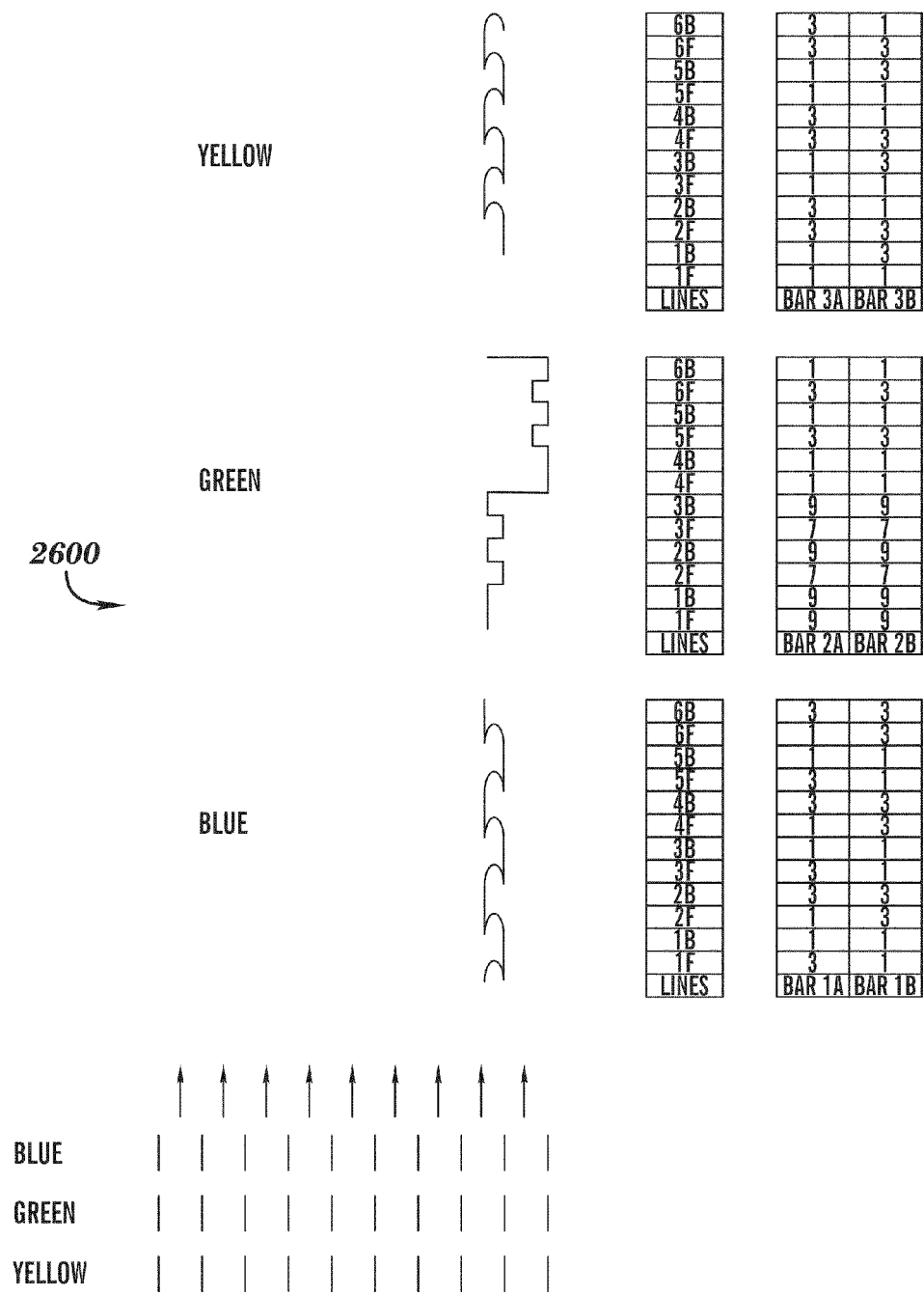
FIG. 26 illustrates an example pattern layout of the double needle bed mesh according to aspects of the present invention.

A surgical mesh device according to aspects of the present invention may be created on a double needle bed Comez DNB/EL-800-8B knitting machine by the use of three movements as shown in the pattern layout 2600 in FIG. 26: two movements in the wale direction and one in the course direction. The two movements in the wale direction occur on separate needle beds with alternate yarns; loops that occur in every course movement are staggered within the repeat. The yarns follow a repeated pattern of 3-1/1-1/1-3/3-3 and 1-1/1-3/3-3/3-1. The third movement happens with the yarn that traverses the width of the fabric. The yarn follows the pattern 9-9/9-9/7-7/9-9/7-7/9-9/1-1/1-1/3-3/1-1/3-3/1-1. This fabric is also made at half gauge on a 20 gauge knitting machine and prevents unraveling due to the tension created between the yarns when stressed. The repeat the yarn follows within the pattern is illustrated in FIG. 26.

Figure 23:
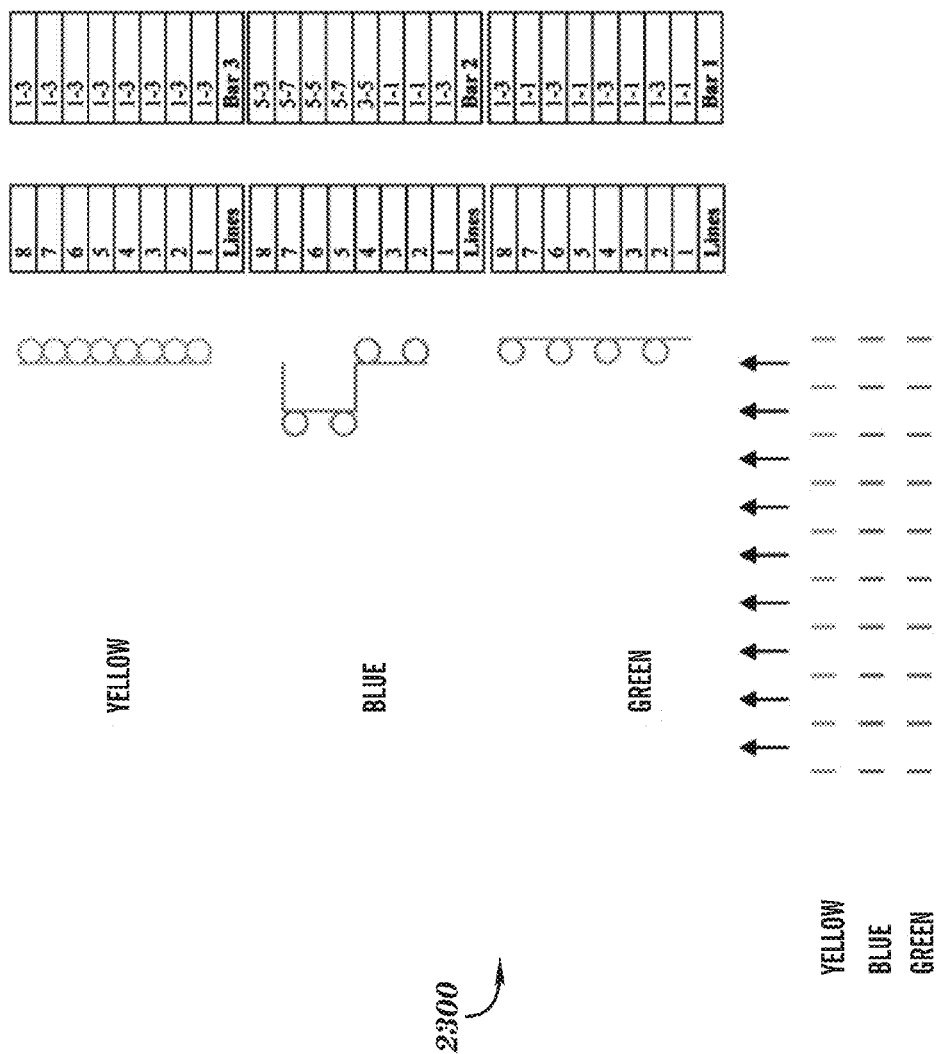
FIG. 23 illustrates an example pattern layout for a single needle bed mesh according to aspects of the present invention.
Figure 25:
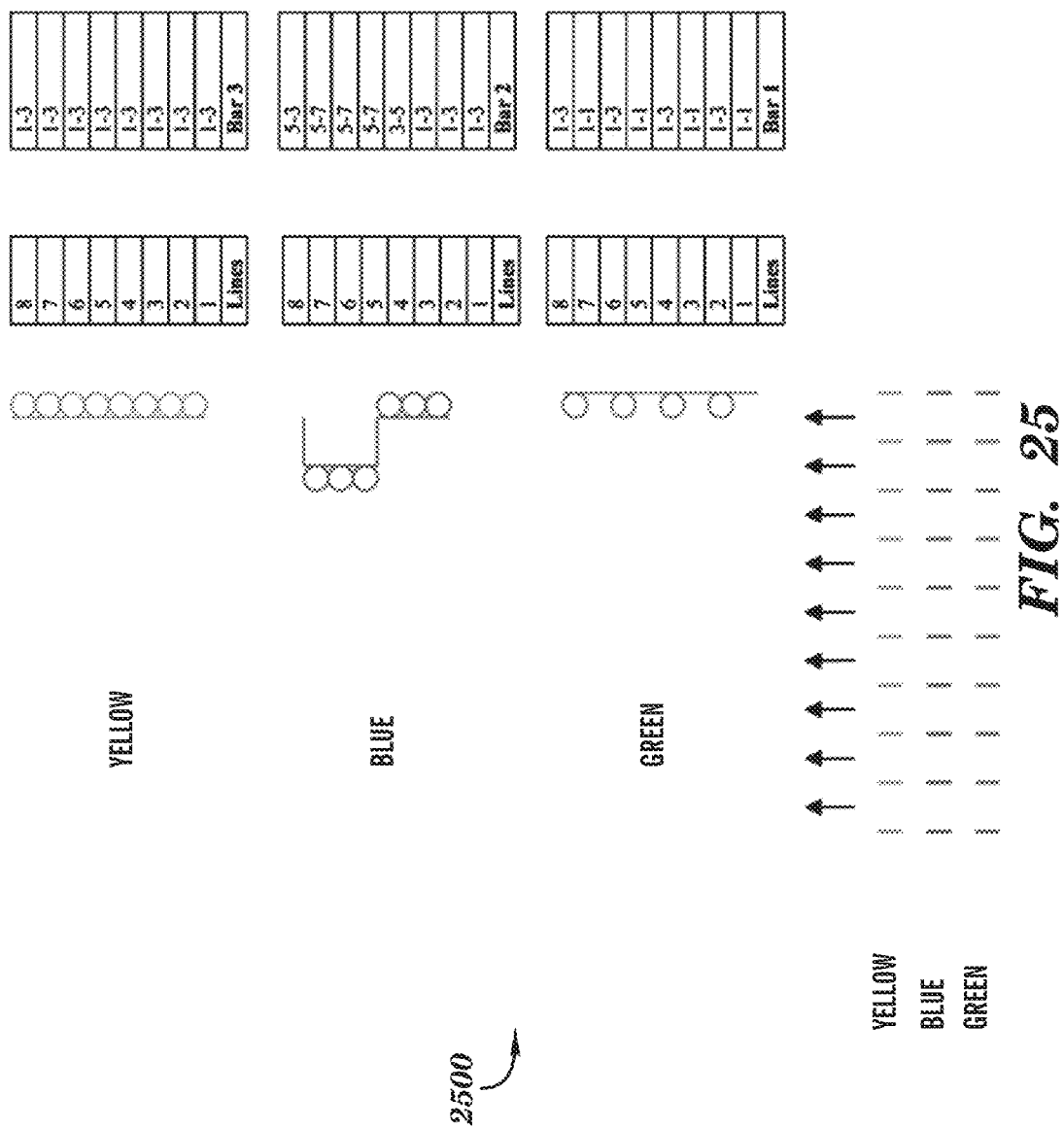
FIG. 25 illustrates an example pattern layout for the single needle bed mesh according to aspects of the present invention.

According to the pattern layouts 2300, 2400, and 2500 illustrated in FIGS. 23, 24 and 25, respectively, variations of the surgical mesh pattern are demonstrated for the Single Needle Bed including knitting with an added warp bar in place of using a weft bar insertion. These variations include knitting with the node lock yarns while moving it perpendicularly to one or more wales. These variations may include, but are not limited to, knitting either an open or closed chain stitch in either all or alternating courses. Utilizing a third warp bar, as opposed to a weft bar insertion can also be applied to the double needle warp knitting machine.

Figure 27:
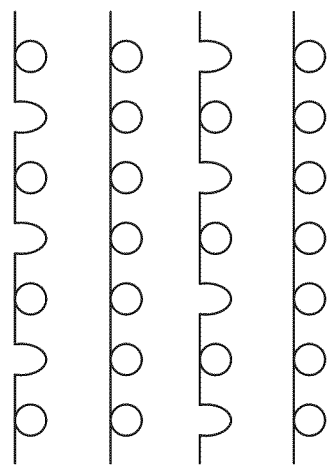
FIG. 27 illustrates an example pattern layout for the double needle bed weft knitting machine according to aspects of the present invention.

A surgical mesh device according to aspects of the present invention may be formed on the Shima Seiki flat needle bed machine as shown in the pattern layout 2700 in FIG. 27. This knit includes a continuous yarn or at least two different yarn sizes, one of which could be, though not limited to a different material. The knitted mesh would be formed by a regular jersey knit on the first row with loops formed by either a continuous yarn or a yarn of a certain yarn size, while the loops in the second row are formed by tucked loops that occur alternately with jersey knit loops of the same continuous yarn or with a yarn of a different size. The mesh would be shaped during knitting by use of increasing or decreasing stitches; a fashioning technique.

In embodiments employing silk yarn, the silk yarn may be twisted from yarn made by 20-22 denier raw silk fibers approximately 40 to 60 μm in diameter. Preferably, raw silk fibers ranging from 10 to 30 denier may be employed; however any fiber diameters that will allow the device to provide sufficient strength to the intended area are acceptable. Advantageously, a constant yarn size may maximize the uniformity of the surgical mesh mechanical properties, e.g. stiffness, elongation, etc., physical and/or biological properties. However, the yarn size may be varied in sections of the surgical mesh in order to achieve different mechanical, physical and/or biological characteristics in the preferred surgical mesh locations. Factors that may influence the size of the yarn include, but are not limited to: ultimate tensile strength (UTS); yield strength, i.e. the point at which yarn is permanently deformed; percent elongation; fatigue and dynamic laxity (creep); bioresorption rate; and transfer of cell/nutrients into and out of the mesh. The knit pattern layouts 2200, 2300, 2400, 2500, and 2600 illustrated in FIGS. 22-26, respectively, may be knitted to any width limited by the knitting machine width and could be knitted with any of the gauges available with the various crochet machine or warp knitting machine. TABLE 2 outlines the fabric widths that may be achieved using different numbers of needles on different gauge machines. It is understood that the dimensions in TABLE 1 are approximate due to the shrink factor which depends on stitch design, stitch density, and yarn size used.

TABLE 1

| Gauge | Needle Count | Knitting Width |
| --- | --- | --- |
| 48 | 2-5,656 | 0.53-2,997.68 mm |
| 24 | 2-2,826 | 1.06-2,995.56 mm |
| 20 | 2-2,358 | 1.27-2,994.66 mm |
| 18 | 2-2,123 | 1.41-2,993.43 mm |
| 16 | 2-1,882 | 1.59-2,992.38 mm |
| 14 | 2-1,653 | 1.81-2,991.93 mm |
| 12 | 2-1,411 | 2.12-2,991.32 mm |
| 10 | 2-1,177 | 2.54-2,989.58 mm |
| 5 | 2-586 | 5.08-2,976.88 mm |

Embodiments of a prosthetic device according to the present invention may be knitted on a fine gauge crochet knitting machine. A non-limiting list of crochet machines capable of manufacturing the surgical mesh according to aspects of the present invention are provided by: Changde Textile Machinery Co., Ltd.; Gomez; China Textile Machinery Co., Ltd.; Huibang Machine; Jakob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Embodiments of a prosthetic device according to the present invention may be knitted on a fine gauge warp knitting machine. A non-limiting list of warp knitting machines capable of manufacturing the surgical mesh according to aspects of the present invention are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of a prosthetic device according to the present invention may be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger; Machinery; Fujian Hongqi; G & P Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

Figure 1B:
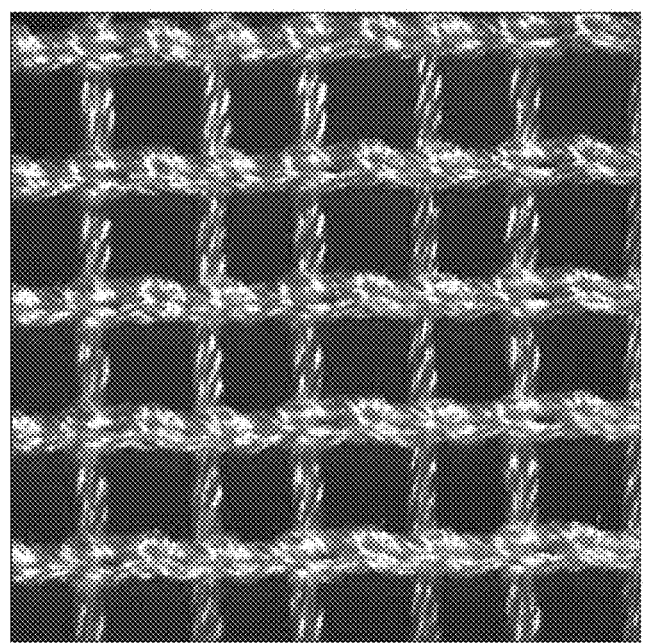
FIG. 1B illustrates the technical front of the example mesh illustrated in FIG. 1A.

FIGS. 1-20 illustrate an example meshes produced according to aspects of the present invention. Referring to FIGS. 1A and B, an example mesh 100 is produced on a single needle bed warp knitting machine according to aspects of the present invention. FIG. 1A shows the technical back 100A of the mesh 100, and FIG. 1B shows the technical front 100B of the mesh 100.

Figure 2A:
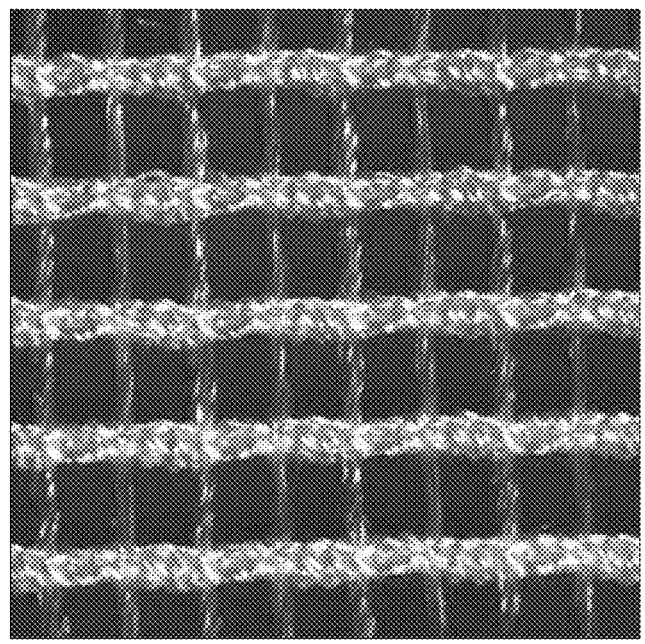
FIG. 2A shows the technical front 200A of the mesh 200 embodiment of the present invention.
Figure 2B:
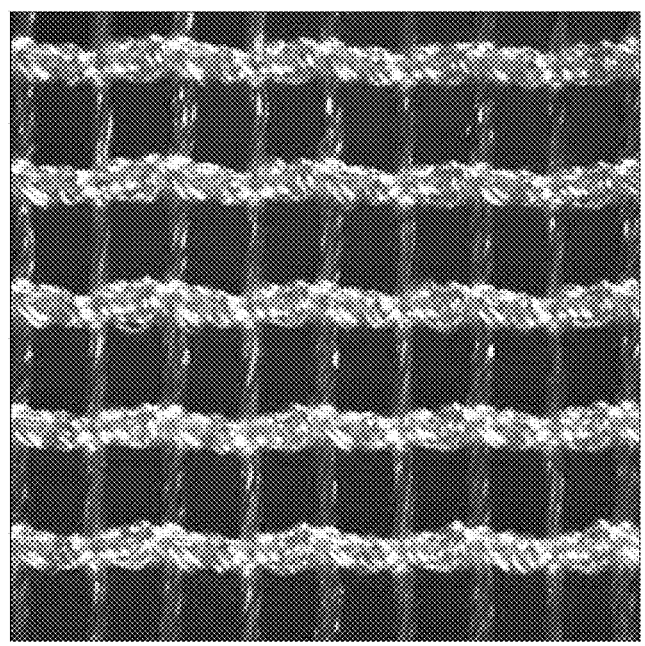
FIG. 2B shows the technical back 200B of the mesh 200 embodiment of the present invention.

Referring to FIGS. 2A and B, an example mesh 200 is produced on a double needle bed warp knitting machine according to aspects of the present invention. FIG. 2A shows the technical front 200A of the mesh 200, and FIG. 2B shows the technical back 200B of the mesh 200.

Figure 3:
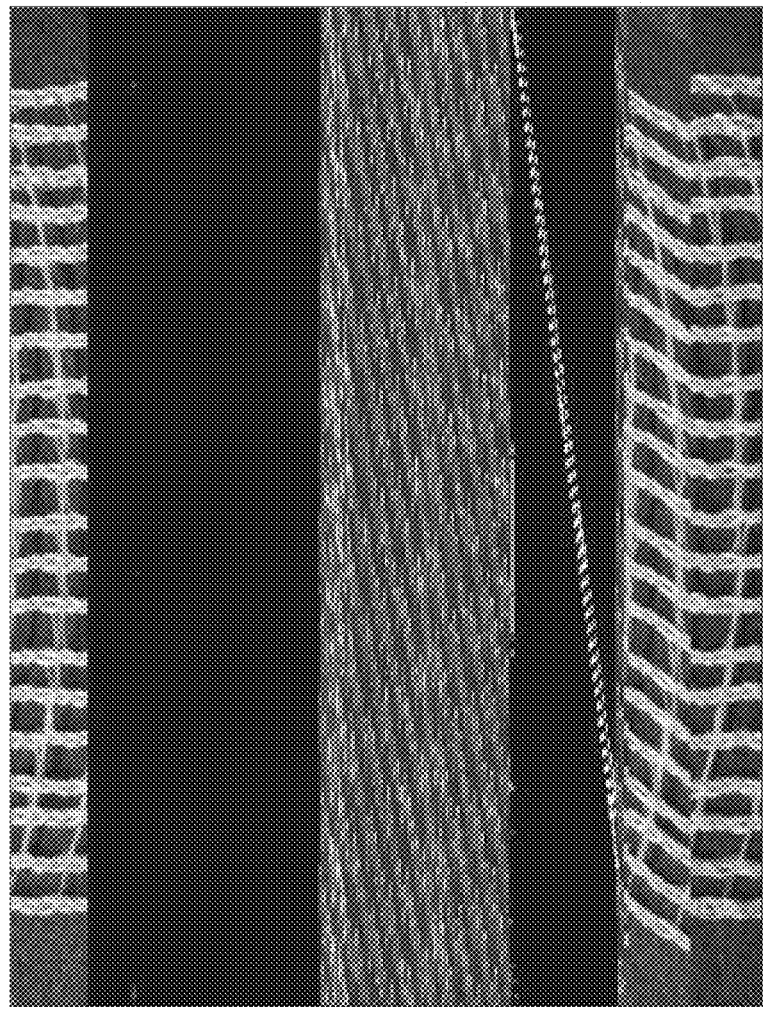
FIG. 3 illustrates an example mesh produced with single filament silk yarn according to aspects of the present invention.

FIG. 3 illustrates an example mesh 300 produced with single filament silk yarn according to aspects of the present invention.

Figure 4:
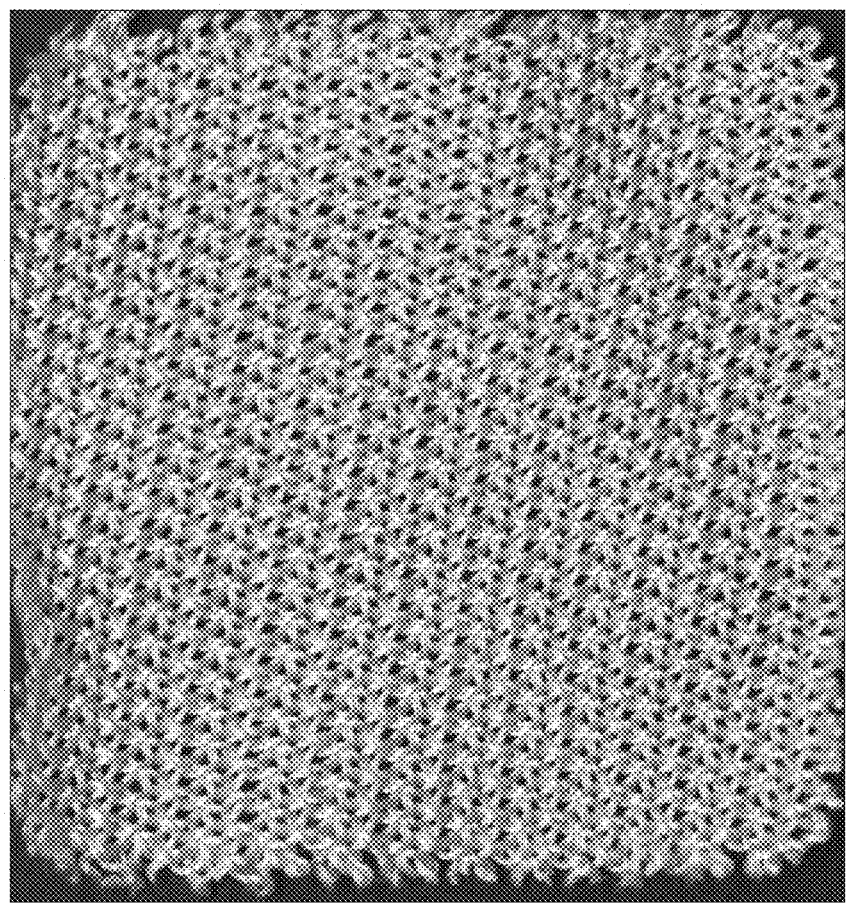
FIG. 4 illustrates an example mesh produced on a single needle bed warp knitting machine according to aspects of the present invention.

FIG. 4 shows an example mesh 400 produced on a single needle bed warp knitting machine according to aspects of the present invention.

Figure 5B:
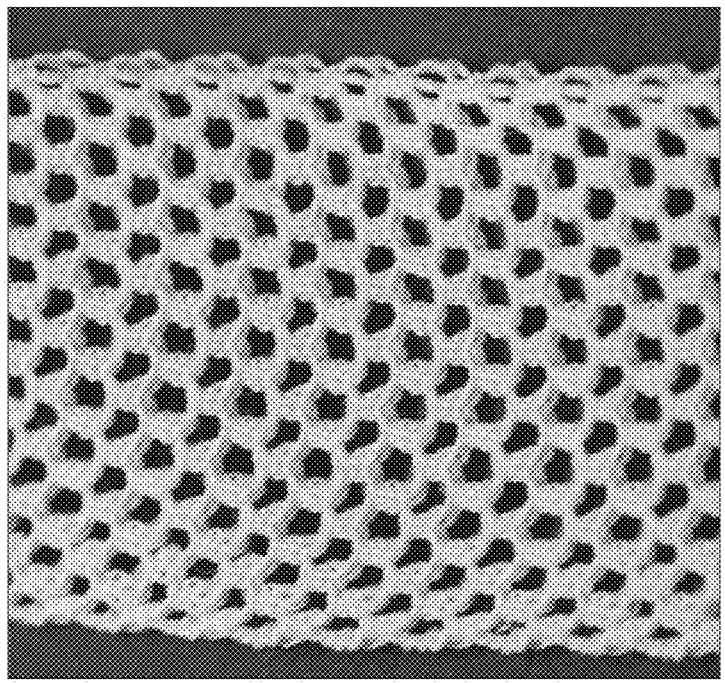
FIG. 5B illustrates an example mesh produced on a double needle bed warp knitting machine, the example mesh having a hexagonal pore according to aspects of the present invention.
Figure 5A:
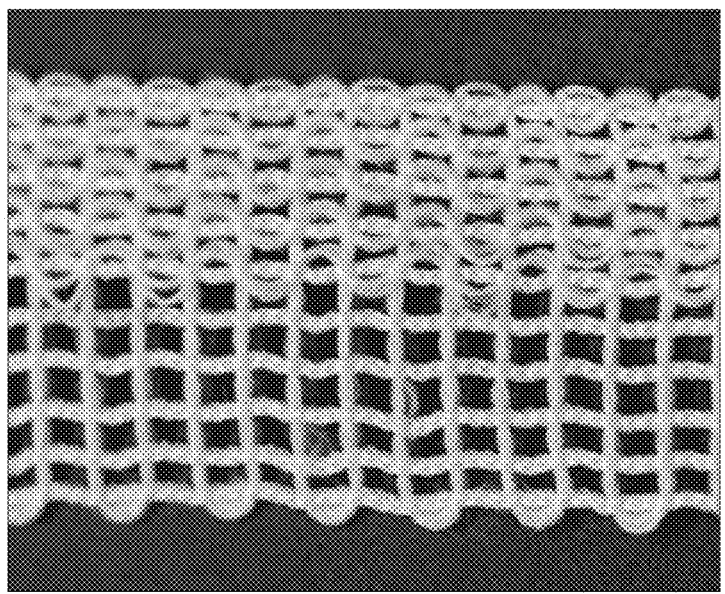
FIG. 5A illustrates an example mesh produced on a double needle bed warp knitting machine, the example mesh having a parallelepiped pore with a section demonstrating a plush design according to aspects of the present invention.

FIG. 5A illustrates an example mesh 500A produced on a double needle bed warp knitting machine. The mesh 500A has a parallelepiped pore with a section demonstrating a plush design according to aspects of the present invention. Meanwhile, FIG. 5B illustrates an example mesh 500B produced on a double needle bed warp knitting machine. The example mesh 500B has a hexagonal pore according to aspects of the present invention.

Figure 6B:
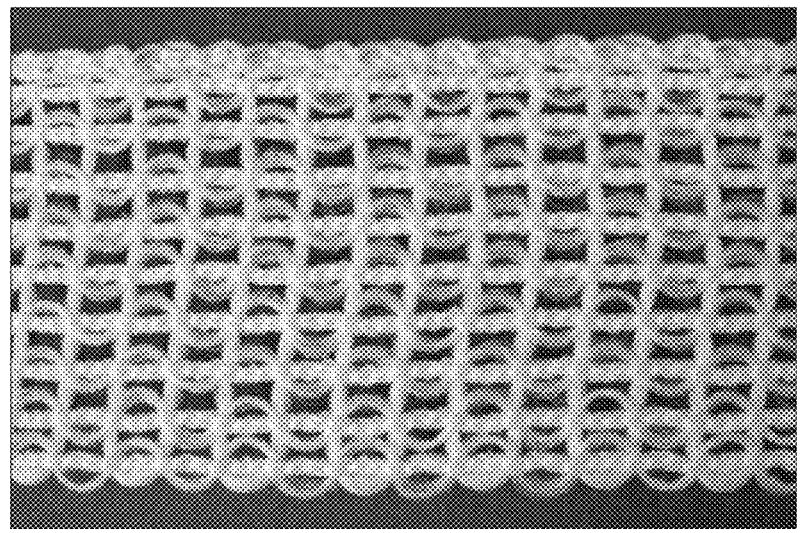
FIG. 6 illustrates an example narrow mesh fabrics of varying stitch densities incorporating a plush variation according to aspects of the present invention. Thus, FIGS. 6A and B illustrate an example narrow mesh fabrics 600A and 600B according to aspects of the present invention.
Figure 6A:
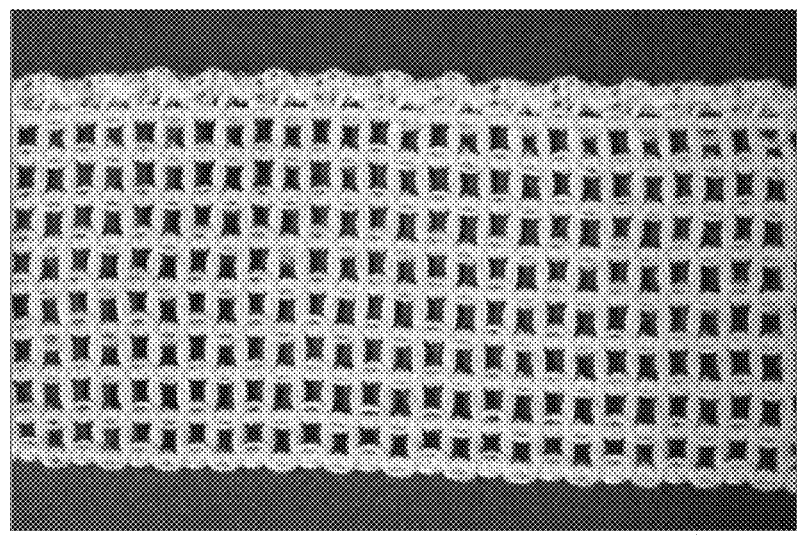

FIGS. 6A and B illustrate an example narrow mesh fabrics 600A and 600B according to aspects of the present invention. The mesh fabrics 600A and 600B have varying stitch densities incorporating a plush variation.

Figure 7:
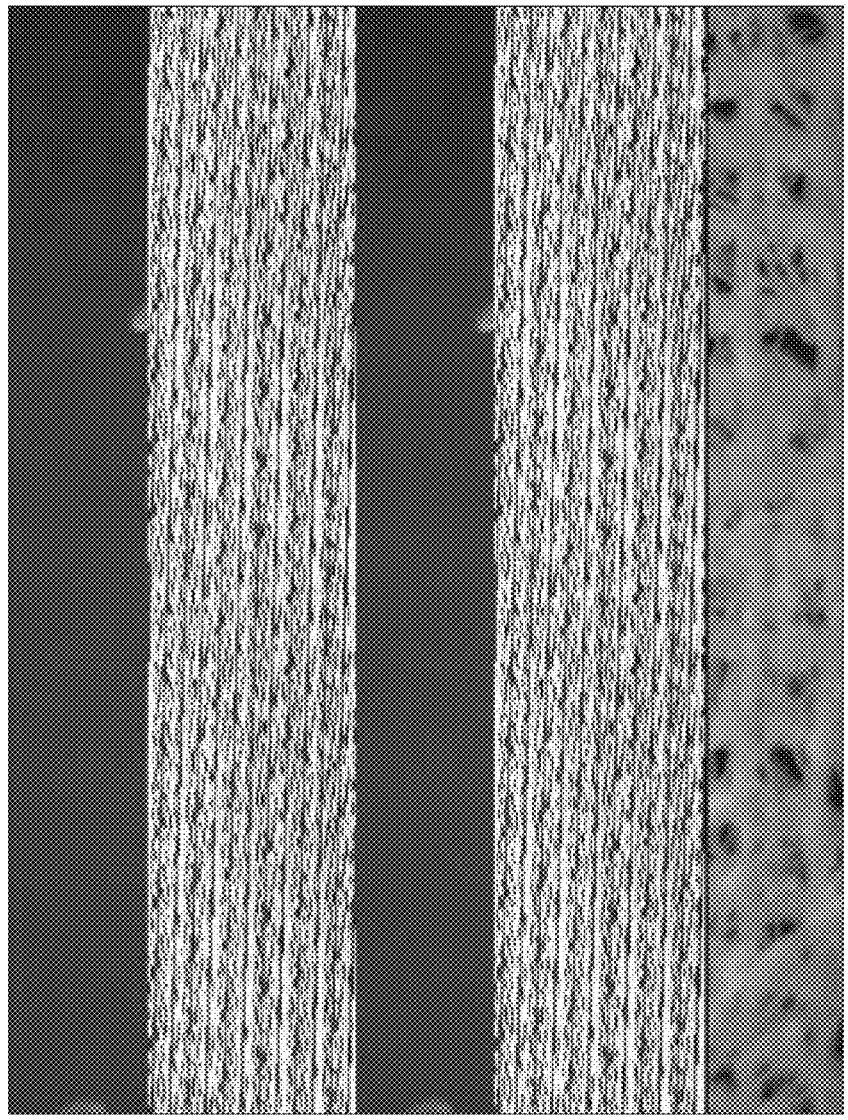
FIG. 7 illustrates an example mesh incorporating loop pile according to aspects of the present invention.
Figure 8:
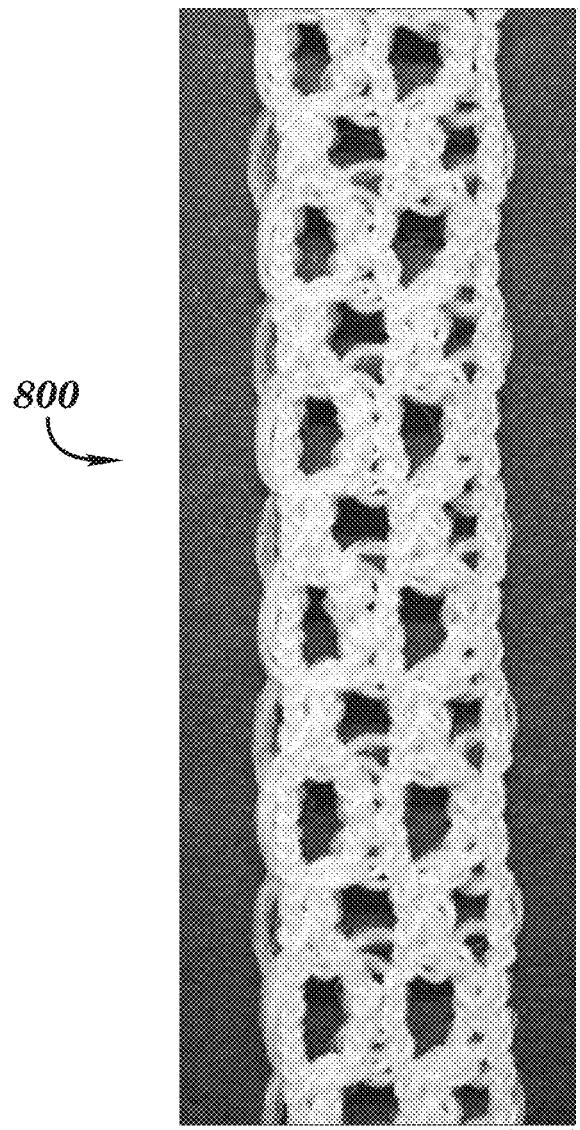
FIG. 8 illustrates an example narrow mesh fabric with pore design achieved through variation in the yarn feed rate according to aspects of the present invention.

Referring to FIG. 7, an example mesh 700 incorporates loop pile according to aspects of the present invention. FIG. 8 illustrates an example narrow mesh fabric 800 with pore design achieved through variation in the yarn feed rate according to aspects of the present invention.

Figure 9B:
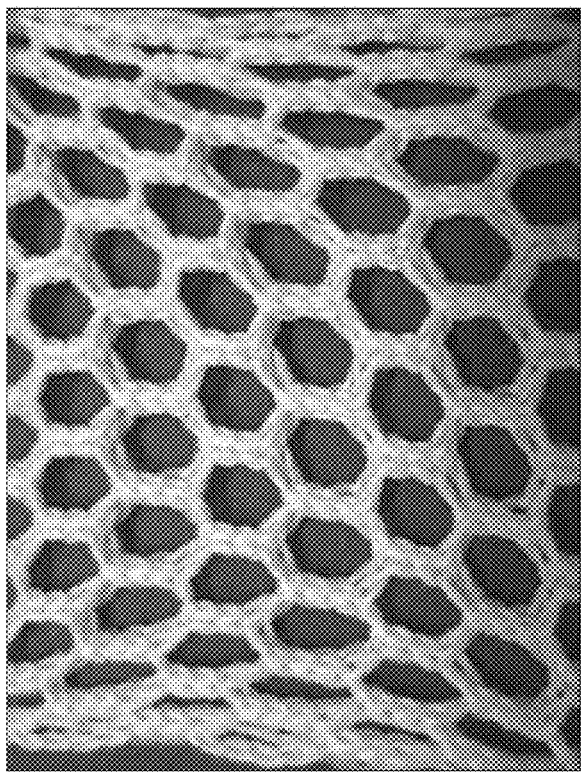
FIG. 9B illustrates an example opened mesh fabric with hexagonal shaped pores according to aspects of the present invention.
Figure 9A:
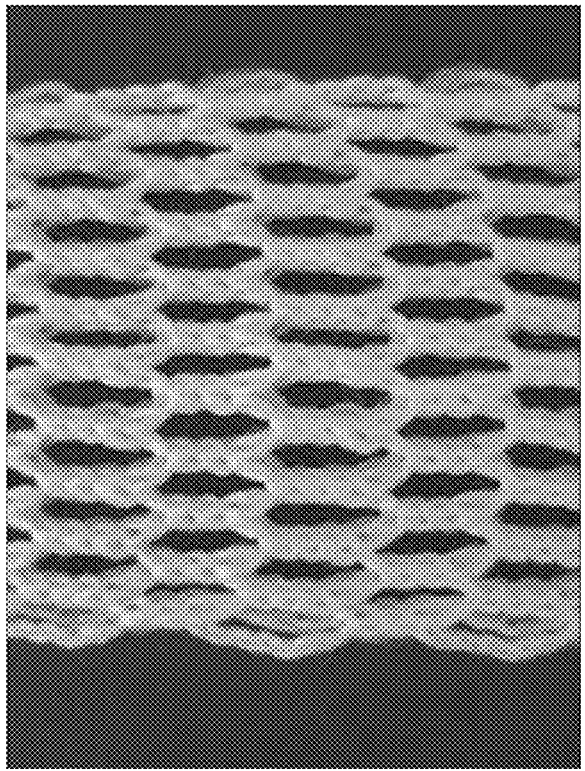
FIG. 9A illustrates an example collapsed mesh fabric with hexagonal shaped pores according to aspects of the present invention.

FIG. 9A illustrates an example collapsed mesh fabric 900A with hexagonal-shaped pores according to aspects of the present invention. Meanwhile, FIG. 9B illustrates an example opened mesh fabric 900B with hexagonal shaped pores according to aspects of the present invention.

Figure 10:
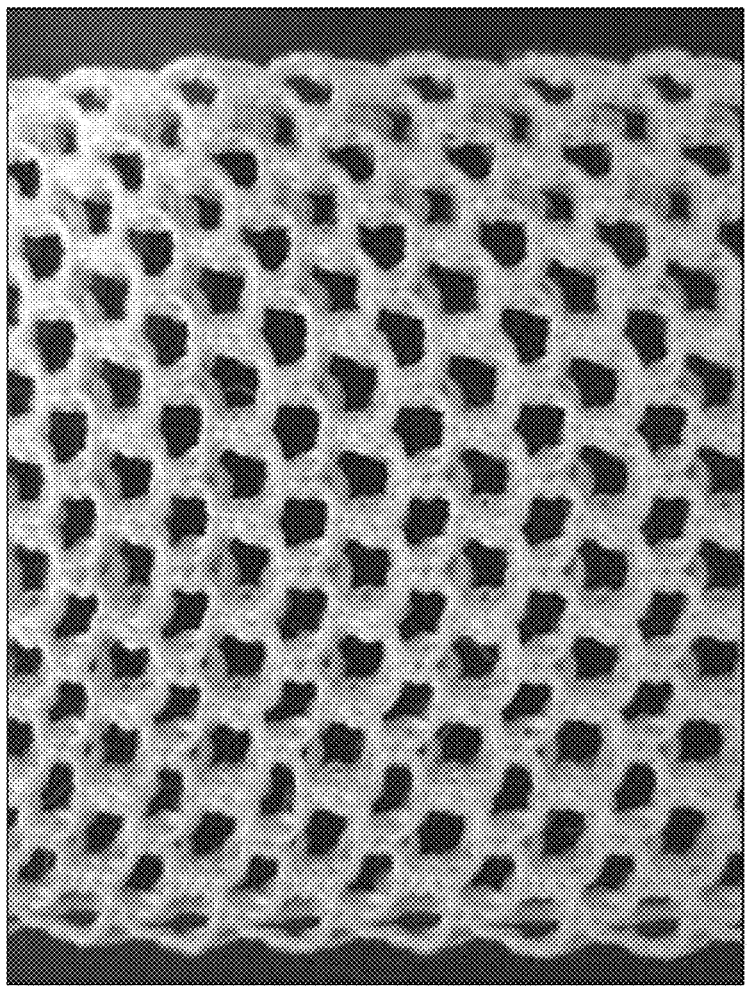
FIG. 10 illustrates an example of a stable, non-collapsible, hexagonal-shaped porous mesh fabric according to aspects of the present invention.

As shown in FIG. 10, an example of a stable, non-collapsible mesh fabric 1000 includes hexagonal-shaped pores according to aspects of the present invention.

Figure 11B:
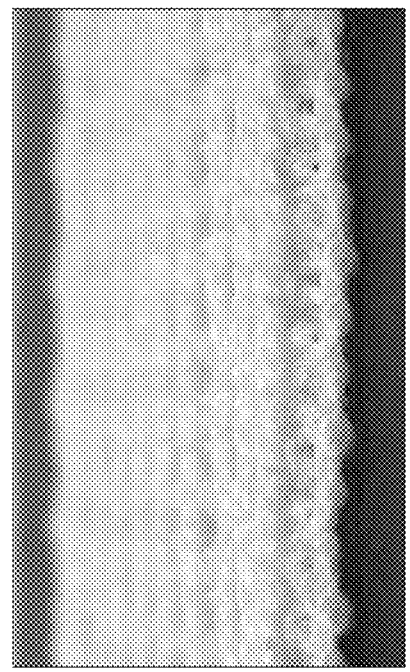
FIG. 11B illustrates the 2.55 mm thickness of the example three-dimensional mesh of FIG. 11A.
Figure 11A:
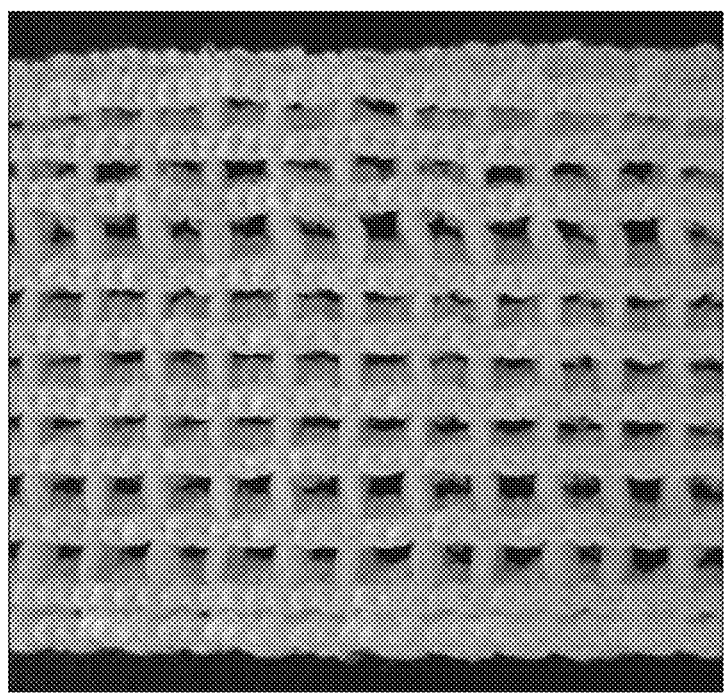
FIG. 11A illustrates an example of a three-dimensional mesh with the same technical front and technical back according to aspects of the present invention.
Figure 12:
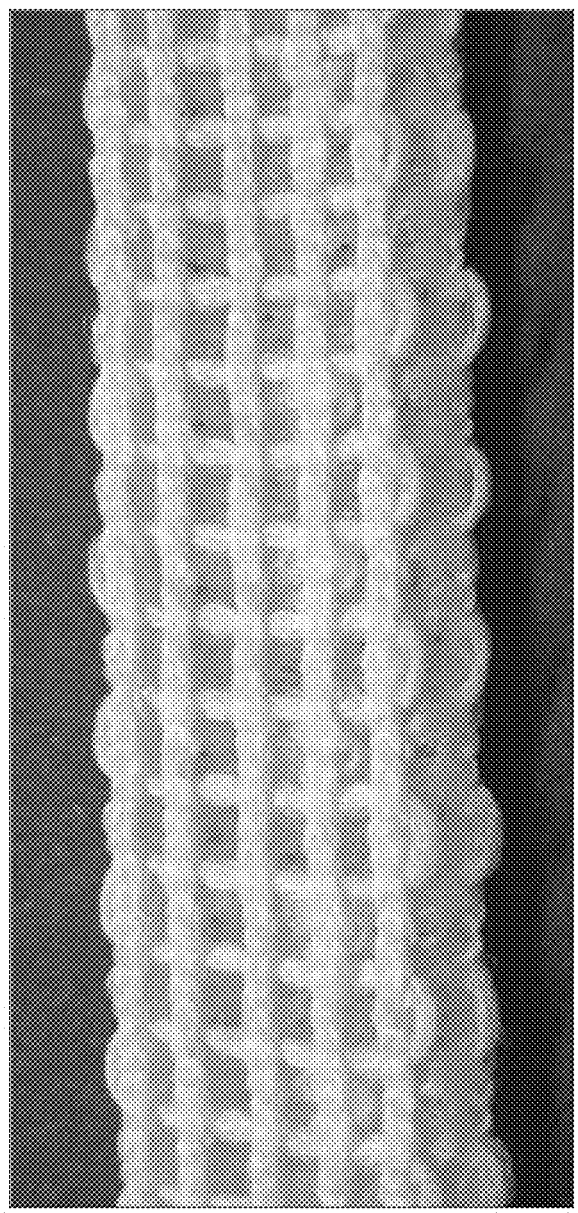
FIG. 12 illustrates an example of a three-dimensional mesh with a thickness of 3.28 mm according to aspects of the present invention.

FIG. 11A illustrate an example three-dimensional mesh 1100 with the same technical front and technical back according to aspects of the present invention. FIG. 11B illustrates the 2.55 mm thickness of the three-dimensional mesh 1100. FIG. 12 illustrates another example three-dimensional mesh 1200 with a thickness of 3.28 mm according to aspects of the present invention.

Figure 13A:
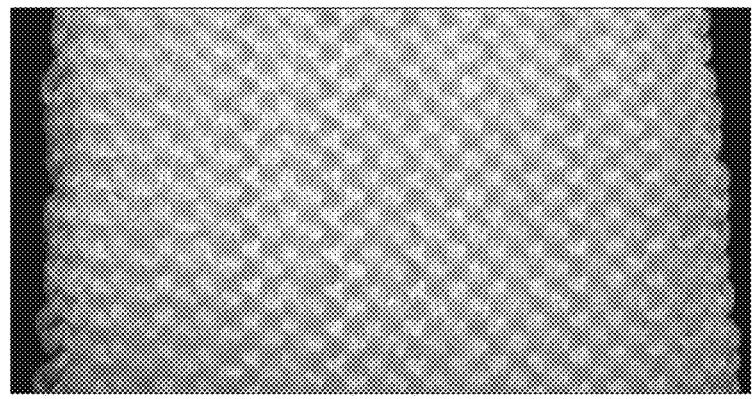
FIG. 13A illustrates the technical front of an example non-porous mesh according to aspects of the present invention.
Figure 13B:
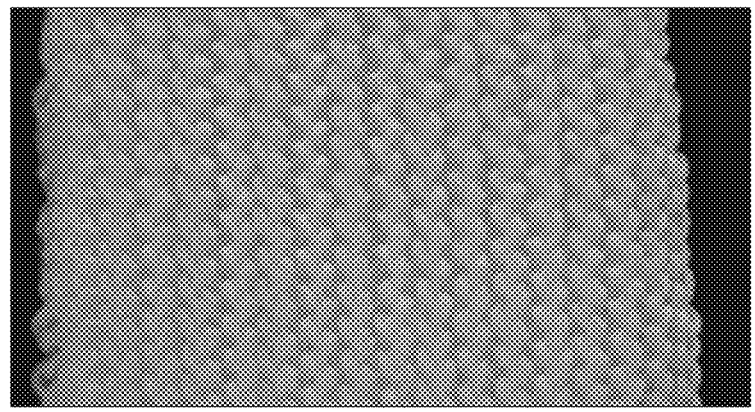
FIG. 13B illustrates the technical back of the example non-porous mesh of FIG. 13A.
Figure 13C:
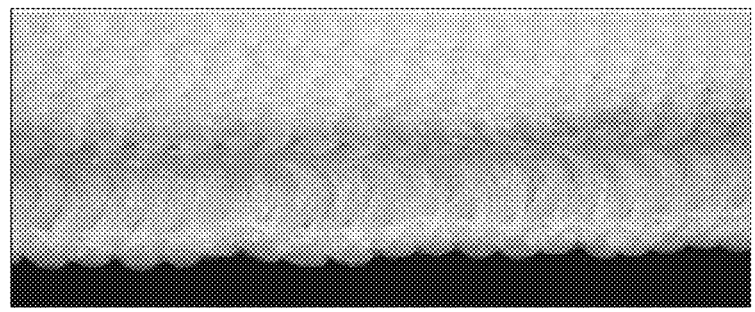
FIG. 13C illustrates the 5.87 mm thickness of the example non-porous mesh of FIG. 13A.

FIGS. 13A-C illustrate an example non-porous mesh 1300 according to aspects of the present invention. FIG. 13A shows the technical front 1300A of the non-porous mesh 1300. FIG. 13B shows the technical back 1300B of the non-porous mesh 1300. FIG. 13C shows that non-porous mesh 1300 has a thickness of 5.87 mm.

Figure 14B:
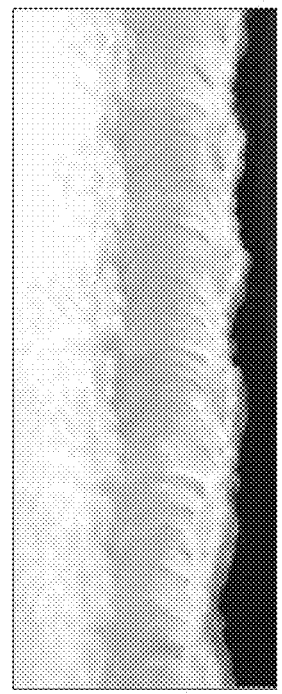
FIG. 14B illustrates the 5.36 mm thickness of the example three-dimensional mesh of FIG. 14A.
Figure 14A:
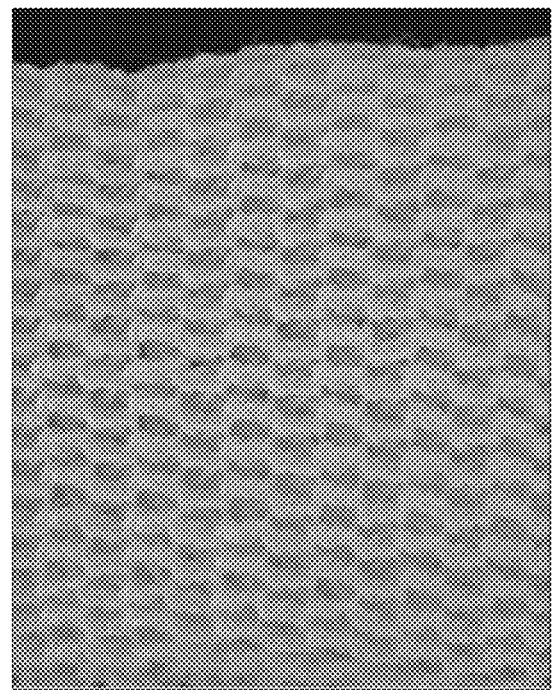
FIG. 14A illustrates an example of a three-dimensional mesh with the same technical front and technical back according to aspects of the present invention.
Figure 15B:
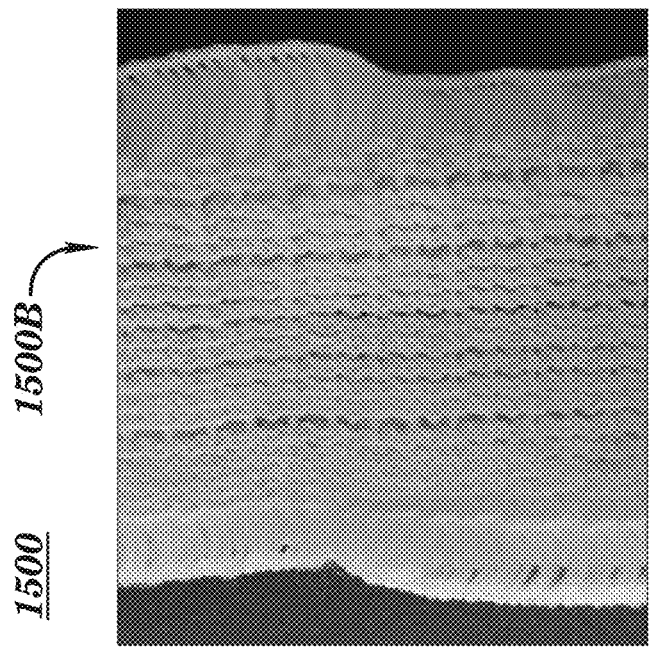
FIG. 15B illustrates the technical back of the example three-dimensional mesh fabric of FIG. 15A.
Figure 15A:
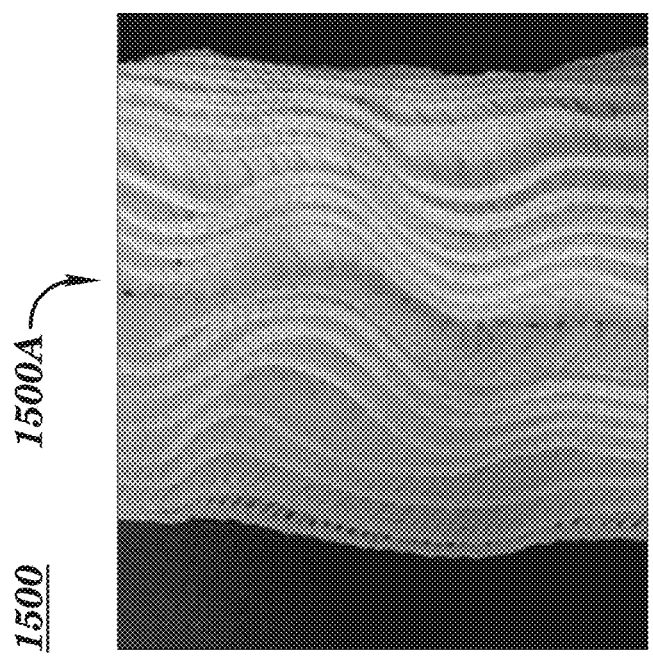
FIG. 15A illustrates the technical front of an example three-dimensional mesh fabric according to aspects of the present invention.
Figure 16:
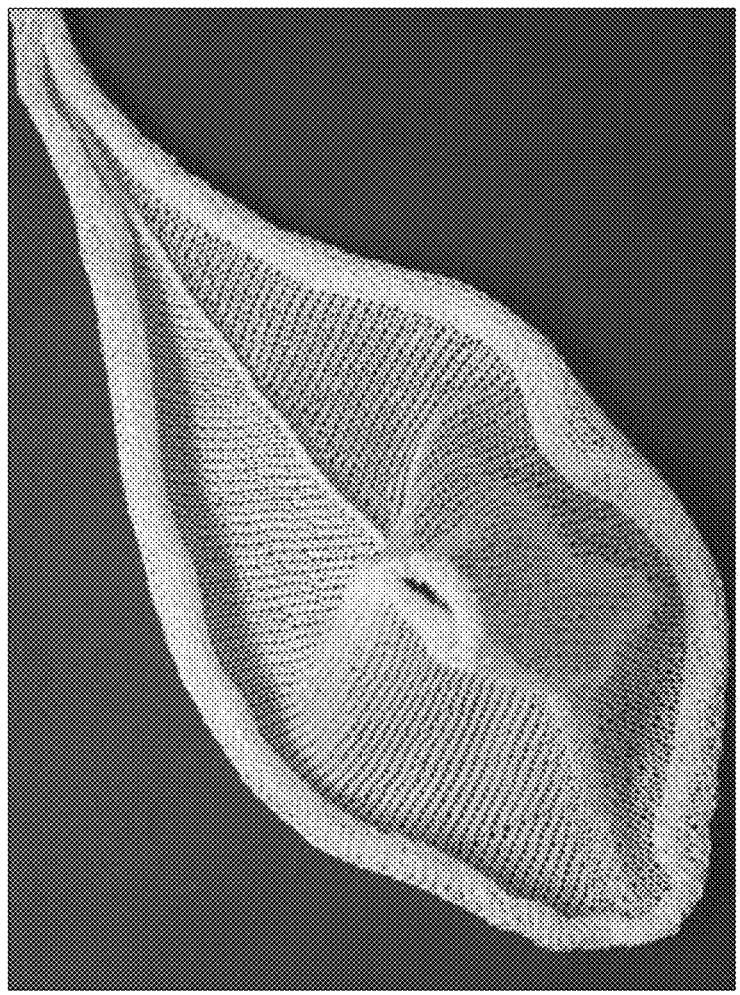
FIG. 16 illustrates an example mesh produced on a double needle bed weft knitting machine demonstrating shaping of the mesh for a breast support application according to aspects of the present invention.
Figure 17:
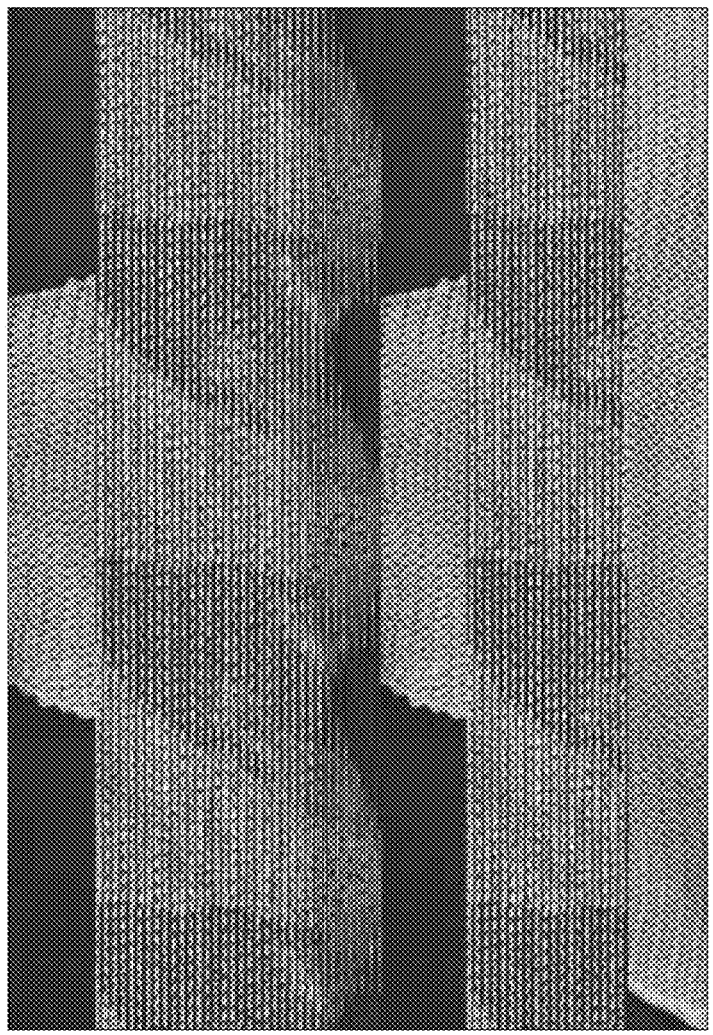
FIG. 17 illustrates another example mesh produced on a double needle bed weft knitting machine demonstrating shaping of the mesh for a breast support application according to aspects of the present invention.
Figure 18:
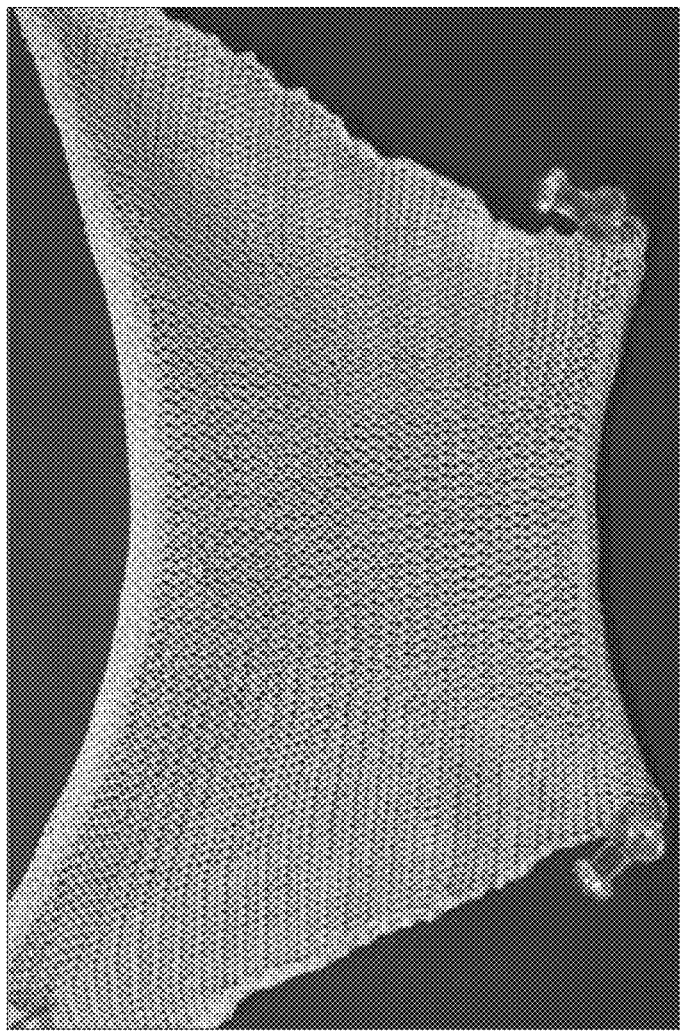
FIG. 18 illustrates yet another example mesh produced on a double needle bed weft knitting machine demonstrating shaping of the mesh for a breast support application according to aspects of the present invention.
Figure 19:
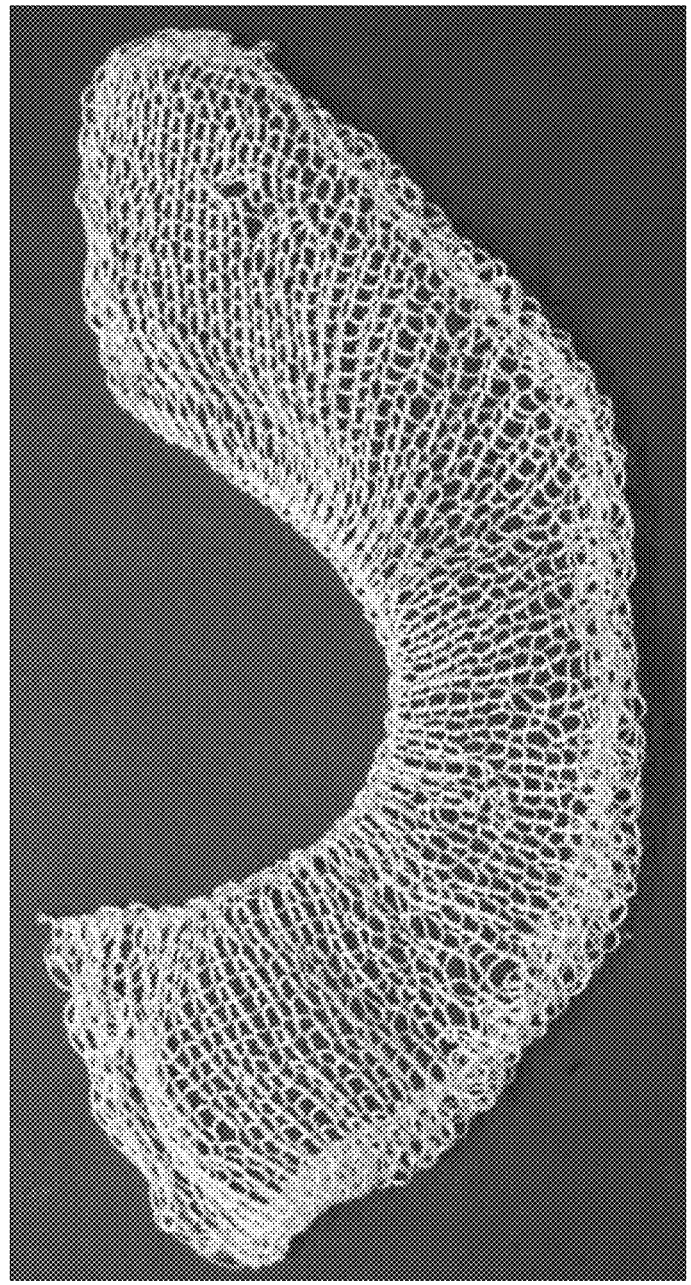
FIG. 19 illustrates a further mesh produced on a double needle bed weft knitting machine demonstrating shaping of the mesh for a breast support application according to aspects of the present invention.
Figure 20:
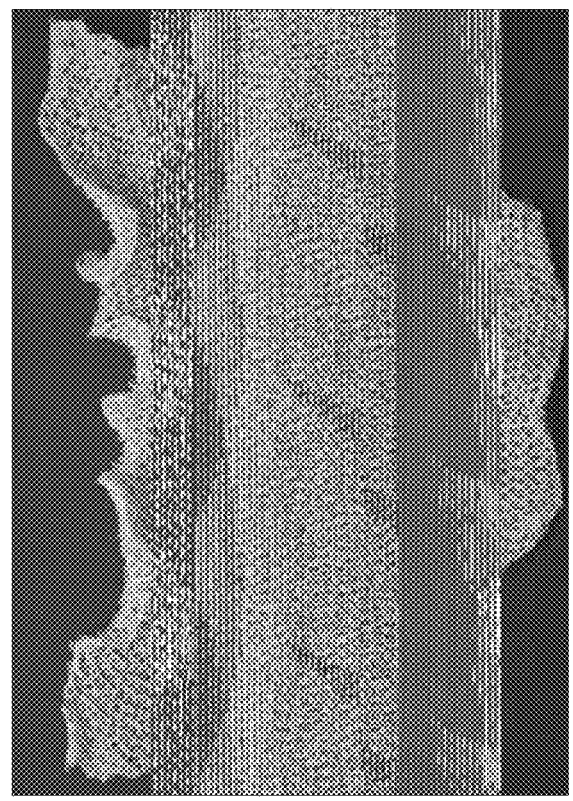
FIG. 20 illustrates another example mesh produced on a double needle bed weft knitting machine demonstrating shaping of the mesh for a breast support application according to aspects of the present invention.

FIG. 14A illustrates an example three-dimensional mesh 1400 with the same technical front and technical back according to aspects of the present invention. FIG. 14B shows that the three-dimensional mesh 1400 has a thickness of approximately 5.36 mm. FIGS. 15A and B illustrate another example three-dimensional mesh fabric 1500 according to aspects of the present invention. FIG. 15A shows the technical front 1500A of the fabric 1500, and FIG. 15B illustrates the technical back 1500B of the fabric 1500.

FIGS. 16-20 illustrate respective example meshes 1600, 1700, 1800, 1900, and 2000 that are produced on a double needle bed weft knitting machine. The meshes 1600, 1700, 1800, 1900, and 2000 demonstrate shaping of a mesh for a breast support application according to aspects of the present invention.

A test method was developed to check the cutability of the surgical mesh formed according to aspects of the present invention. In the test method, the surgical mesh evaluated according to the number of were needed to cut the mesh with surgical scissors. The mesh was found to cut excellently because it took one scissor stroke to cut through it. The mesh was also cut diagonally and in circular patterns to determine how easily the mesh unraveled and how much it unraveled once cut. The mesh did not unravel more than one mode after being cut in both directions. To determine further if the mesh would unravel, a suture, was passed through the closest pore from the cut edge, and pulled. This manipulation did not unravel the mesh. Thus, the surgical mesh is easy to cut and does not unravel after manipulation.

Embodiments may be processed with a surface treatment, which increases material hydrophilicity, biocompatibility, physical, and mechanical properties such as handling for ease of cutting and graft pull-through, as well as anti-microbial and anti-fungal coatings. Specific examples of surface treatments include, but are not limited to:

plasma modification
protein such as but not limited to fibronectin, denatured collagen or gelatin, collagen gels and hydrophobin by covalent link or other chemical or physical method
peptides with hydrophilic and a hydrophobic end
peptides contain one silk-binding sequence and one biologically active sequence—biodegradable cellulose
surface sulfonation
ozone gas treatment
physically bound and chemically stabilized peptides
DNA/RNA aptamers
Peptide Nucleic Acids
Avimers
modified and unmodified polysaccharide coatings
carbohydrate coating
anti-microbial coatings
anti-fungal coatings
phosphorylcholine coatings A method to evaluate the ease of delivery through a cannula was done to make sure the surgical mesh could be used laparoscopically. Various lengths were rolled up and pushed through two different standard sized cannulas using surgical graspers. The mesh was then evaluated to determine if there was any damage done to the mesh. The mesh that was put through the cannulas was found to have slight distortion to the corner that was held by the grasper. The 16 cm and 18 cm lengths of mesh that were rolled up and pushed through the 8 mm cannula had minimal fraying and one distorted pore, respectively. It was also found that no damage was done to the cannula or septum in any of the tests. It was found that appropriately sized surgical mesh will successfully pass through a laparoscopic cannula without damage, enabling its effective use during laparoscopic procedures.

A surgical mesh device according to aspects of the present invention has been found to bio-resorb by 50% in approximately 100 days. In a study by Horan et al., Sprague-Dawley rats were used to compare the bio-resorption of embodiments according to the present invention to Mersilene™ mesh (Ethicon, Somerville, N.J.). The histology reports from the article state that after 94 days, 43% of the initial mesh of the embodiments remained compared to 96% of the Mersilene™ mesh. It was also reported that the in growth was more uniform with the mesh of embodiments than the Mersilene™ mesh. The Mersilene™ was found to have less in growth in the defect region than along the abdominal wall.

Physical properties include thickness, density and pore sizes. The thickness was measured utilizing a J100 Kafer Dial Thickness Gauge. A Mitutoyo Digimatic Caliper was used to find the length and width of the samples; used to calculate the density. The density was found by multiplying the length, width and thickness of the mesh then dividing the resulting value by the mass. The pore size was found by photographing the mesh with an Olympus SZX7 Dissection Microscope under 0.8× magnification. The measurements were taken using ImagePro 5.1 software and the values were averaged over several measurements. The physical characteristics of the sample meshes, including embodiments according to the present invention, are provided in TABLE 2.

TABLE 2

| | Physical Characterization | | |
| --- | --- | --- | --- |
| Device | Thickness (mm) | Pore Size (mm$^2$) | Density (g/cm$^3$) |
| Mersilene Mesh | 0.31 ± 0.01 | 0.506 ± 0.035 | 0.143 ± 0.003 |
| Bard Mesh | 0.72 ± 0.00 | 0.465 ± 0.029 | 0.130 ± 0.005 |
| Vicryl Knitted Mesh | 0.22 ± 0.01 | 0.064 ± 0.017 | 0.253 ± 0.014 |
| Present Embodiments - Single Needle Bed (SB) | 1.0 ± 0.04 | 0.640 ± 0.409 | 0.176 ± 0.002 |
| Present Embodiments - Double Needle Bed (DB) | 0.80 ± 0.20 | 1.27 | 0.135 – 0.165 |

All devices were cut to the dimensions specified in TABLE 3, for each type of mechanical analysis. Samples were incubated in phosphate buffered saline (PBS) for 3±1.25 hours at 37±2° C. prior to mechanical analysis to provide characteristics in a wet environment. Samples were removed from solution and immediately tested.

TABLE 3

| Test Modality | Length (mm) | Width (mm) |
| --- | --- | --- |
| Tensile | 60 | 10 |
| Burst | 32 | 32 |
| Suture Pull-Out | 40 | 20 |
| Tear | 60 | 40 |
| Tensile Fatigue | 60 | 40 |

Ball burst test samples were scaled down due to limitations in material dimensions. The test fixture employed was a scaled (1:2.5) version of that recommended by ASTM Standard D3787. The samples were centered within a fixture and burst with a 10 mm diameter ball traveling at a displacement rate of 60 mm/min. Maximum stress and stiffness were determined from the burst test. Results can be seen in TABLE 4.

TABLE 4

| | Burst Strength | |
| --- | --- | --- |
| Device | Stress (MPa) | Stiffness (N/mm) |
| Mersilene Mesh | 0.27 ± 0.01 | 13.36 ± 0.85 |
| Bard Mesh | 0.98 ± 0.04 | 38.28 ± 1.49 |
| Vicryl Knitted Mesh | 0.59 ± 0.05 | 32.27 ± 1.86 |
| Pelvitex Polypropylene Mesh | 0.59 ± 0.04 | 29.78 ± 1.33 |
| Permacol Biologic Implant | 1.27 ± 0.27 | 128.38 ± 22.14 |
| Present Embodiments (SB) | 0.76 ± 0.04 | 46.10 ± 2.16 |
| Present Embodiments (DB) | 0.66 | 40.9 |

Tensile tests were performed along the fabric formation and width axes of each device. A 1 cm length of mesh on each end of the device was sandwiched between pieces of 3.0 mm thick silicone sheet and mounted in pneumatic fabric clamps with a clamping pressure of 70-85 psi. Samples were loaded through displacement controlled testing at a strain rate of 100%/s (2400 mm/min) and or and/or 67%/s (1600 mm/min) until failure. The ultimate tensile strength (UTS), linear stiffness and percent elongation at break can be seen in the following tables. Results can be found in TABLES 5-8. An entry of "NT" indicates that the data has not yet been tested.

TABLE 5

| | Tensile SPTF (Fabric Formation Axis-1600 mm/min) | | | |
| --- | --- | --- | --- | --- |
| Device | Strength (N) | Stress (MPa) | Stiffness (N/mm) | % Elong. @ Break |
| Mersilene Mesh | 46.14 ± 3.15 | 10.04 ± 0.71 | 0.90 ± 0.06 | 132.1% ± 9.3% |
| Bard Mesh | 30.90 ± 2.0 | 16.64 ± 1.16 | 3.32 ± 0.26 | 106.5% ± 3.2% |
| Vicryl Knitted Mesh | 35.69 ± 3.30 | 35.89 ± 4.48 | 2.59 ± 0.33 | 89.0% ± 7.3% |
| Present Embodiments (SB) | 76.72 ± 4.36 | 10.06 ± 0.38 | 7.13 ± 0.50 | 41.5% ± 2.3% |
| Present Embodiments Mesh (DB) | NT | NT | NT | NT |

TABLE 6

| | Tensile SPTF (Fabric Formation Axis-2400 mm/min) | | | |
| --- | --- | --- | --- | --- |
| Device | Strength (N) | Stress (MPa) | Stiffness (N/mm) | % Elong. @ Break |
| Mersilene Mesh | 43.87 ± 5.19 | 14.15 ± 1.68 | 2.18 ± 0.3 | 56.6% ± 3.5% |
| Bard Mesh | 35.29 ± 5.69 | 4.90 ± 0.79 | 0.80 ± 0.23 | 177.3% ± 13.2% |
| Vicryl Knitted Mesh | 30.88 ± 3.30 | 14.04 ± 1.50 | 0.76 ± 0.17 | 191.9% ± 14.2% |
| Pelvite Polypropylene Mesh | 23.05 ± 3.75 | 5.36 ± 0.87 | 0.57 ± 0.07 | 110.0% ± 13.6% |
| Permacol Biologic Implant | 164.52 ± 30.58 | 13.71 ± 2.55 | 23.94 ± 2.7 | 23.5% ± 3.3% |
| Present Embodiments (SB) | 72.31 ± 7.80 | 6.95 ± 0.75 | 4.31 ± 0.3 | 45.5% ± 5.2% |
| Present Embodiments (DB) | 74.62 ± 2.70 | 8.68 ± 0.31 | 4.25 ± 0.13 | 48.3% ± 2.1% |

TABLE 7

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 31.14 ± 2.21 | 10.04 ± 0.71 | 0.90 ± 0.06 | 132.1% ± 9.3% |
| Bard Mesh | 119.80 ± 8.36 | 16.64 ± 1.16 | 3.32 ± 0.26 | 106.5% ± 3.2% |
| Vicryl Knitted Mesh | 78.96 ± 9.86 | 35.89 ± 4.48 | 2.59 ± 0.33 | 89.0% ± 7.3% |
| Present Embodiments (SB) | 104.58 ± 3.96 | 10.06 ± 0.38 | 7.13 ± 0.50 | 41.5% ± 2.3% |
| Present Embodiments (DB) | NT | NT | NT | NT |

TABLE 8

Tensile SPTF (Fabric Width Axis-2400 mm/min)

| Device | Strength (N) | Stress (MPa) | Stiffness (N/mm) | % Elong. @ Break |
|---|---|---|---|---|
| Mersilene Mesh | 28.11 ± 2.93 | 28.11 ± 2.93 | 1.05 ± 0.13 | 128.2% ± 23.6% |
| Bard Mesh | 103.53 ± 8.92 | 14.38 ± 1.24 | 3.43 ± 0.5 | 94.0% ± 8.4% |
| Vicryl Knitted Mesh | 106.65 ± 8.46 | 48.48 ± 3.85 | 5.08 ± 0.1 | 58.6% ± 8.4% |
| Pelvite Polypropylene Mesh | 30.24 ± 5.77 | 7.03 ± 1.34 | 1.48 ± 0.1 | 89.6% ± 9.6% |
| Permacol Biologic Implant | 67.71 ± 13.36 | 5.64 ± 1.11 | 8.56 ± 2.0 | 27.4% ± 4.2% |
| Present Embodiments (SB) | 98.84 ± 4.79 | 9.50 ± 0.46 | 8.48 ± 0.3 | 39.0% ± 4.1% |
| Present Embodiments (DB) | 70.08 ± 2.55 | 8.15 ± 0.30 | 5.87 ± 0.22 | 33.6% ± 2.0% |

Tear Strength was found through a method that entailed cutting a 10 mm "tear" into the edge, perpendicular to the long axis edge and centered along the length of the mesh. The mesh was mounted in pneumatic fabric clamps as previously described in the tensile testing methods. Samples were loaded through displacement controlled testing at a strain rate of 100%/s (2400 mm/min) until failure. The load at failure and the mode of failure are shown in TABLE 9.

TABLE 9

Tear Strength

| Device | Strength (N) | Failure Mode |
|---|---|---|
| Mersilene Mesh | 110.30 ± 5.63 | Tear Failure: 6/6 |
| Bard Mesh | 181.70 ± 12.33 | Tear Failure: 6/6 |
| Vicryl Knitted Mesh | 109.35 ± 4.85 | Tear Failure: 6/6 |
| Pelvitex Polypropylene Mesh | 108.14 ± 6.95 | Tear Failure: 4/6 |
| Permacol Biologic Implant | 273.79 ± 65.57 | Tear Failure: 6/6 |
| Embodiments (SB) | 194.81 ± 9.12 | Tear Failure: 6/6 |
| Embodiments (DB) | NT | NT |

Tensile fatigue testing was performed on the surgical mesh device according to aspects of the present invention and representative predicate types including Vicryl Mesh and Bard Mesh. Samples were loaded into the pneumatic fabric clamps as previously described in the tensile testing methods above. Samples were submerged in PBS at room temperature during cycling. Sinusoidal load controlled cycling was performed to 60% of mesh ultimate tensile strength. Number of cycles to failure was determined during the cyclic studies and can be seen in TABLE 10, where failure was indicated by fracture or permanent deformation in excess of 200%.

TABLE 10

| Device | Tensile Fatigue Cycles, 60% UTS |
|---|---|
| Bard Mesh | 6994 ± 2987 |
| Vicryl Knitted Mesh | 91 ± 127 |
| Embodiments (DB) | 1950 ± 1409 |

A method was developed to compare the suture pull out strength of the surgical mesh device according to aspects of the present invention to other surgical mesh on the market. Tested mesh was sutured with three 3.5 mm diameter suture anchors (Arthrex, Naples, Fla.) and secured to 15 pcf solid rigid polyurethane foam. Each device was positioned with the center of the 20 mm width over the center anchor with a 3 mm suture bite distance employed during suturing of the mesh to the 3 anchors. The saw bone was mounted in the lower pneumatic fabric clamp and offset to provide loading along the axis of the device when the device was centered under the load cell. The free end of the mesh was sandwiched between the silicone pieces and placed in the upper fabric clamp with 85±5 psi clamping force. Testing was performed under displacement control with a strain rate of 100%/s (1620 mm/min). Maximum load at break and failure mode can be seen in TABLE 11.

TABLE 11

Suture-Pull-Out

| Device | Strength/Suture [N] | Failure Mode |
|---|---|---|
| Mersilene Mesh | 13.50 ± 1.65 | Mesh Failure: 6 of 6 |
| Bard Mesh | 28.80 ± 3.39 | Mesh Failure: 6 of 6 |
| Vicryl Knitted Mesh | 12.90 ± 1.30 | Mesh Failure: 6 of 6 |
| Pelvitex Polyproplene Mesh | 18.29 ± 4.04 | Mesh Failure: 6 of 6 |
| Permacol Biologic Implant | 47.36 ± 7.94 | Mesh Failure: 6 of 6 |
| Embodiments (SB) | 41.00 ± 2.98 | Mesh Failure: 6 of 6 |
| Embodiments (DB) | 32.57 ± 2.30 | Mesh Failure: 6 of 6 |

By utilizing the pattern for the double needle bed mesh and modifying the yarn size, yarn feed rate and/or needle bed width, the surgical mesh device according to aspects of the present invention would meet the physical and mechanical properties necessary for a soft or hard tissue repair depending on the application. Such properties include pore size, thickness, ultimate tensile strength, stiffness, burst strength and suture pull out. The pore size could be modified dependent to the feed rate to create a more open fabric and the thickness could range from 0.40 mm up to as wide as 19.0 mm. With modifications to the pore size and thickness the UTS, stiffness, burst strength and suture pull out would all be modified as well, most likely tailoring the modifications of the pore size and/or thickness to meet certain mechanical needs.

This mesh, created on the flat knitting machine would be made in such a way to increase or decrease pore size and/or thickness by changing the yarn size and/or changing the loop length found within the knitting settings. The loop placements in combination with the node lock design allow changes to the shape and/or to the mechanical properties of the mesh. A biocompatible yarn with elasticity, such as highly twisted silk, could be used for shaping.

Figure 21A:
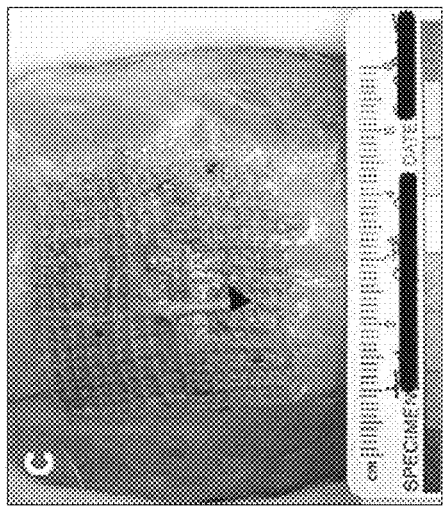
FIG. 21A illustrates a full-thickness rat abdominal defect created using a custom designed 1-cm stainless steel punch, the defect appearing oval in shape due to body wall tension applied.
Figure 21C:
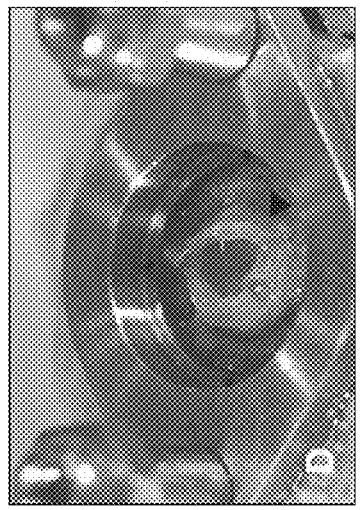
FIG. 21C illustrates an explanted specimen 94 days post implantation as shown in FIG. 21B.
Figure 21B:
FIG. 21B illustrates a 4 cm×4 cm example implant centered on top of the open defect of FIG. 21A, and held in place with single interrupted polypropylene sutures (arrow) through the implant and muscle.
Figure 21D:
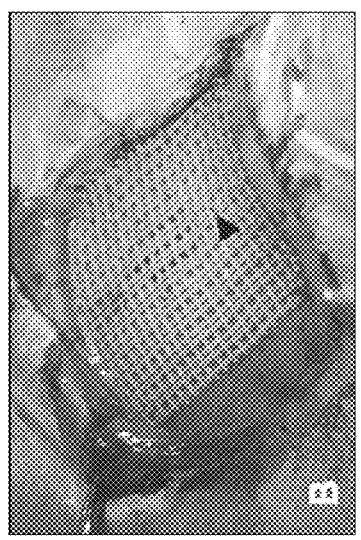
FIG. 21D illustrates ball burst testing performed with a 1-cm diameter ball pushed through the defect site reinforced with the mesh according to aspects of the present invention.

The implantation of a mesh and subsequent testing according to aspects of the present invention is illustrated in FIGS. 21A-D. FIG. 21A illustrates a full-thickness rat abdominal defect created using a custom designed 1-cm stainless steel punch. The defect appears oval in shape due to body wall tension applied. FIG. 21B illustrates a 4 cm×4 cm implant centered on top of the open defect, and held in place with single interrupted polypropylene sutures (arrow) through the implant and muscle. FIG. 21C illustrates an explanted specimen 94 days post implantation. FIG. 21D illustrates ball burst testing performed with a 1-cm diameter ball pushed through the defect site reinforced with the mesh.

While the present invention has been described in connection with a number of exemplary embodiments, and implementations, the present inventions are not so limited, but rather cover various modifications, and equivalent arrangements. For example, a knitted mesh according to aspects of the present invention may be used for a filler material. In one application, the knitted mesh may be cut into 1 mm×1 mm sections to separate one or more nodes, e.g., 3 nodes. The sections may be added to fat tissue or a hydro-gel to form a solution that can be injected into a defective area. Advantageously, the filler material may provide a desired texture, but will not unravel.

In another embodiment of the present invention, the mesh may incorporate a knit pattern design in which all edges will result in a finished edge. The finished edge will not need further handling by the surgeon such as cutting it to size but are made to meet the specific size requirement.

Figure 28:
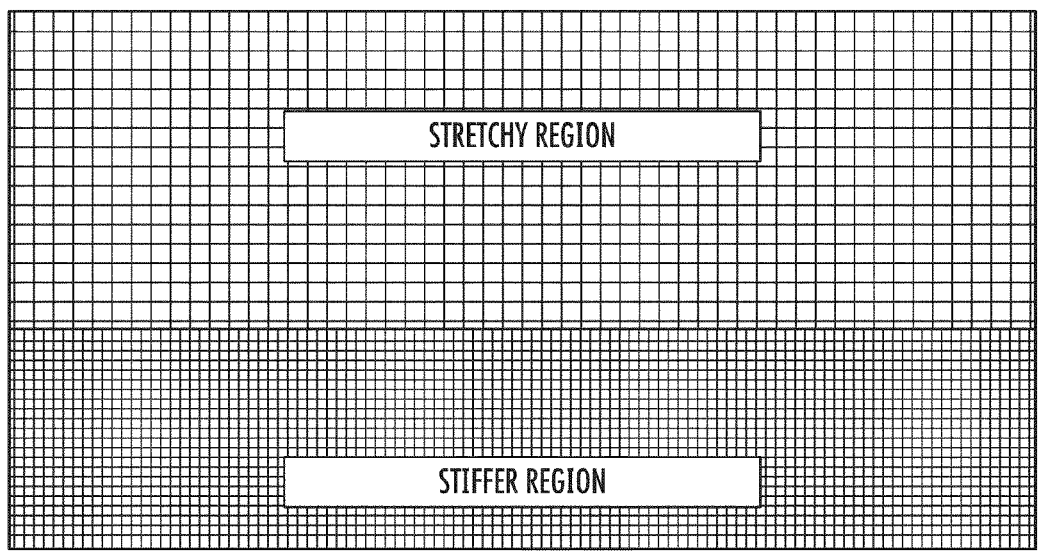
FIG. 28 illustrates an example scaffold with two regions; stretchy and stiffer.

In accordance with another aspect of the present invention, the silk scaffold incorporates more than one region. The regions are represented by varying properties of the scaffold. Examples of the properties include, but are not limited to, mechanical properties such as stretch, ultimate tensile strength and relaxation and to physical properties such as dimension (thickness, length, and width and pore size). For example, FIG. 28 illustrates that the scaffold may include a stretchy region and a stiffer region. A scaffold as shown in FIG. 28, for example, incorporates a region of differing stiffness. This allows the scaffold to stretch in particular regions. When used for breast reconstruction, for example, this design may help recreate a more normal breast shape.

A surgical scaffold device having varying regions may be created with knitting structures and relative machine parameters that can be varied to obtain the desired characteristics of the scaffold in different regions. The knitting structure involves variation in the methods of fabric formation such as the one classified as raschel knitting, warp knitting and weft knitting. The relative machine parameters may include, but are not limited to, variations such as yarn evolution (linear mass, twist value, among others), loop size and length, number of courses and wales per unit measure, fabric take up rate, number of needles per measure and relative size, feed rate and relative tension applied to the yarn. Furthermore, post fabric formation treatment may enhance the characteristics of the scaffold's different regions. The fabric treatments may include, but are not limited to, finishing and surface coating processes.

Figure 29A:
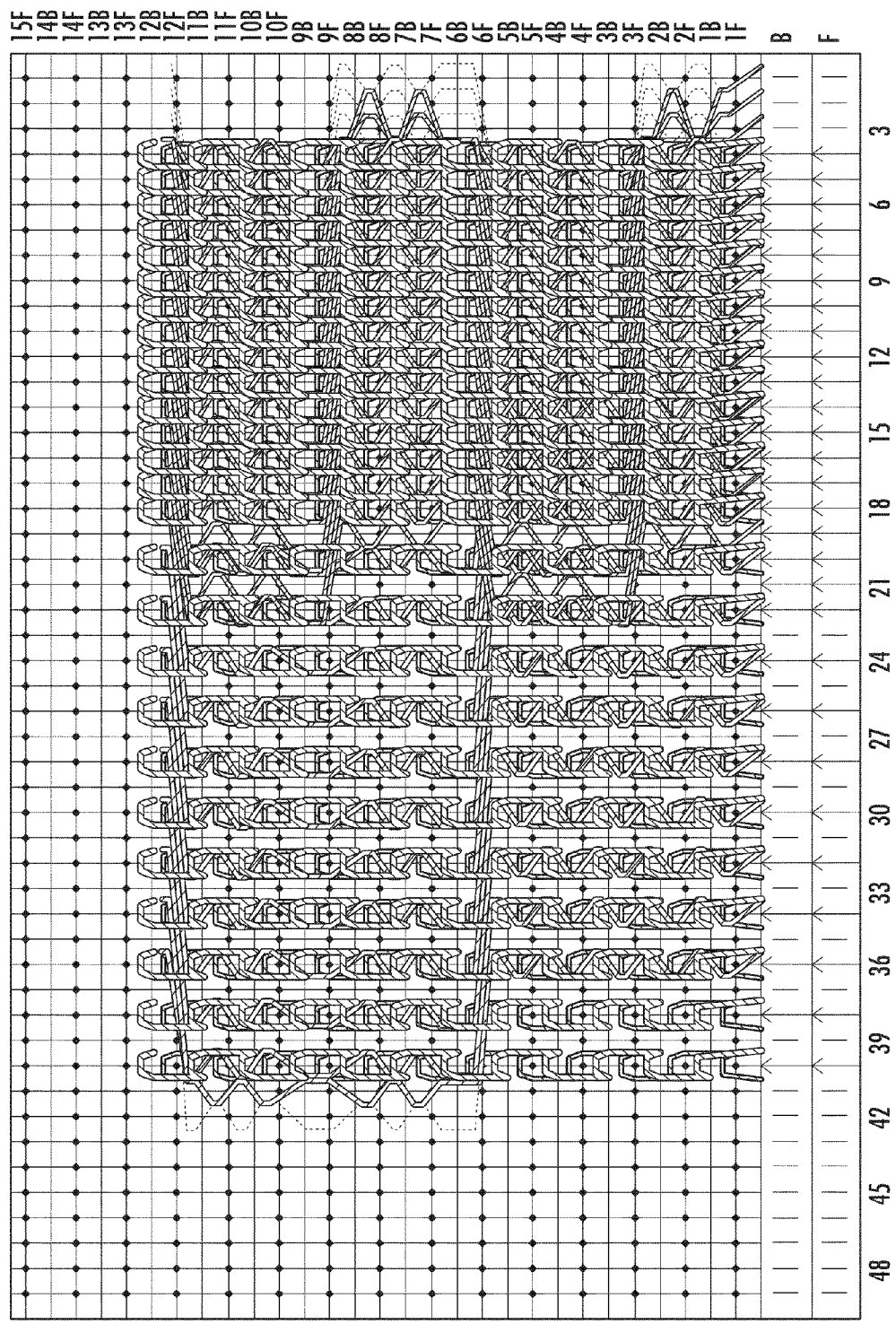
FIGS. 29A and 29B illustrate an example pattern layout for a double needle bed scaffold according to aspects of the present invention from FIG. 28 including all pattern and ground bars.
Figure 29B:
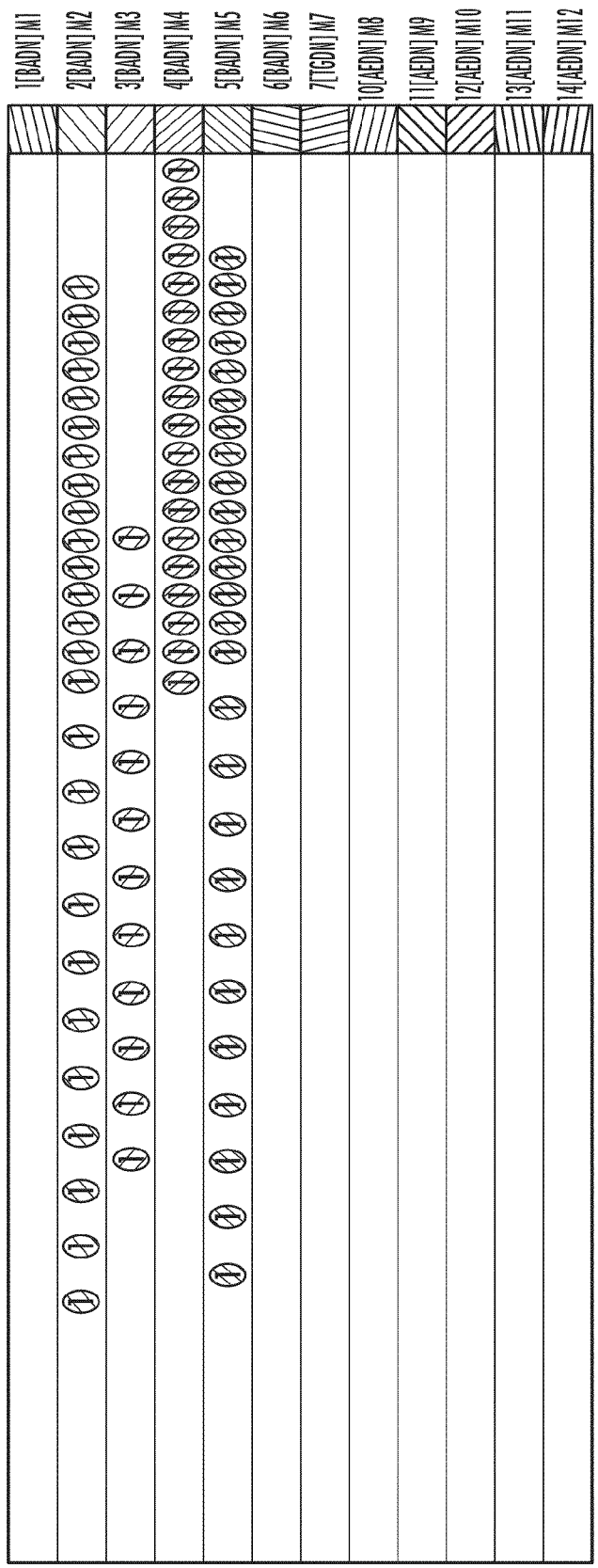
Figure 30A:
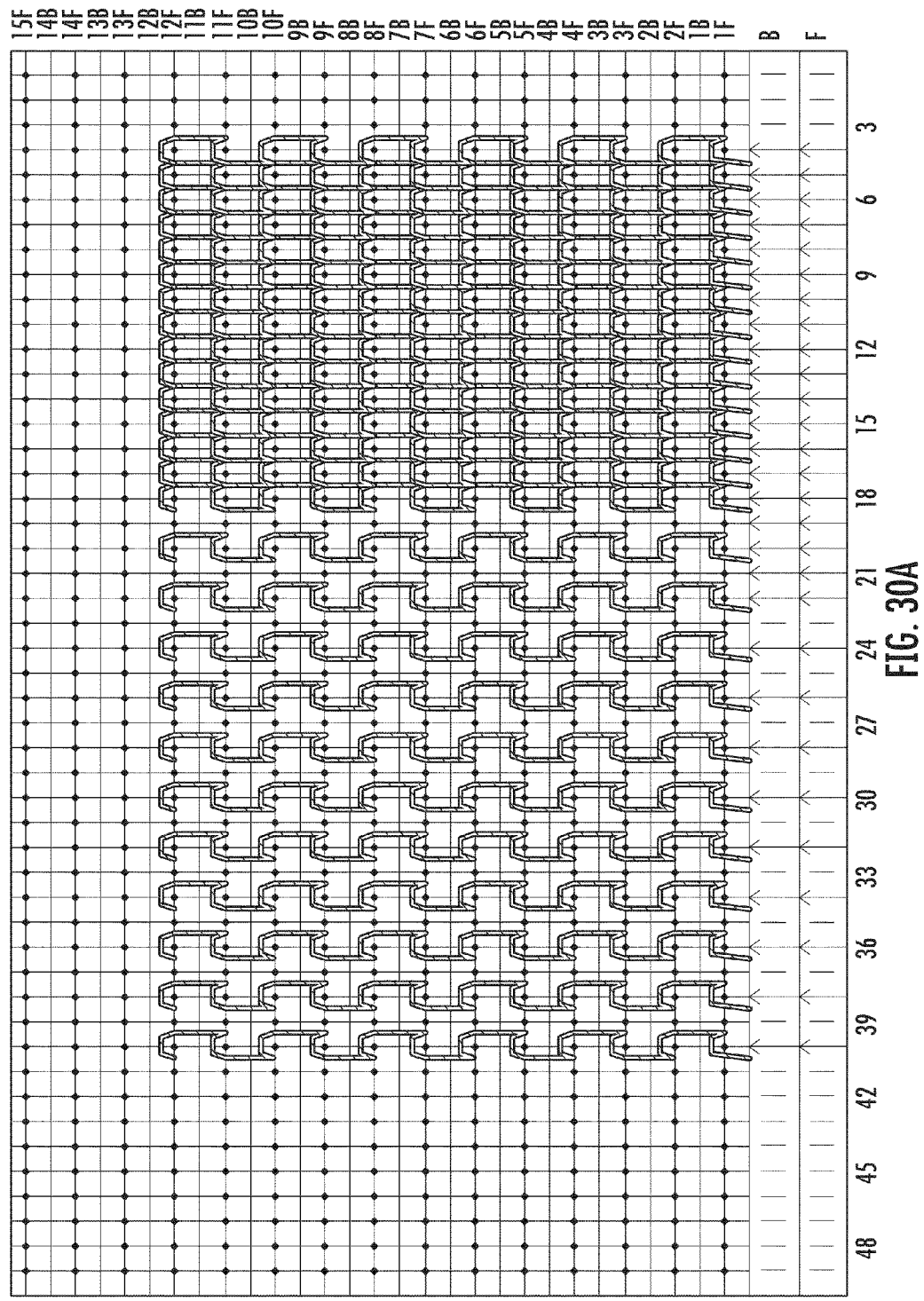
FIGS. 30A and 30B illustrate an example pattern layout for a double needle bed scaffold according to aspects of the present invention from drawing FIG. 28 for ground bar #2.
Figure 30B:
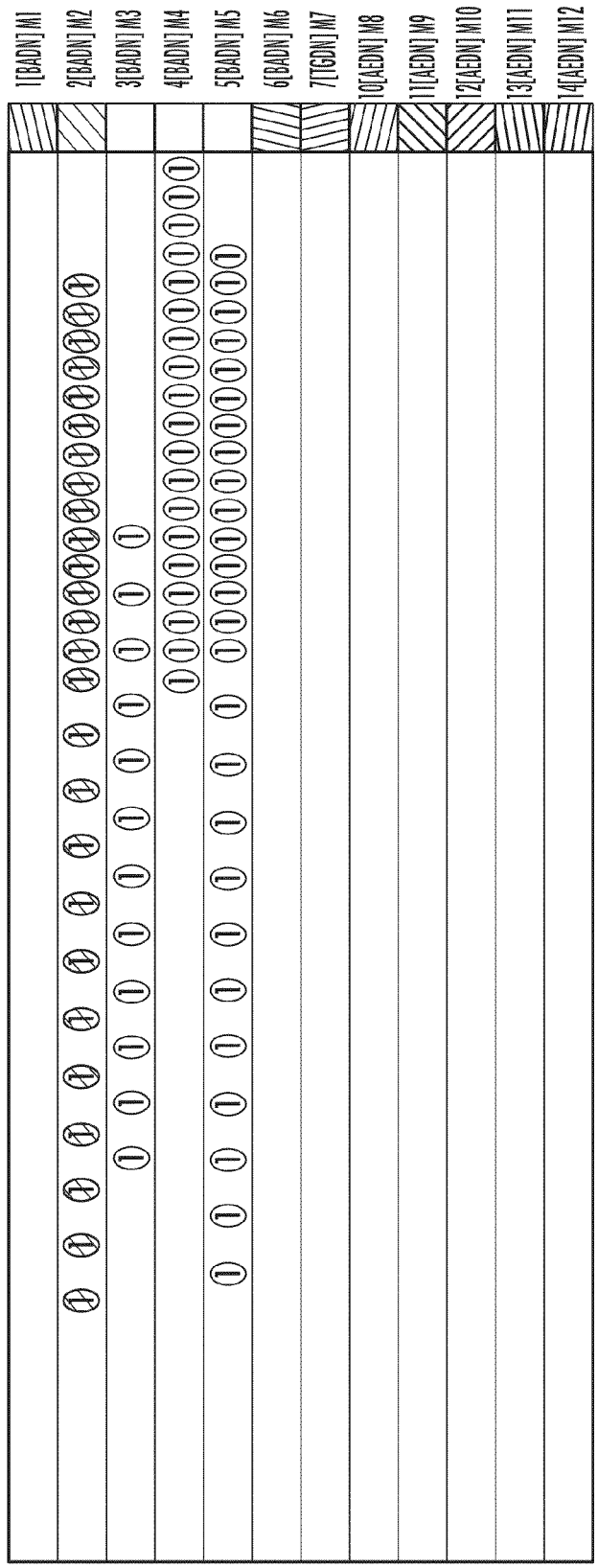
Figure 31A:
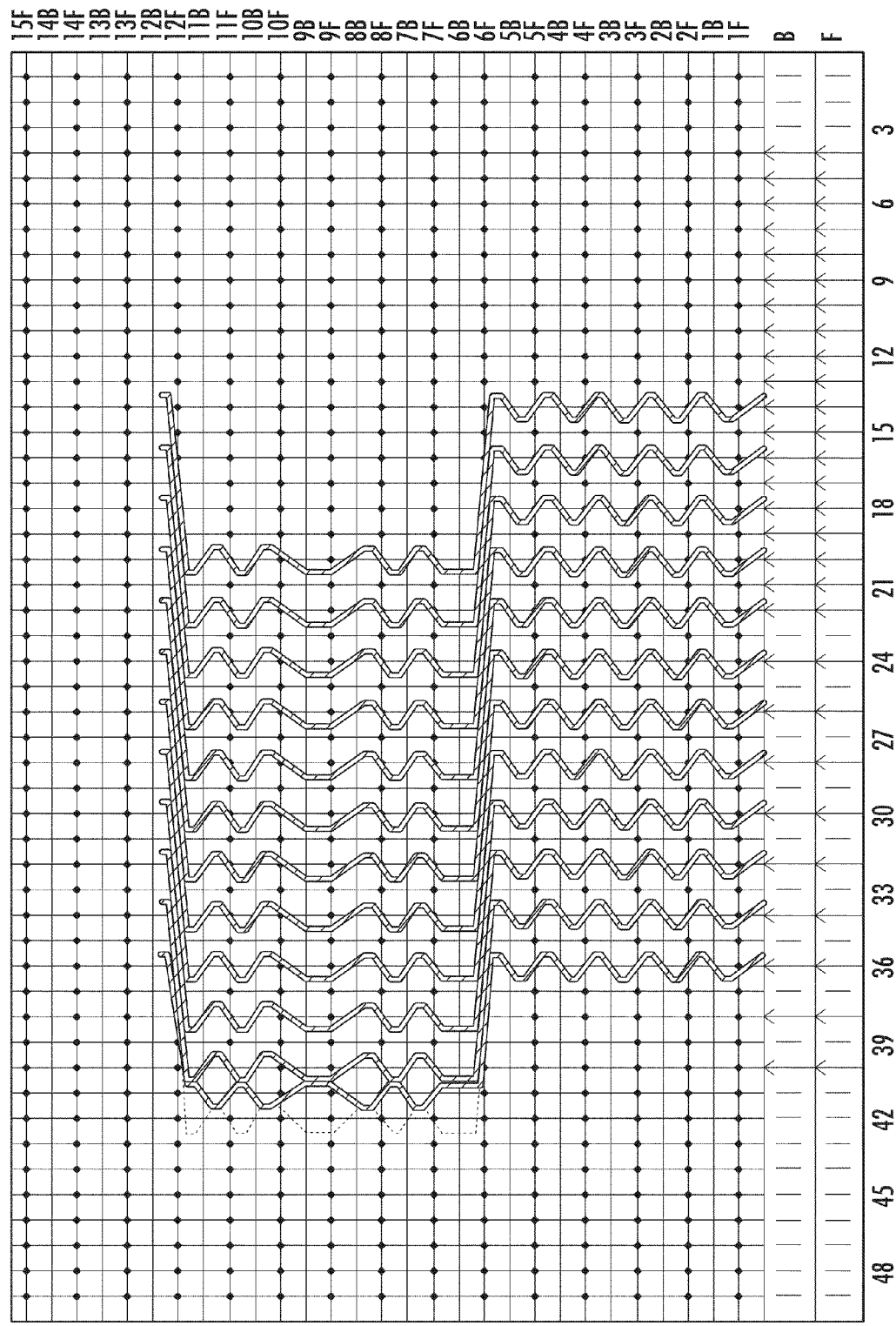
FIGS. 31A and 31B illustrate an example pattern layout for a double needle bed scaffold according to aspects of the present invention from FIG. 28 for pattern bar #3.
Figure 31B:
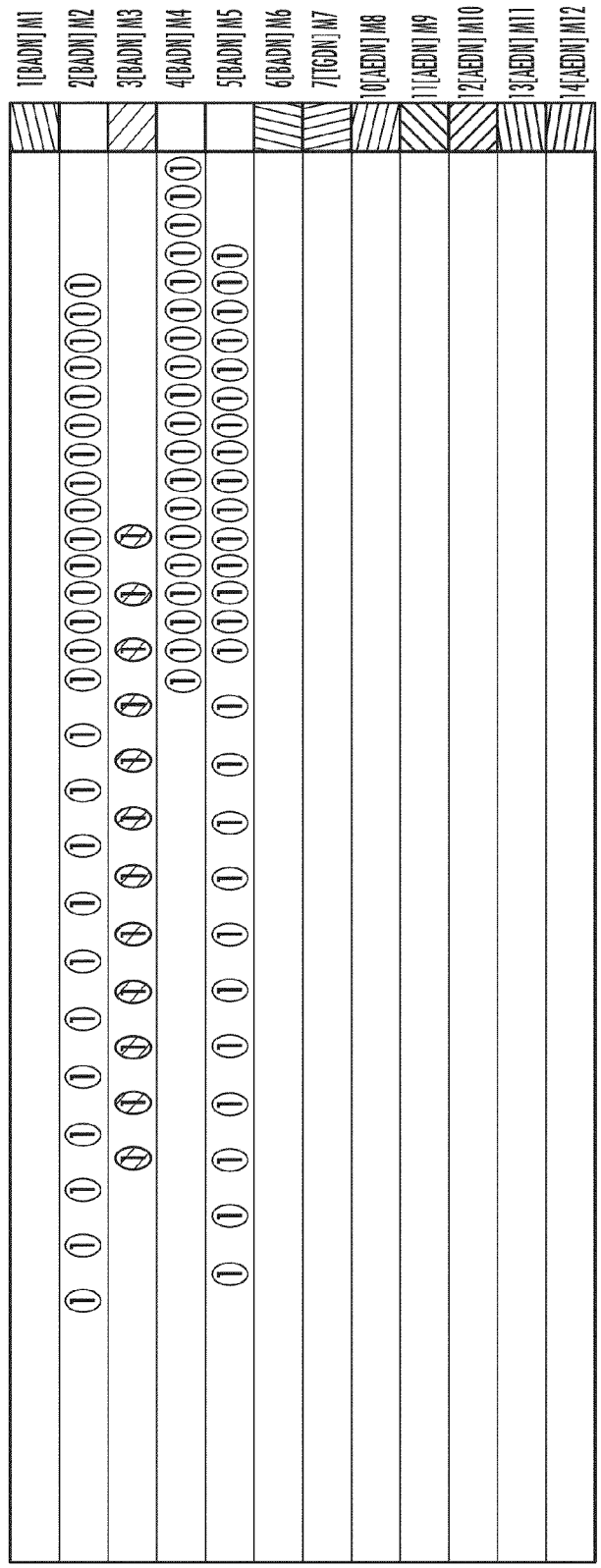
Figure 32A:
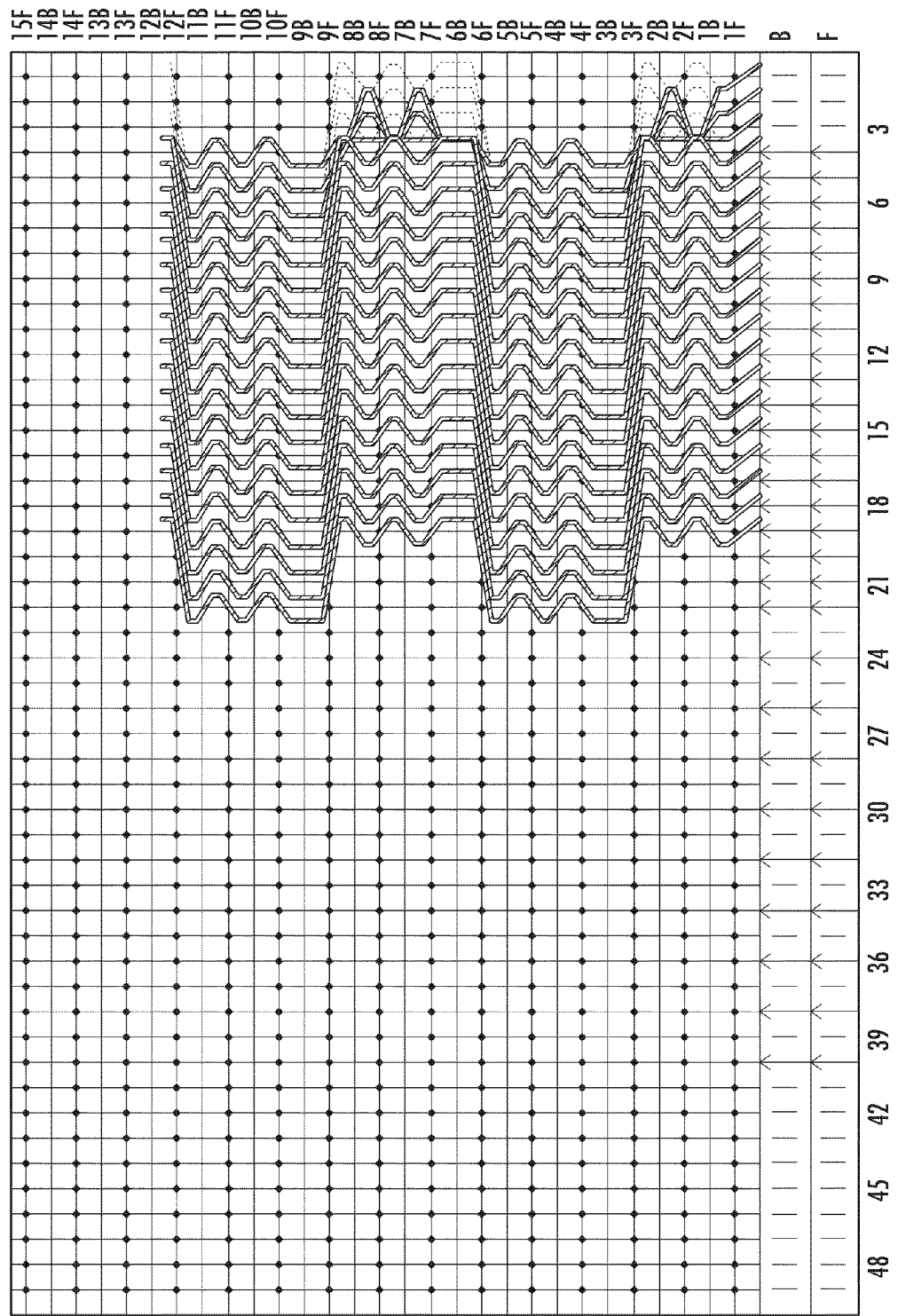
FIGS. 32A and 32B illustrate an example pattern layout for a double needle bed scaffold according to aspects of the present invention from FIG. 28 for pattern bar #4.
Figure 32B:
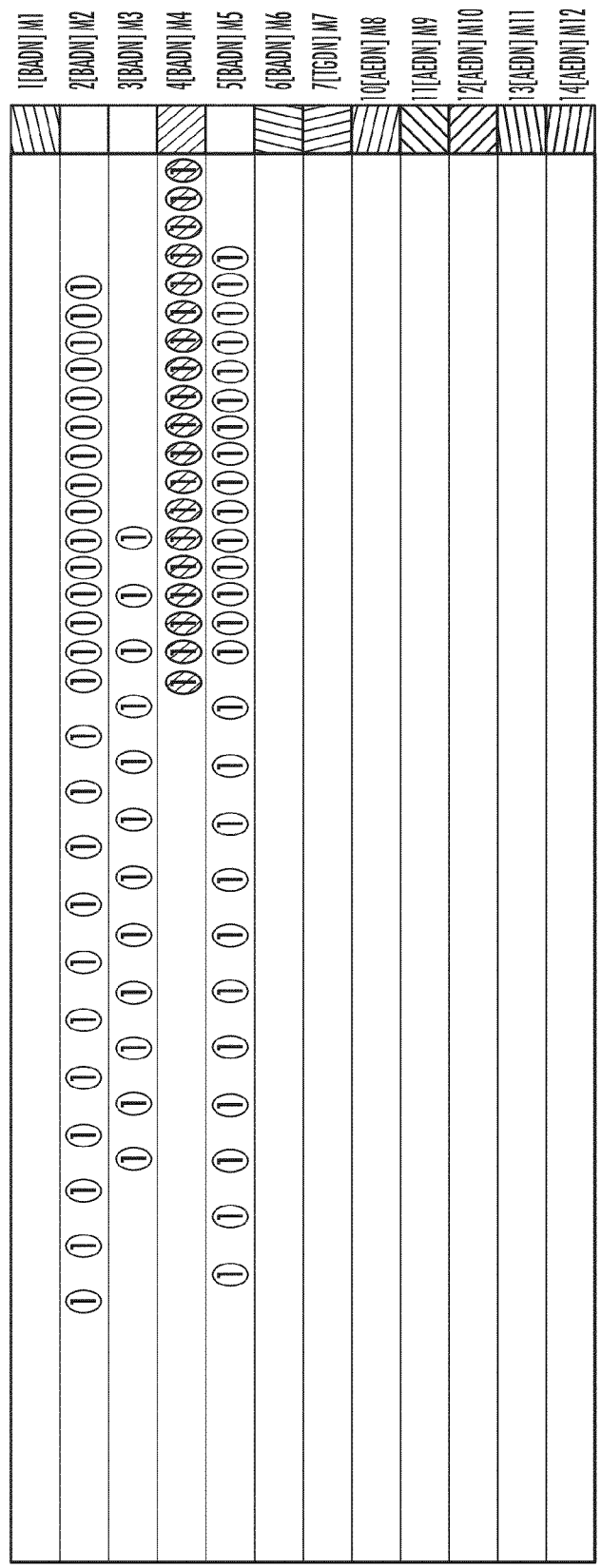
Figure 33A:
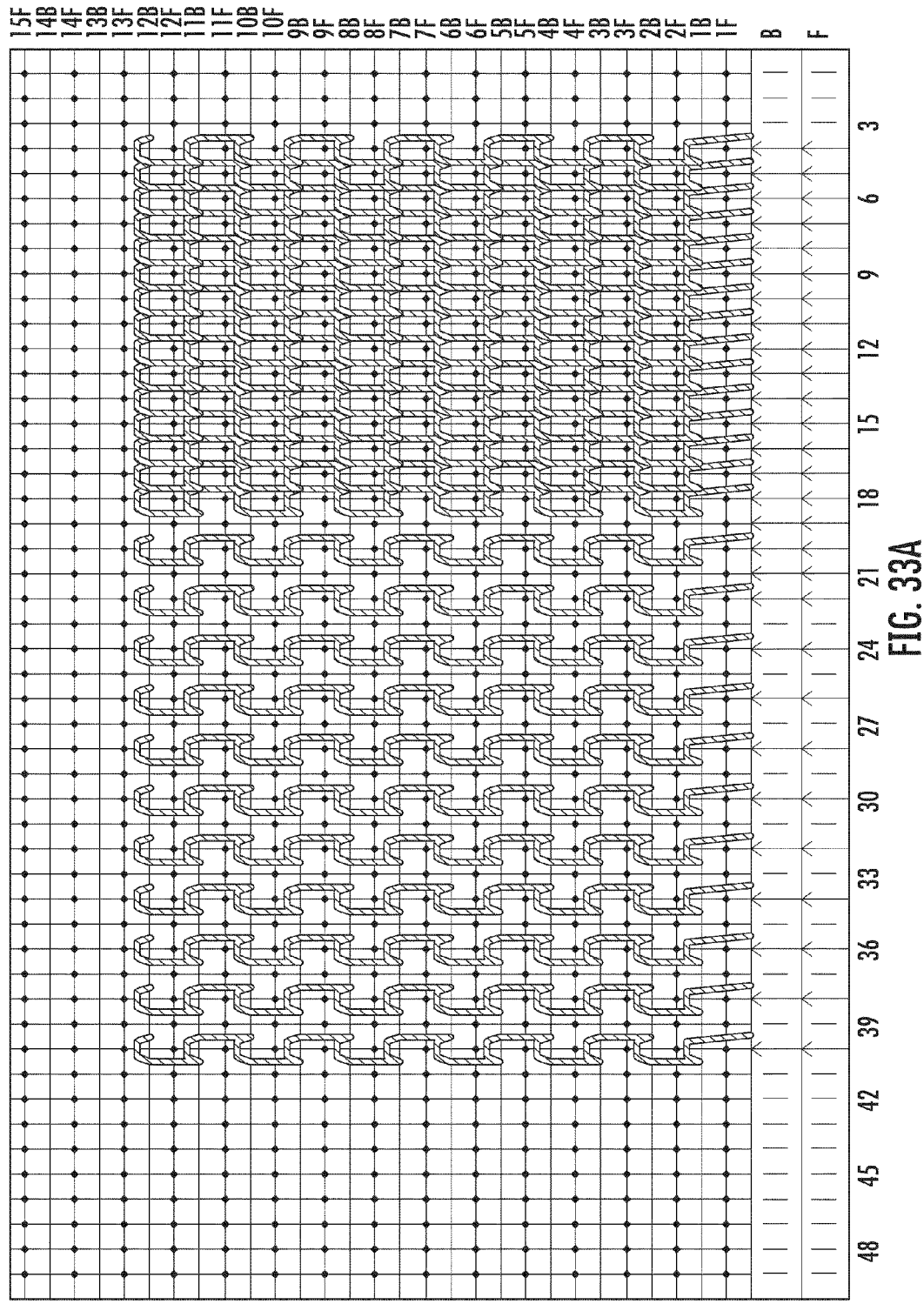
FIGS. 33A and 33B illustrate an example pattern layout for a double needle bed scaffold according to aspects of the present invention from FIG. 28 for ground bar #5.
Figure 33B:
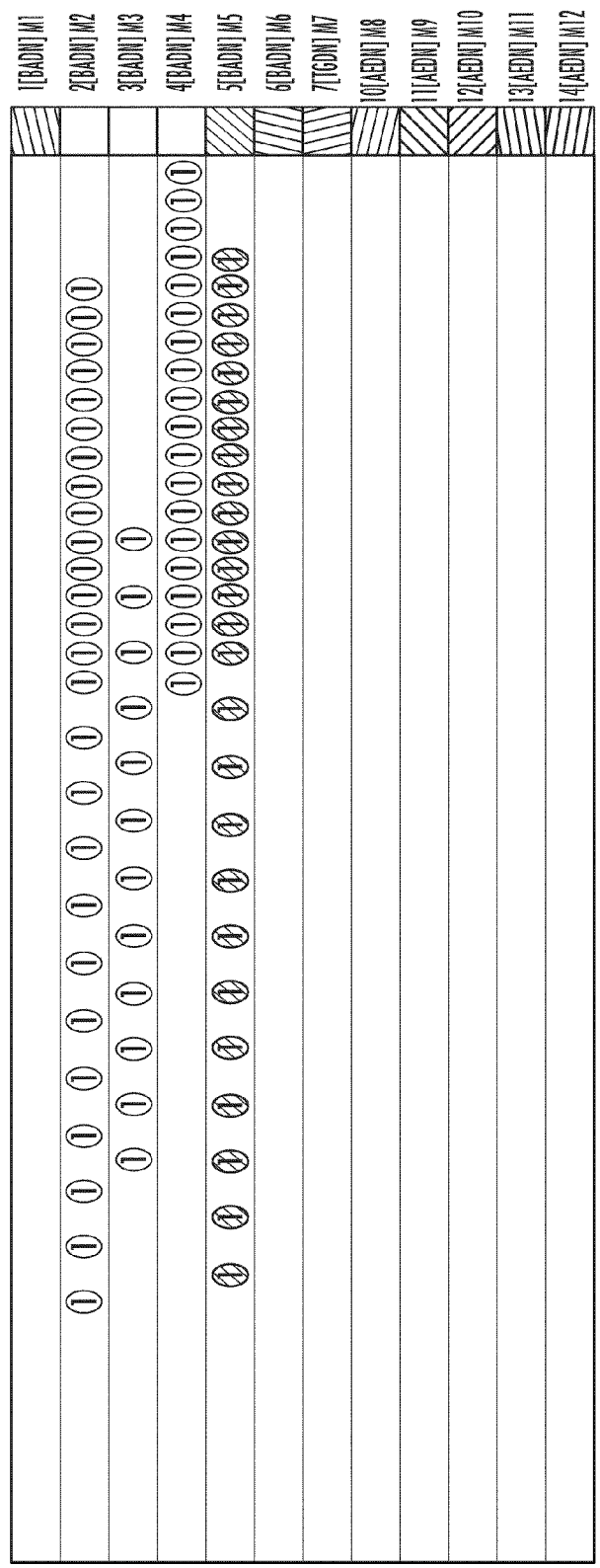
Figure 34:
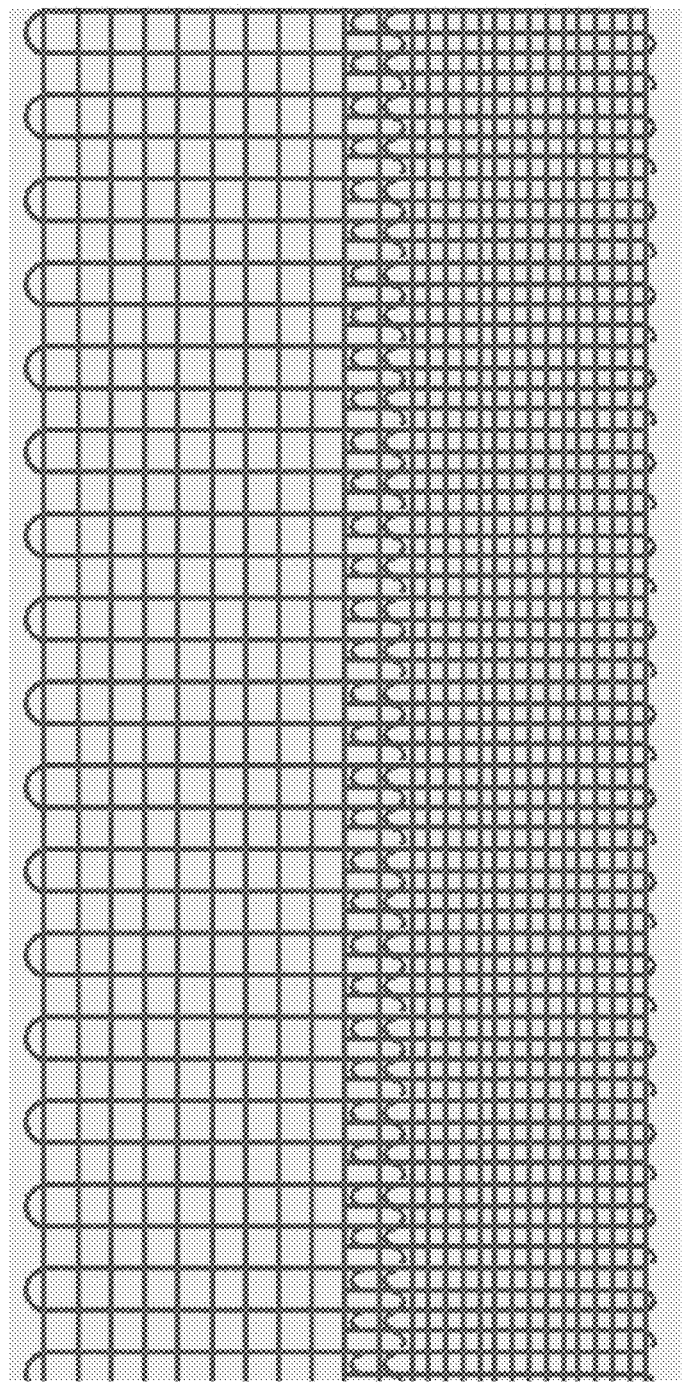
FIG. 34 illustrates an example pattern simulation for a double needle bed scaffold demonstrated in FIGS. 29A and 29B according to aspects of the present invention.

A surgical scaffold or mesh device according to aspects of the present invention may be created on a raschel knitting machine such as Comez DNB/EL-800-8B by the use of four movements as shown in pattern layout in FIGS. 29A and 29B: two movements in the wale direction, the vertical direction within the fabric, and two movements in the course direction, the horizontal direction of the fabric. The movements in the wale direction occur on separate needle beds with alternate yarns; loops that occur on every course are staggered within repeat. The yarn follows a repeat pattern of 2/1-1/1-1/2-2/2 for one of the wale direction movement as reported in FIGS. 30A and 30B and 1/1-1/2-2/2-2/1 for the other wale direction movement as reported by FIGS. 33A and 33B. The interlacing of the loops within the fabric allow for one yarn to become under more tension than the other under stress, locking it around the less tensioned yarn; keeping the fabric from unraveling when cut. This fabric is also made with different needle density within its width to create the different region of the fabric; in FIGS. 29A and 29B it can be noted that on the right side of the needle representation all the needle next to each other are selected, while on the left side of the needle representation every other needle is selected. The other movement in the course direction occurs in every few courses creating the openings in the scaffold. These yarns follow a repeat pattern of 1/1-2/2-1/1-2/2-1/1-2/2-1/1-2/2-1/1/-2/2/-1/1-8/8-8/8-7/7-8/8-7/7-8/8-7/7-8/8-7/7-8/8-7/7-8/8-1/1 for one of the course direction movement as reported in FIGS. 31A and 31B and 1/1-2/2-1/1-2/2-1/1-5/5-5/5-4/4/-5/5/-4/4-5/5-1/1-1/1-2/2-1/1-2/2-1/1-5/5-5/5-4/4/-5/5/-4/4-5/5-1/1 for the other course direction movement as reported in FIGS. 32A and 32B. The course direction movement's cover only selected area of the fabric to form the different region in the fabric. The pattern simulation layout of this pattern is rendered with ComezDraw 3 software in FIG. 34 demonstrating the two different regions within the fabric.

Figure 35:
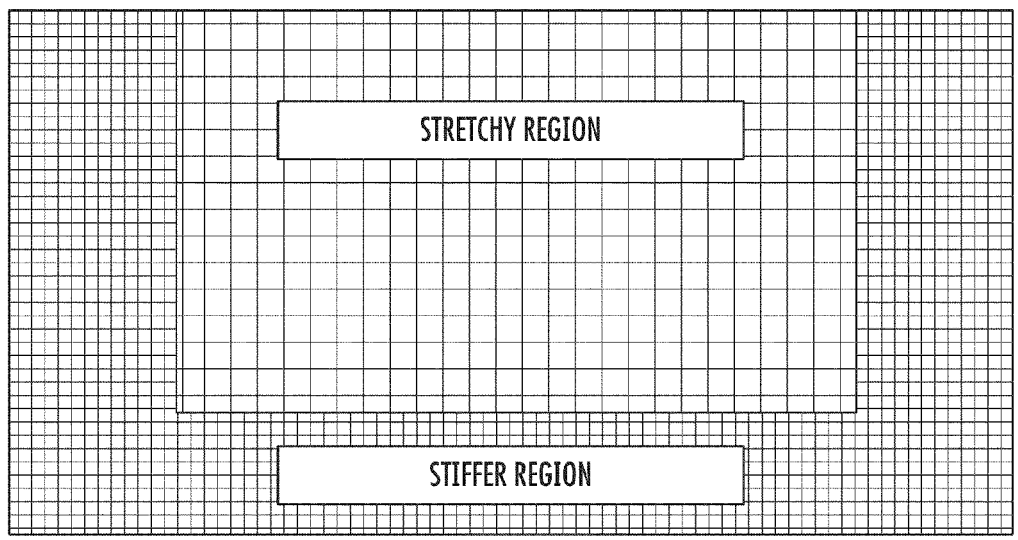
FIG. 35 illustrates an example scaffold drawing with two regions: stretchy and stiffer.

FIG. 35 illustrates an example drawing of a scaffold with two regions; stretchy and stiffer.

Figure 36A:
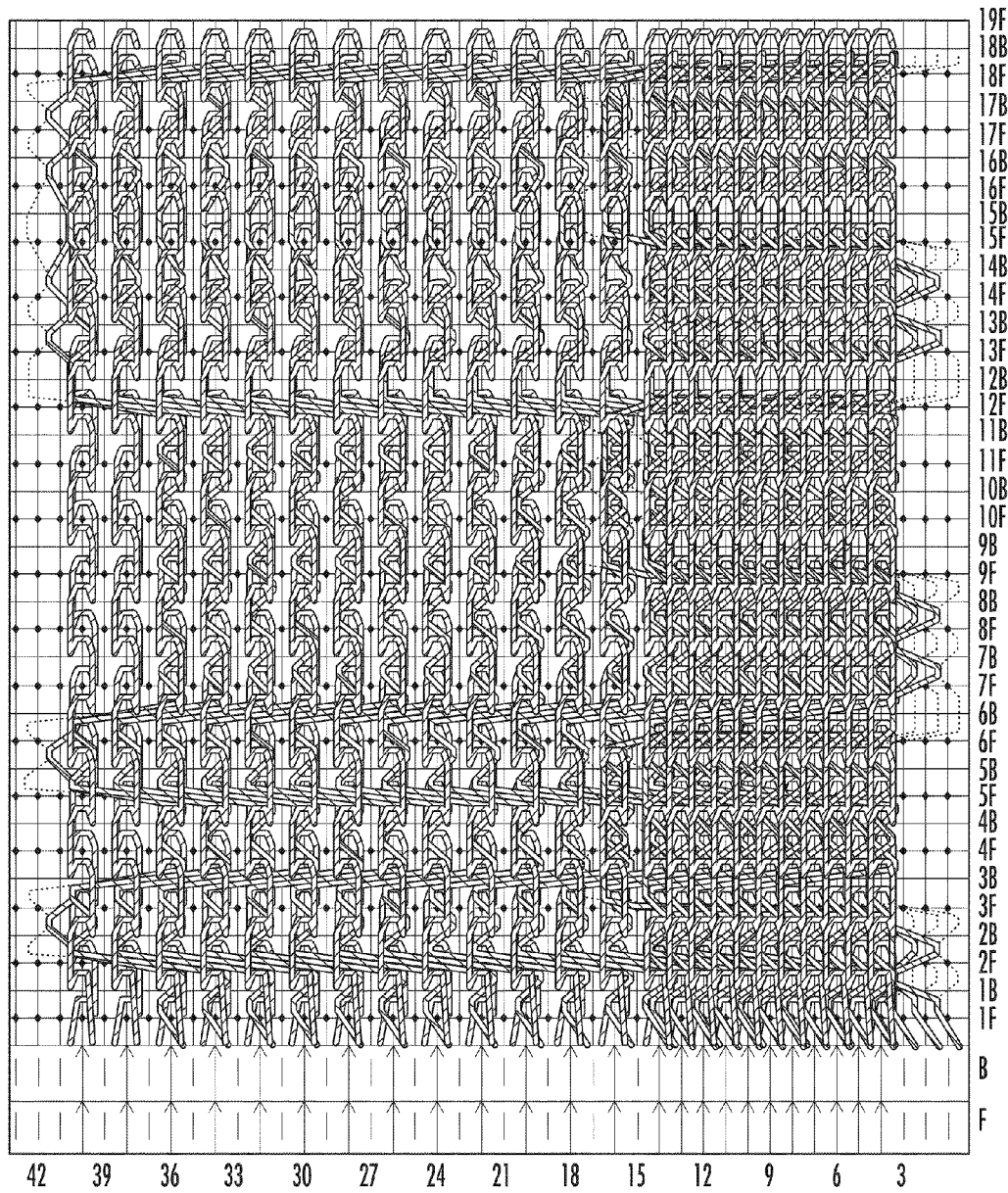
FIGS. 36A and 36B illustrate an example pattern layout for a double needle bed scaffold according to aspects of the present invention from drawing FIG. 35 including all pattern and ground bars.
Figure 36B:
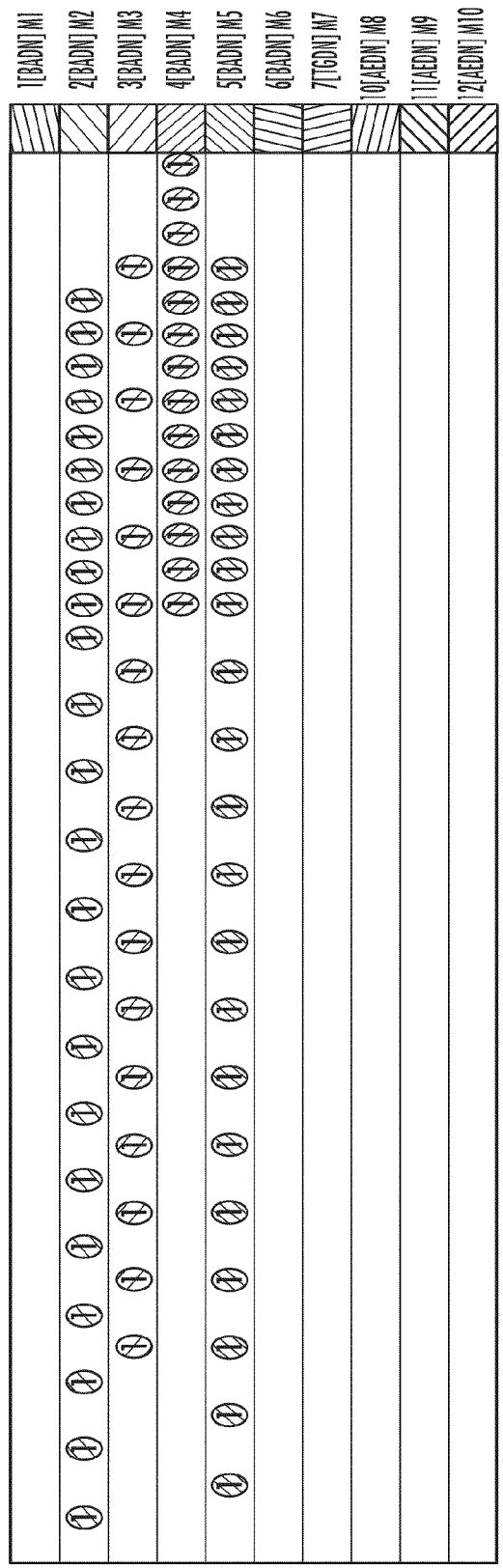
Figure 37A:
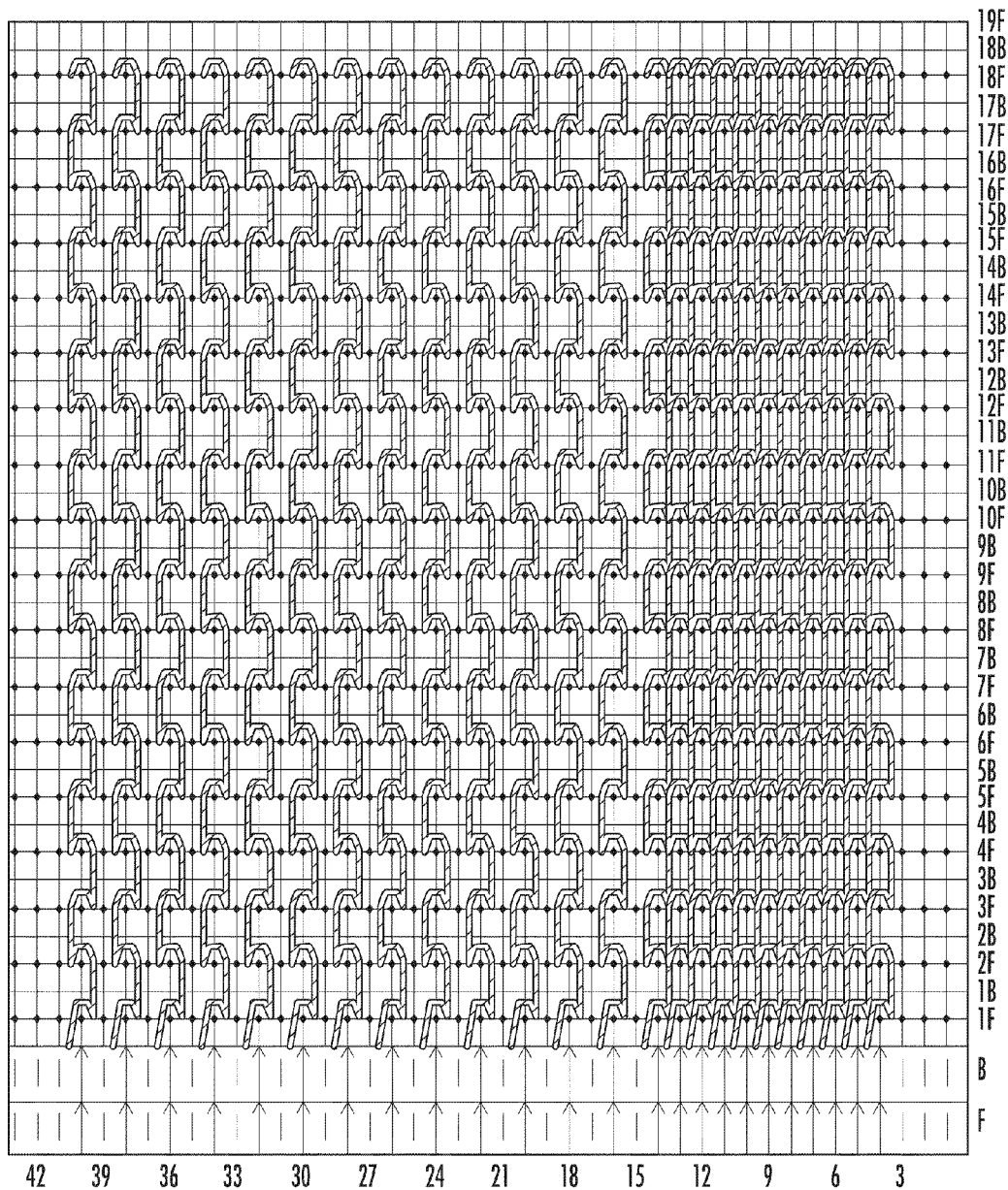
Figure 37B:
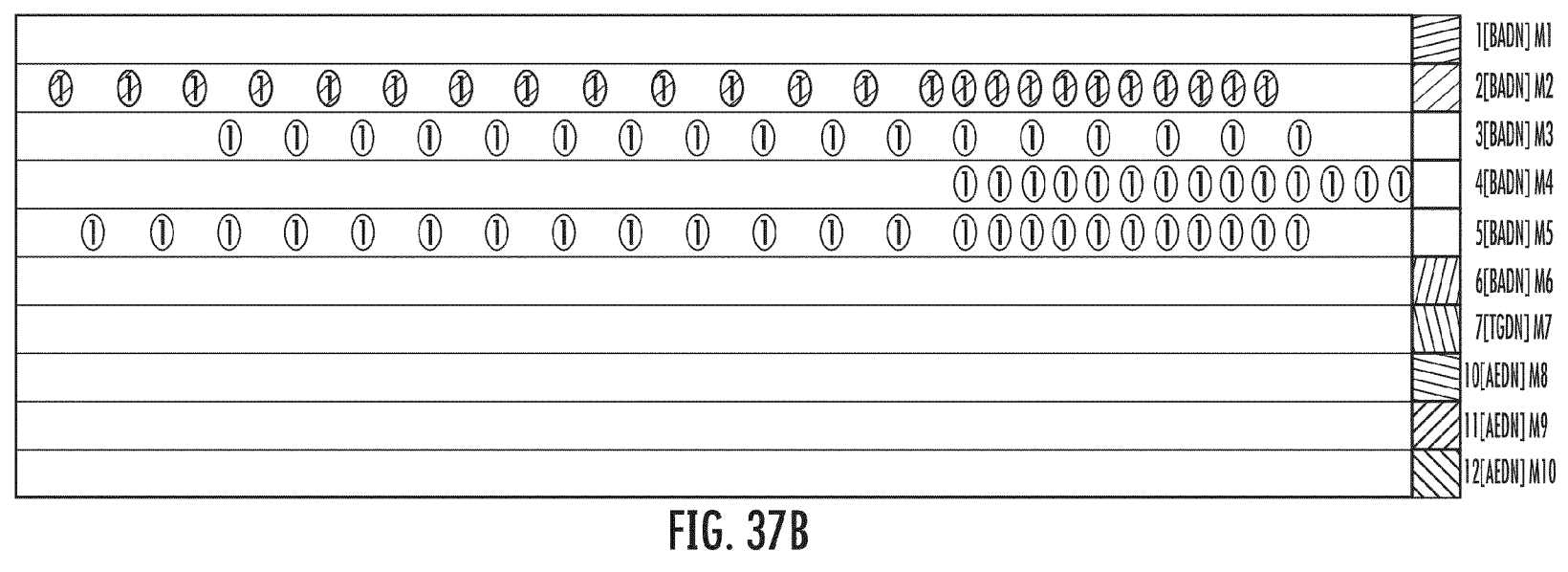
Figure 38A:
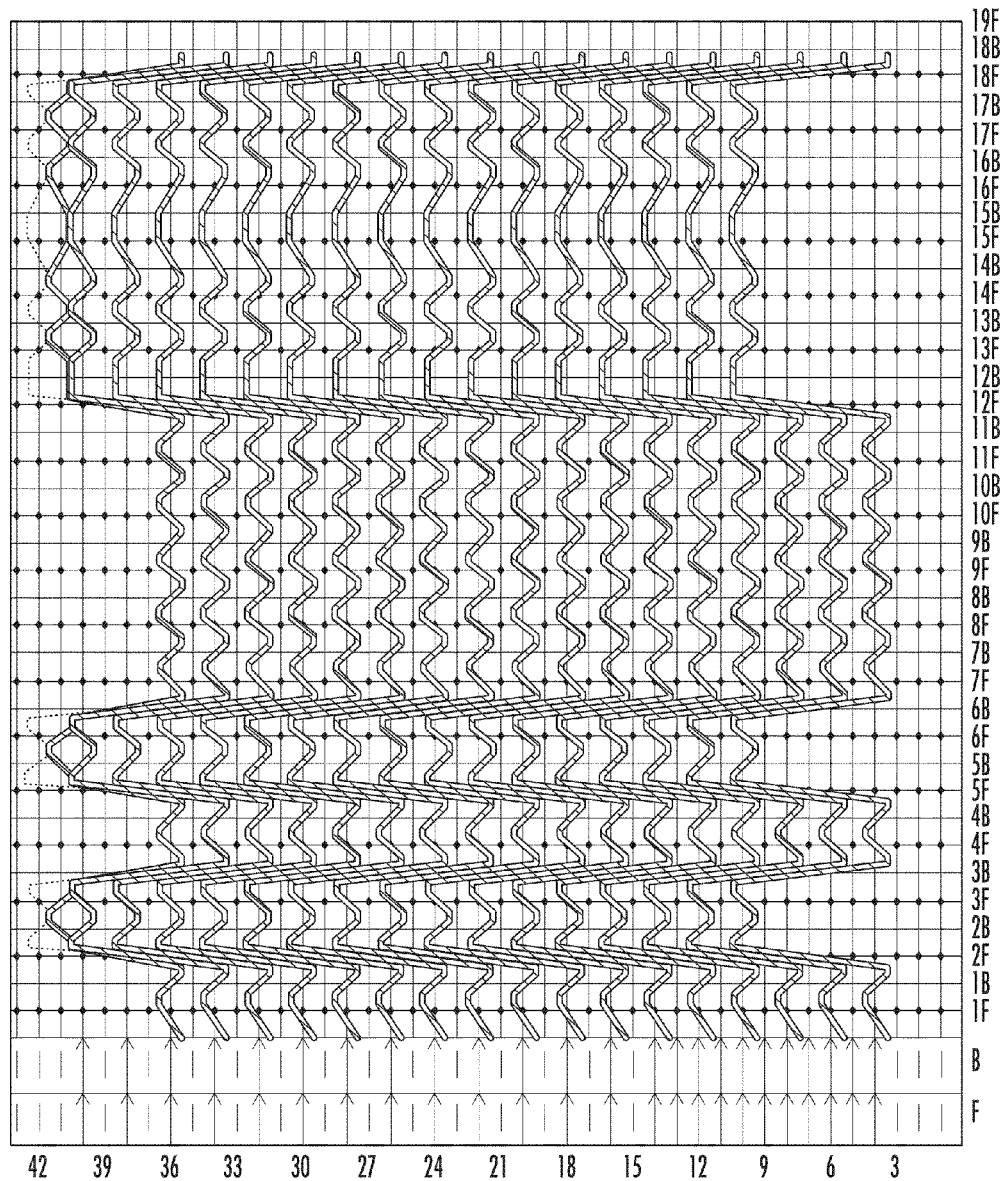
FIGS. 38A and 38B illustrate an example pattern layout for a double needle bed scaffold according to aspects of the present invention from FIG. 35 for pattern bar #3.
Figure 38B:
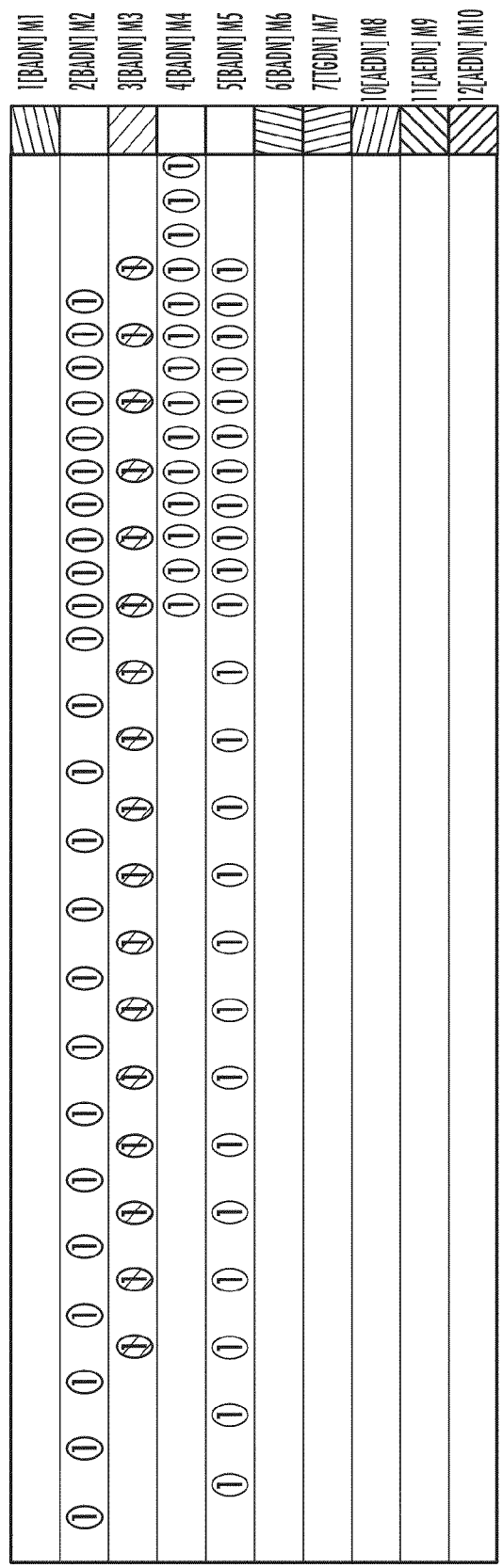
Figure 39A:
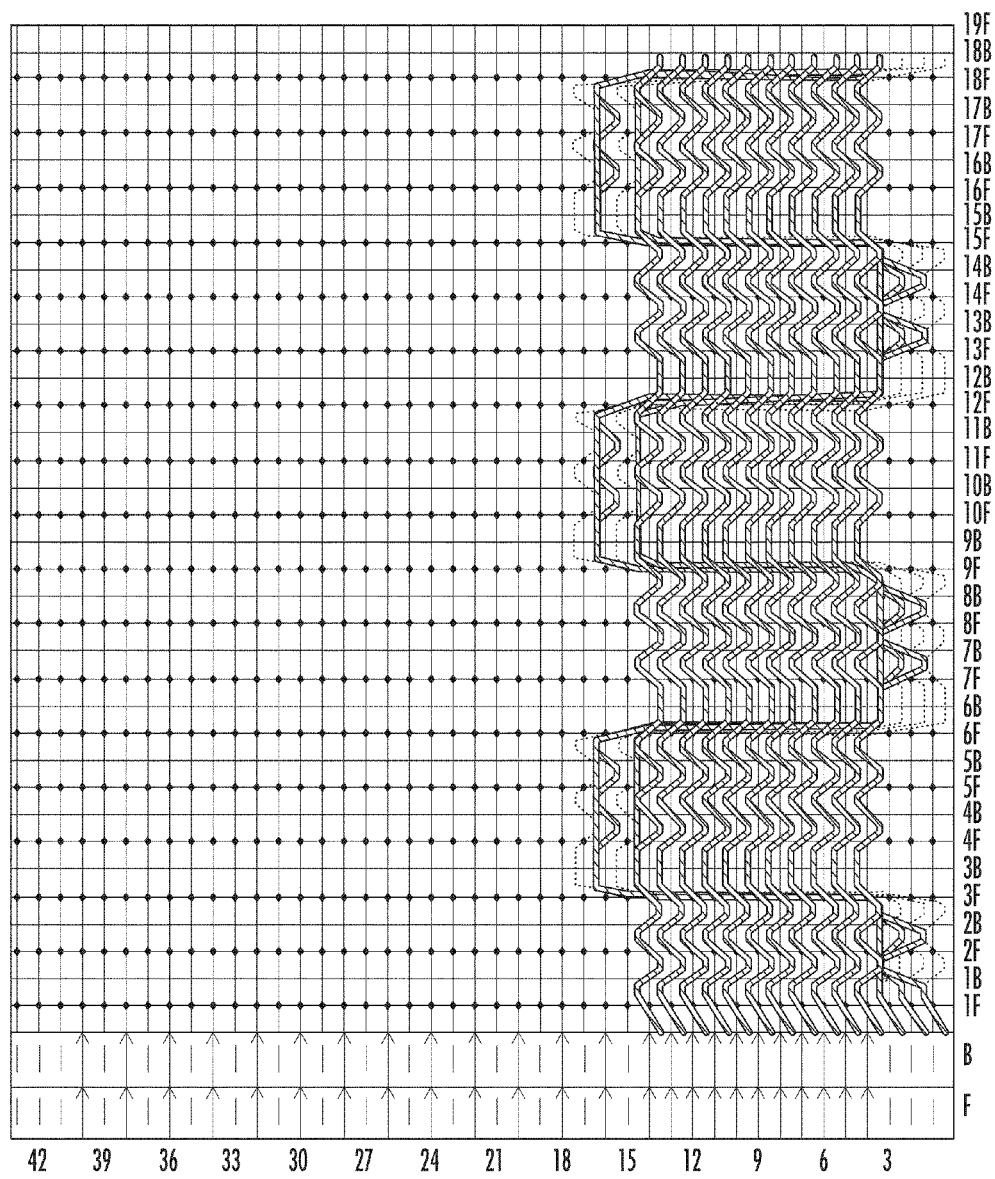
FIGS. 39A and 39B illustrate an example pattern layout for a double needle bed scaffold according to aspects of the present invention from FIG. 35 for pattern bar #4.
Figure 39B:
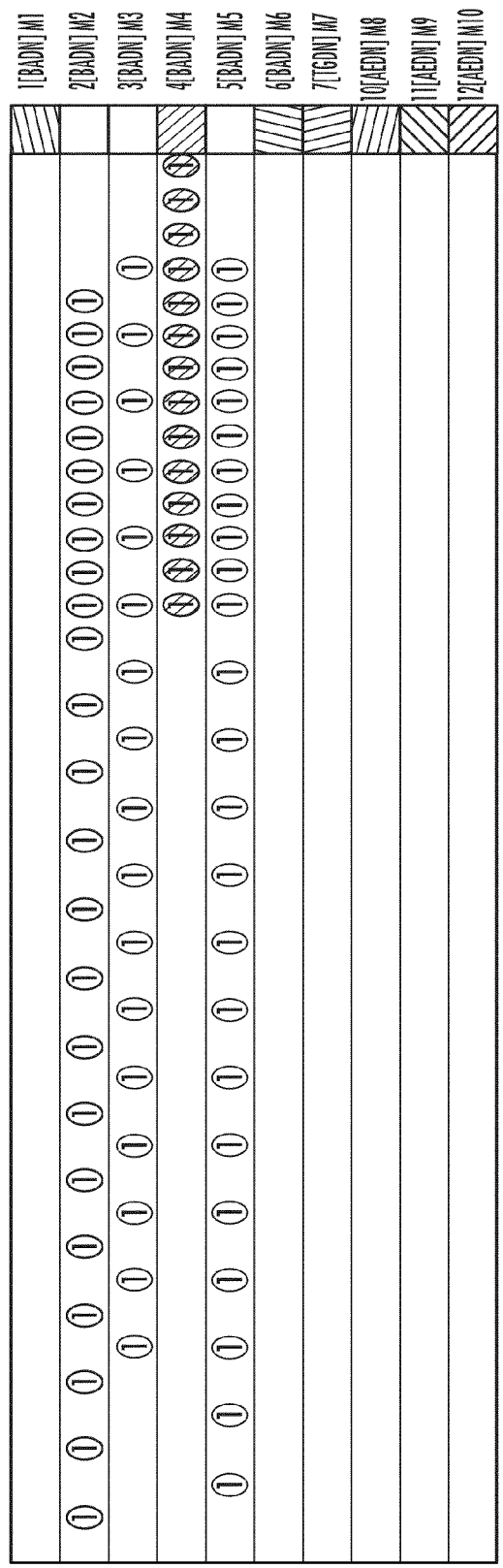
Figure 40A:
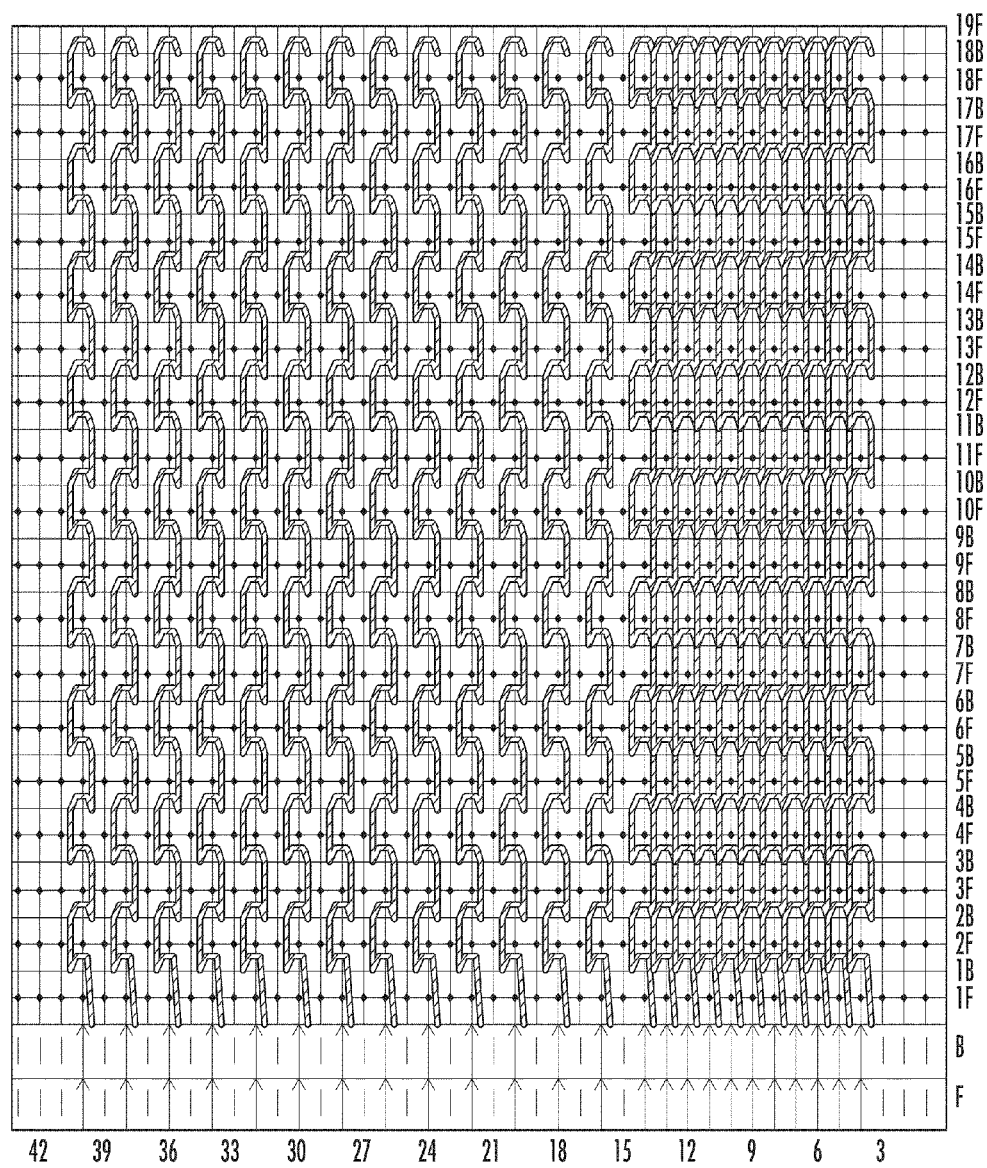
FIGS. 40A and 40B illustrate an example pattern layout for a double needle bed scaffold according to aspects of the present invention from FIG. 35 for ground bar #5.
Figure 40B:
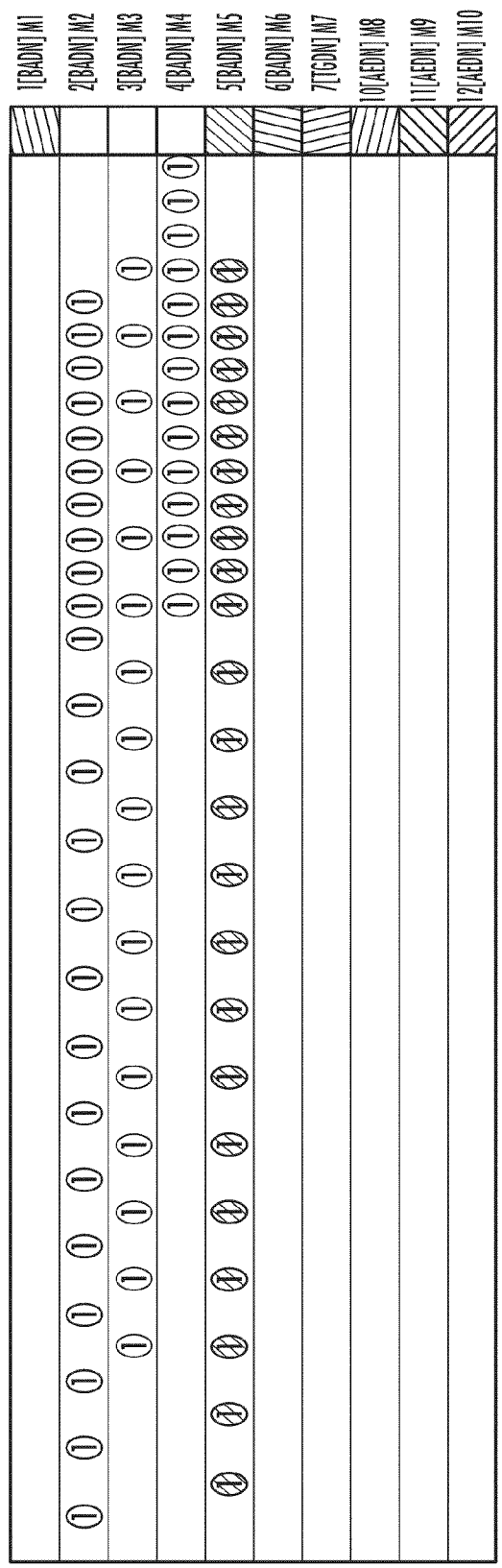
Figure 41:
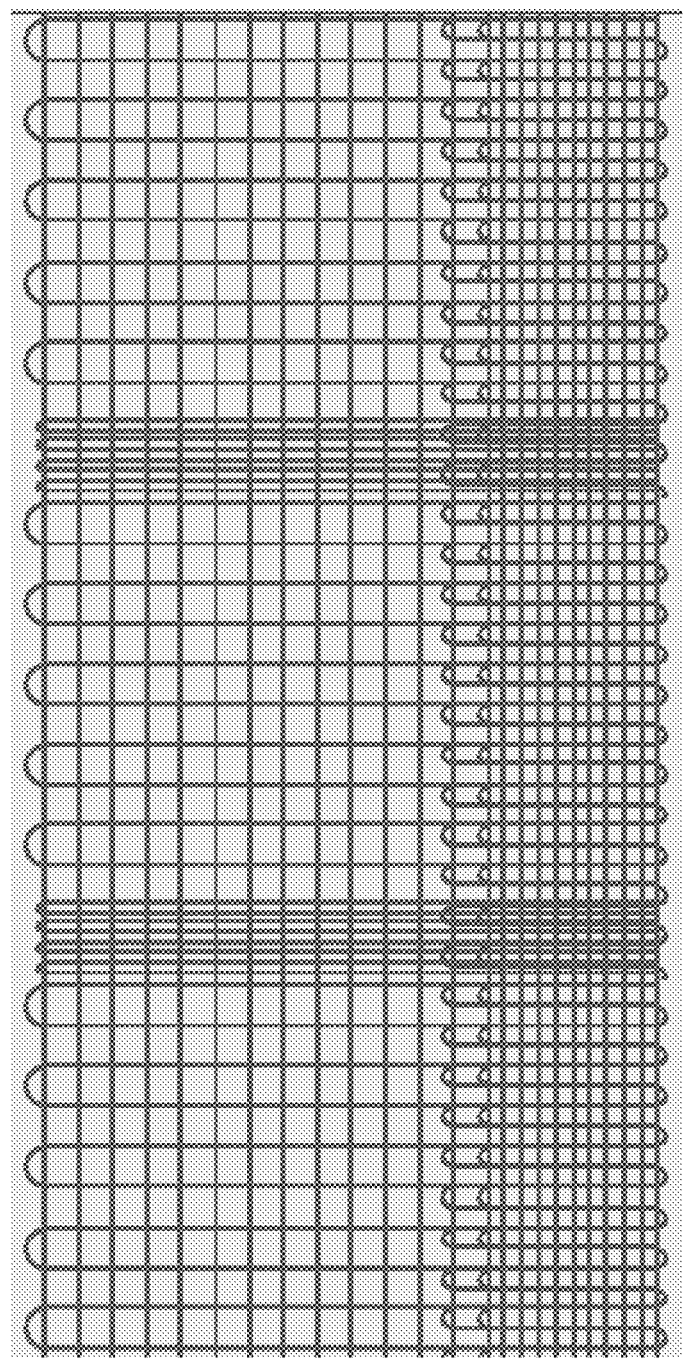
FIG. 41 illustrates an example pattern simulation for a double needle bed scaffold demonstrated in FIGS. 36A and 36B according to aspects of the present invention.

A surgical scaffold device according to aspect of the present invention may be created on a raschel knitting machine such as Comez DNB/EL-800-8B by the use of four movements as shown in pattern layout in FIGS. 36A and 36B: two movements in the wale direction, the vertical direction within the fabric, and two movements in the course direction, the horizontal direction of the fabric. The movements in the wale direction occur on separate needle beds with alternate yarns; loops that occur on every course are staggered within repeat. The yarn follows a repeat pattern of 2/1-1/1-1/2-2/2 for one of the wale direction movement as reported in FIGS. 37A and 37B and 1/1-1/2-2/2-2/1 for the other wale direction movement as reported by FIGS. 40A and 40B. The interlacing of the loops within the fabric allow for one yarn to become under more tension than the other under stress, locking it around the less tensioned yarn; keeping the fabric from unraveling when cut. This fabric is also made with different needle density within its width to create the different region of the fabric; in FIGS. 36A and 36B it can be noted that on the right side of the needle representation all the needle next to each other are selected, while on the left side of the needle representation every other needle is selected. The other movement in the course direction occurs in every few courses creating the openings in the scaffold. These yarns follow a repeat pattern of 1/1/-2/2-1/1-8/8-7/7-8/8-1/1/-2/2-1/1-8/8-7/7-8/8-1/1-2/2-1/1-2/2/2-1/1-2/2-1/1-2/2-1/1/-2/2-1/1-8/8-8/8-7/7-8/8-7/7-8/8-7/7-8/8-7/7-8/8-1/1 for one of the course direction movement as shown in FIGS. 38A and 38B and 1/1-2/2-1/1-2/2-1/1-5/5-5/5-4/4/-5/5-4/4-5/5-1/1-1/1-2/2-1/1-2/2-1/1-5/5-5/5-4/4-5/5-4/4-5/5-1/1-1/1-2/2-1/1-2/2-1/1-5/5-5/5-4/4/-5/5-4/4-5/5-1/1 for the other course direction movement as shown in FIGS. 39A and 39B. The course direction movements cover only selected area of the fabric to form the different regions in the fabric. The pattern simulation layout with a repeat from the basic pattern in FIGS. 36A and 36B is rendered with ComezDraw 3 software in FIG. 41 demonstrating the two different regions within the fabric. The pattern repeat is developed by repeating two (2) times from movement 1 to movement 12 of the basic pattern; follow by repeating five (5) times from movement 13 to movement 36 of the basic pattern.

Figure 42:
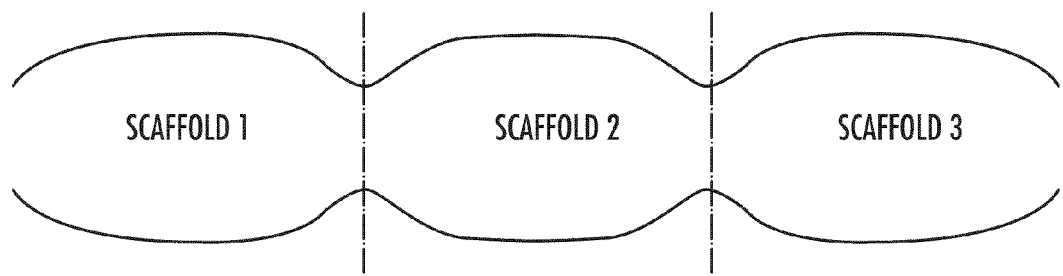
FIG. 42 illustrates an example scaffold with elliptical form.
Figure 43A:
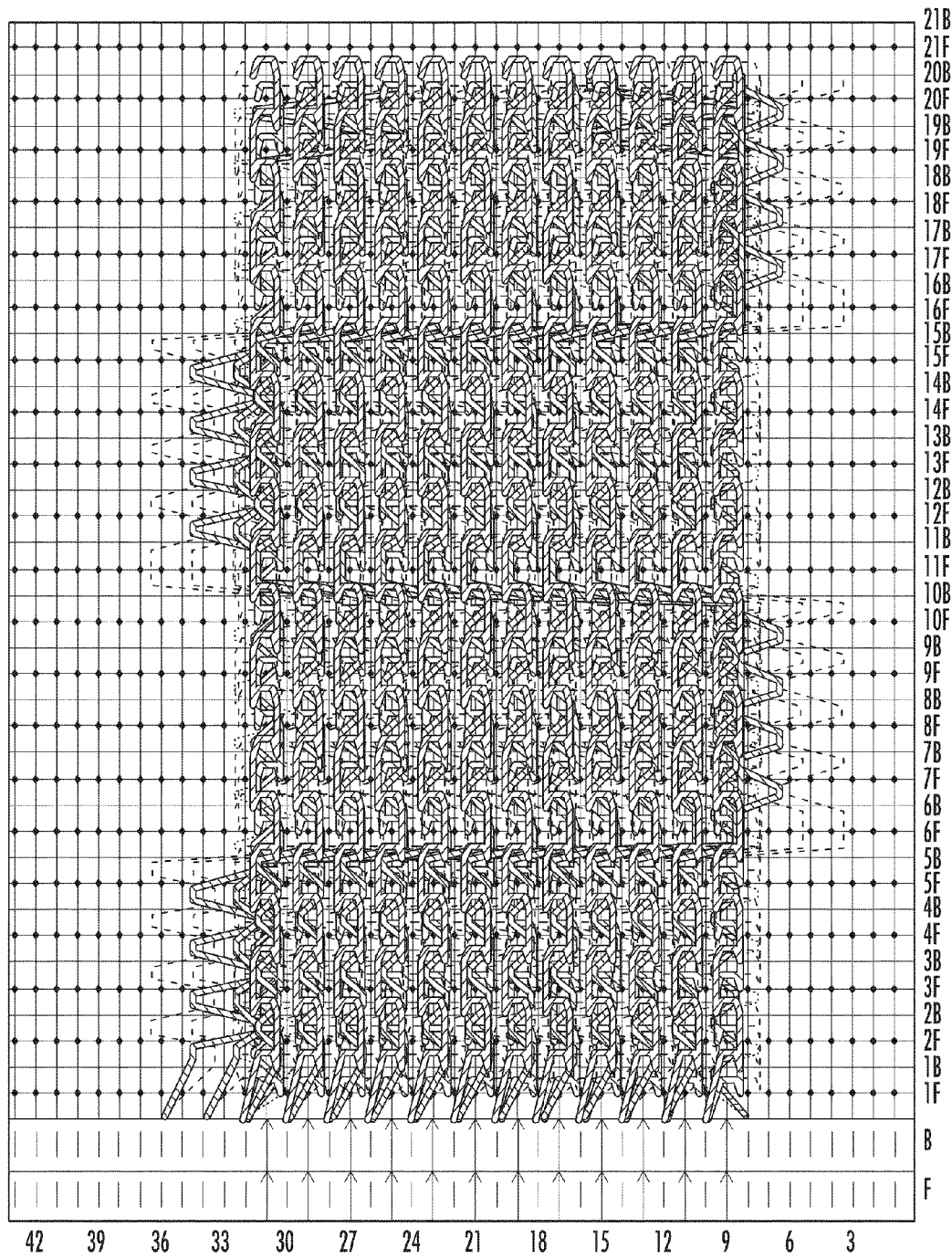
FIGS. 43A and 43B illustrate an example pattern layout for a double needle bed scaffold according to aspects of the present invention from FIG. 42 including all pattern and ground bars.
Figure 43B:
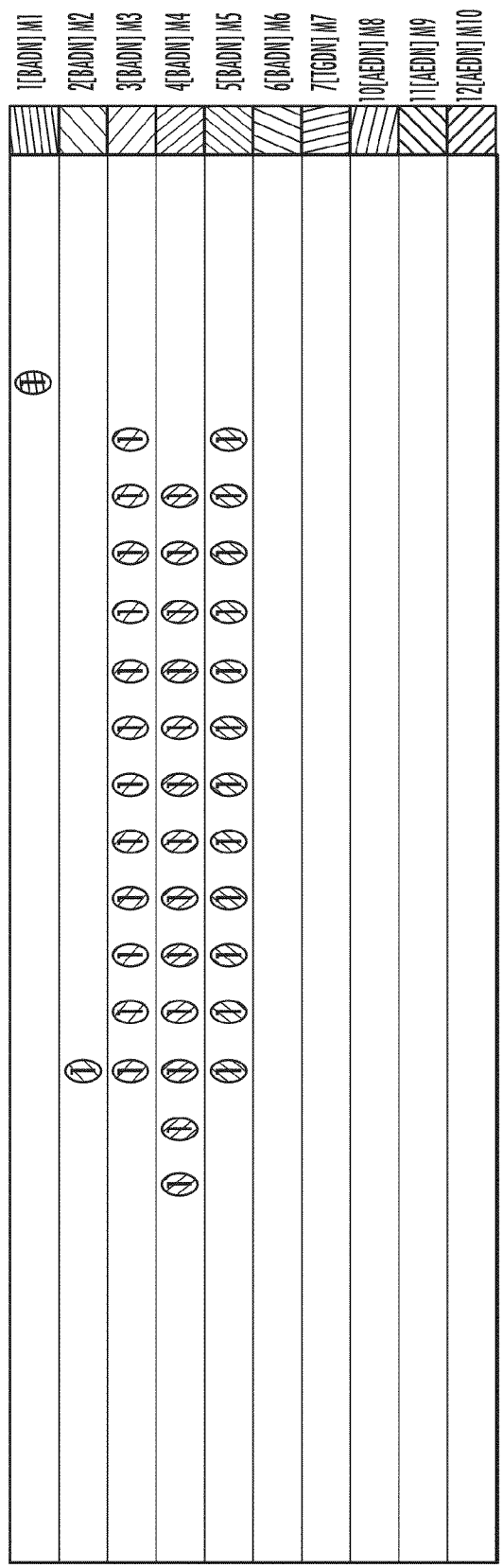
Figure 46A:
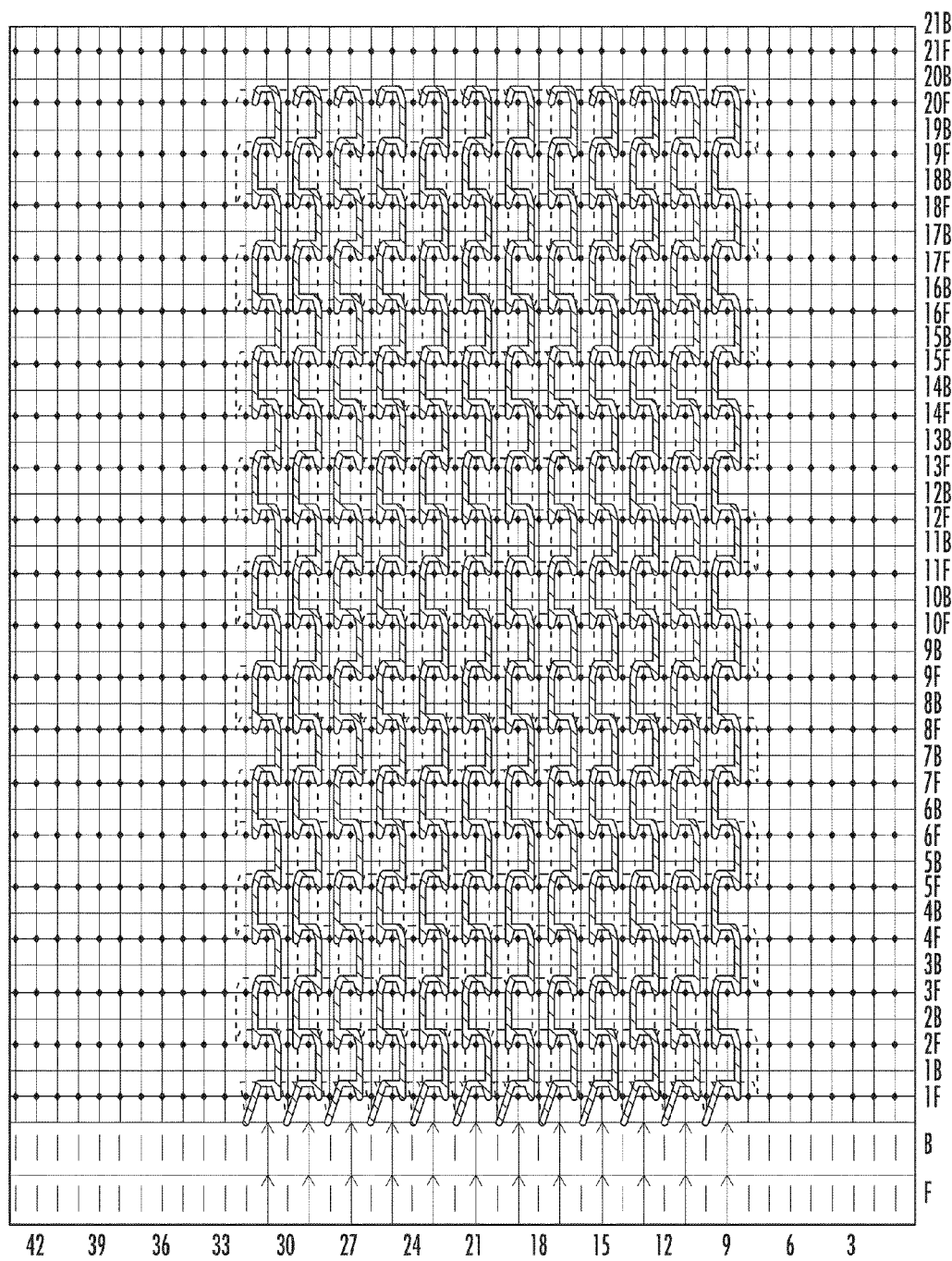
Figure 46B:
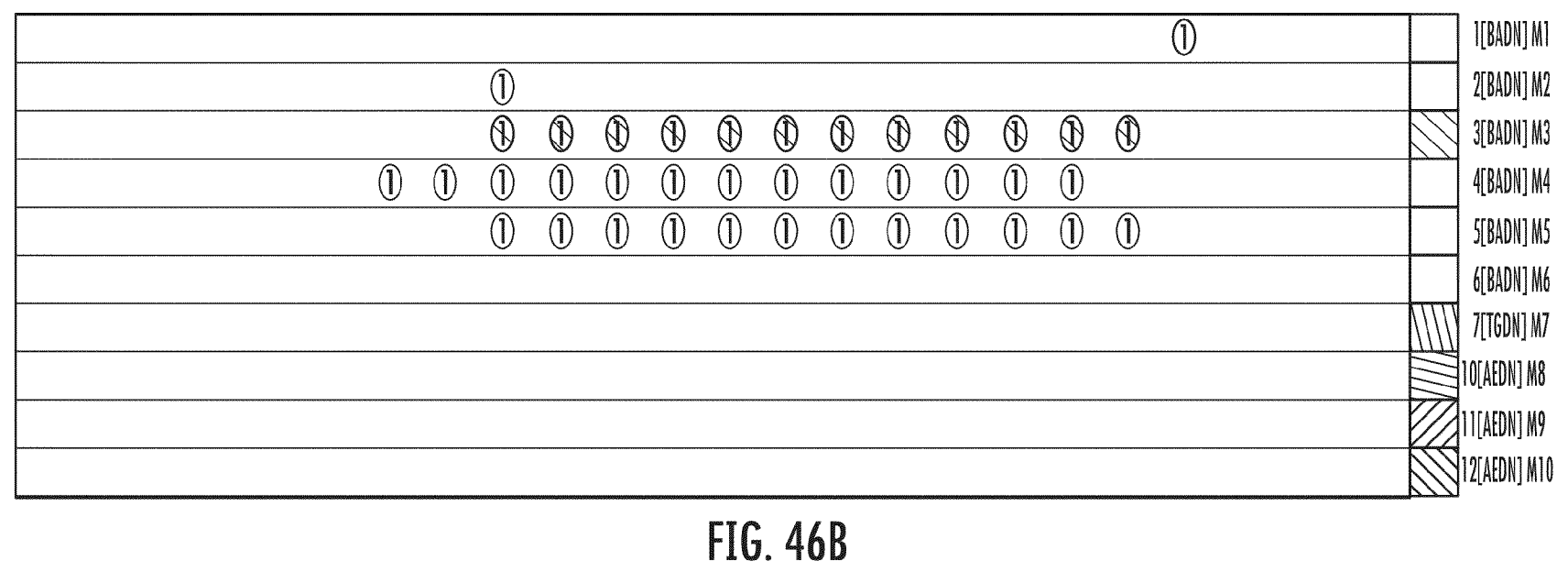
Figure 47A:
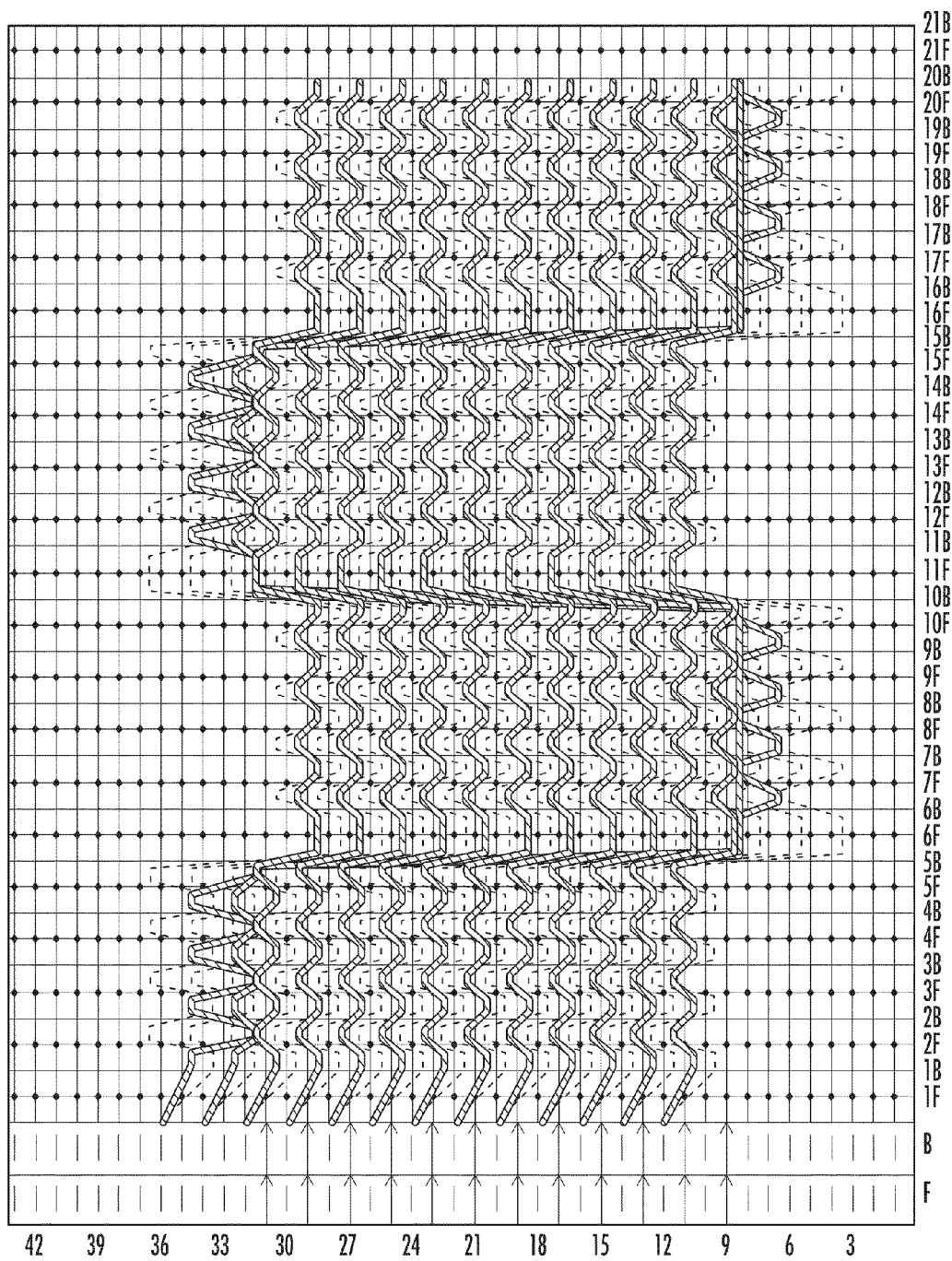
Figure 47B:
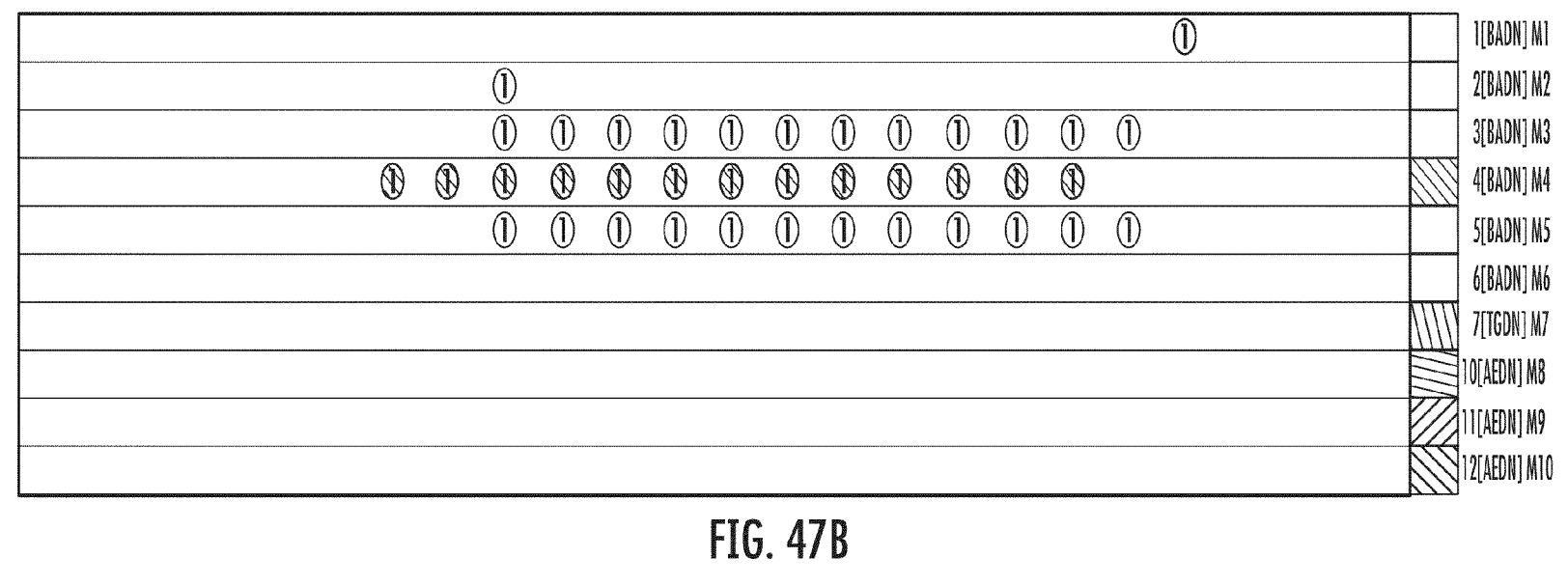
Figure 48A:
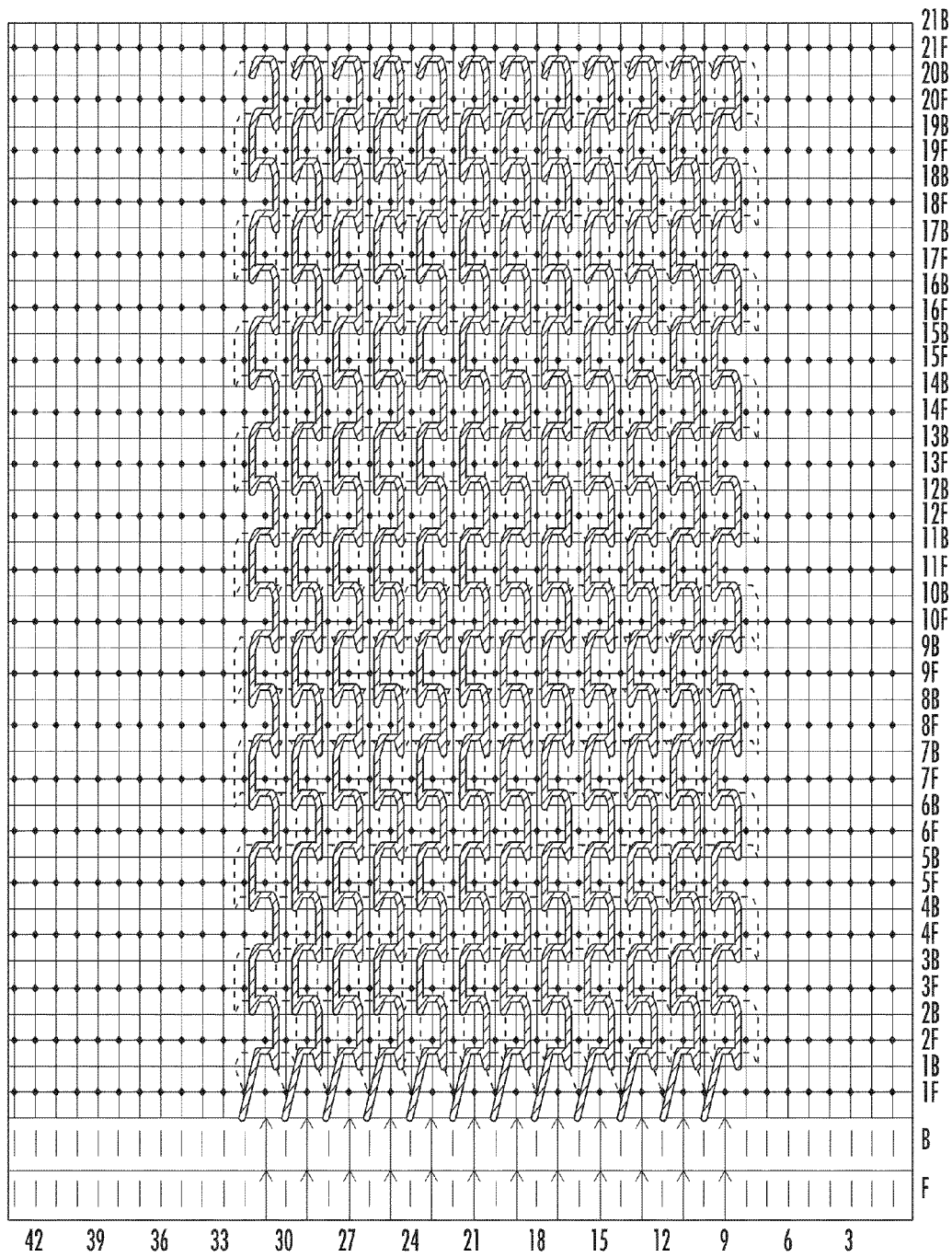
FIGS. 48A and 48B illustrate an example pattern layout for a double needle bed scaffold according to aspects of the present invention from FIG. 42 for ground bar #5.
Figure 48B:
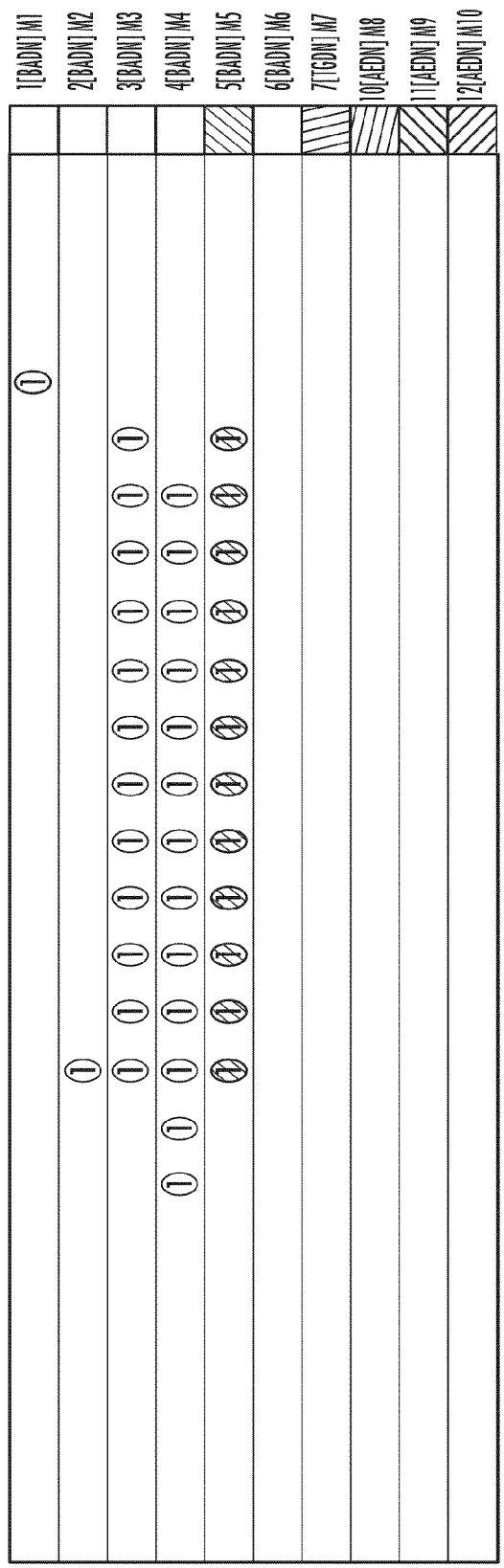

A surgical scaffold device according to aspect of the present invention may be created on a raschel knitting machine such as Comez DNB/EL-800-8B by the use of five movements as shown in pattern layout in FIGS. 43A and 43B: four movements in the wale direction, the vertical direction within the fabric, and one movement in the course direction, the horizontal direction of the fabric. The movements in the wale direction occur on separate needle beds with alternate yarns; loops that occur on every course are staggered within repeat. The yarn follows a repeat pattern of 3/1-1/1-1/3-3/3 for one of the wale direction movement as reported in FIGS. 46A and 46B and 1/1-1/3-3/3-3/1 for the other wale direction movement as reported by FIGS. 48A and 48B. The interlacing of the loops within the fabric allows for one yarn to become under more tension than the other under stress, locking it around the less tensioned yarn; keeping the fabric from unraveling when cut. The other movement in the course direction occurs in every few courses creating the openings in the scaffold and creating the elliptical shape of the scaffold. FIGS. 47A and 47B illustrate an example pattern layout for a double needle bed scaffold according to aspects of the present invention from FIG. 42 for pattern bar #4.

Figure 44A:
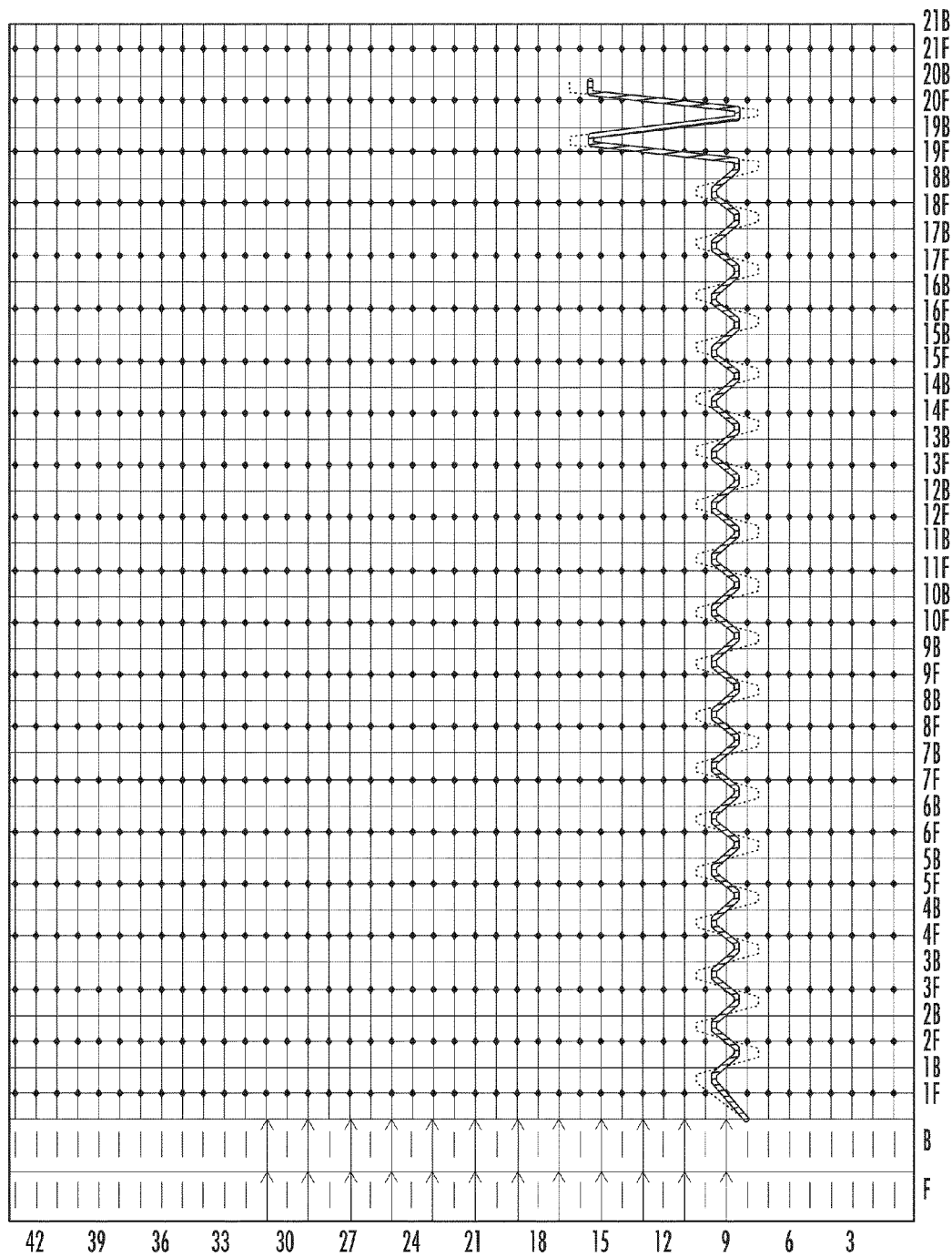
FIGS. 44A and 44B illustrate an example pattern layout for a double needle bed scaffold according to aspects of the present invention from FIG. 42 for elliptical effect bar #1.
Figure 44B:
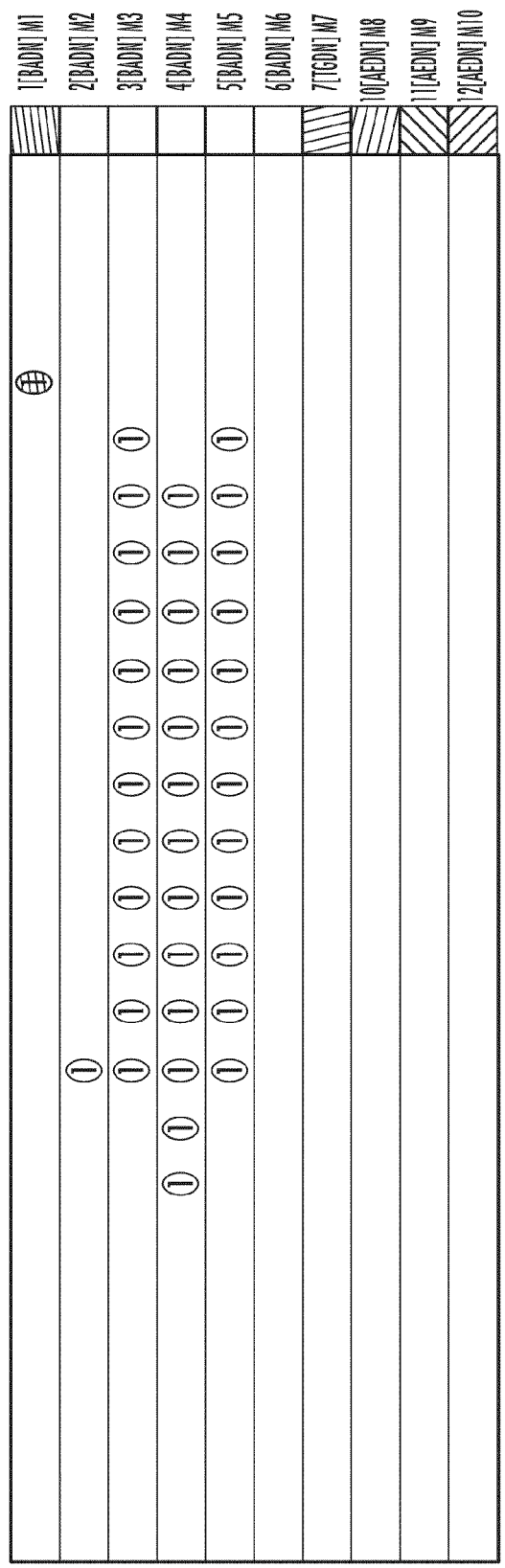
Figure 45A:
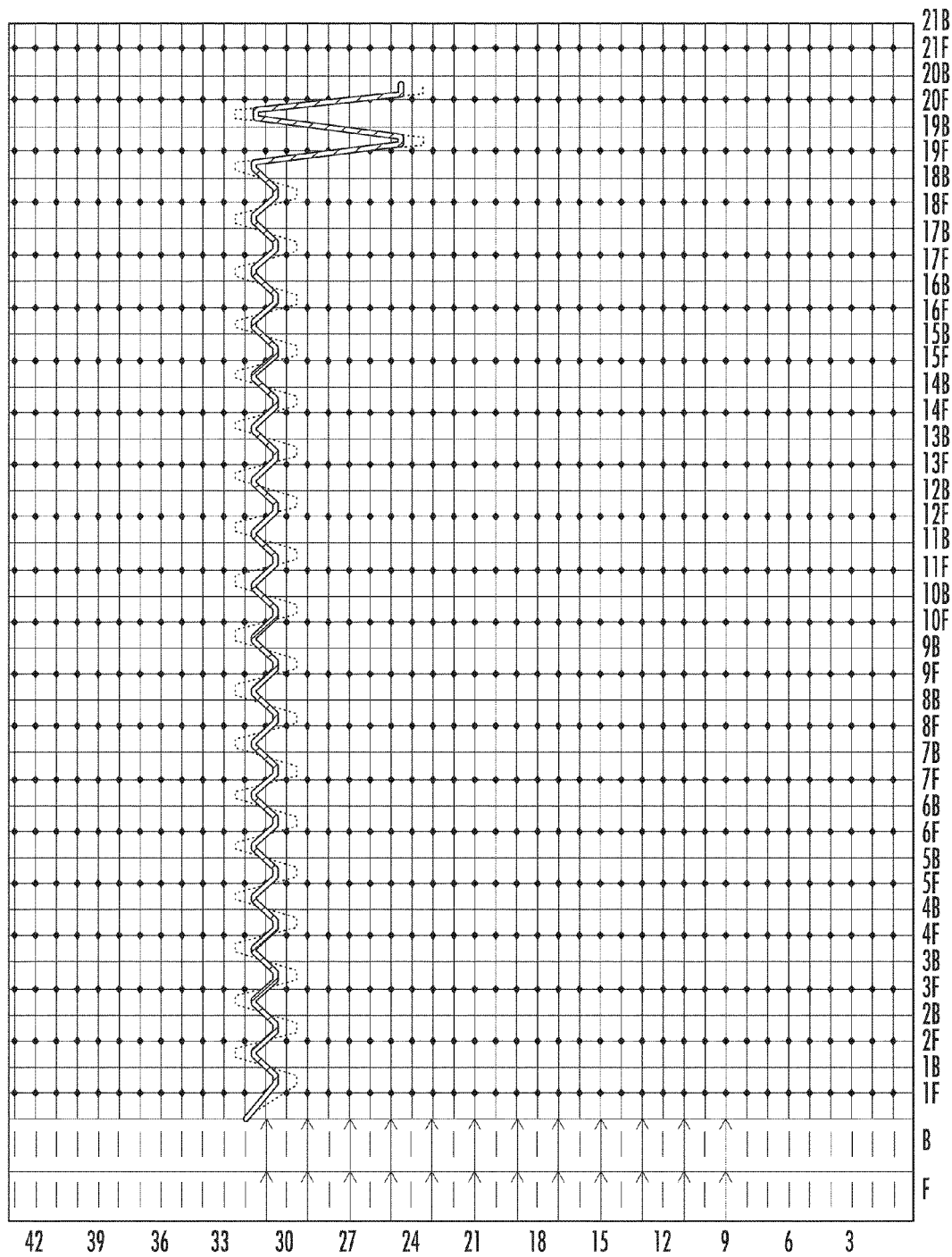
Figure 45B:
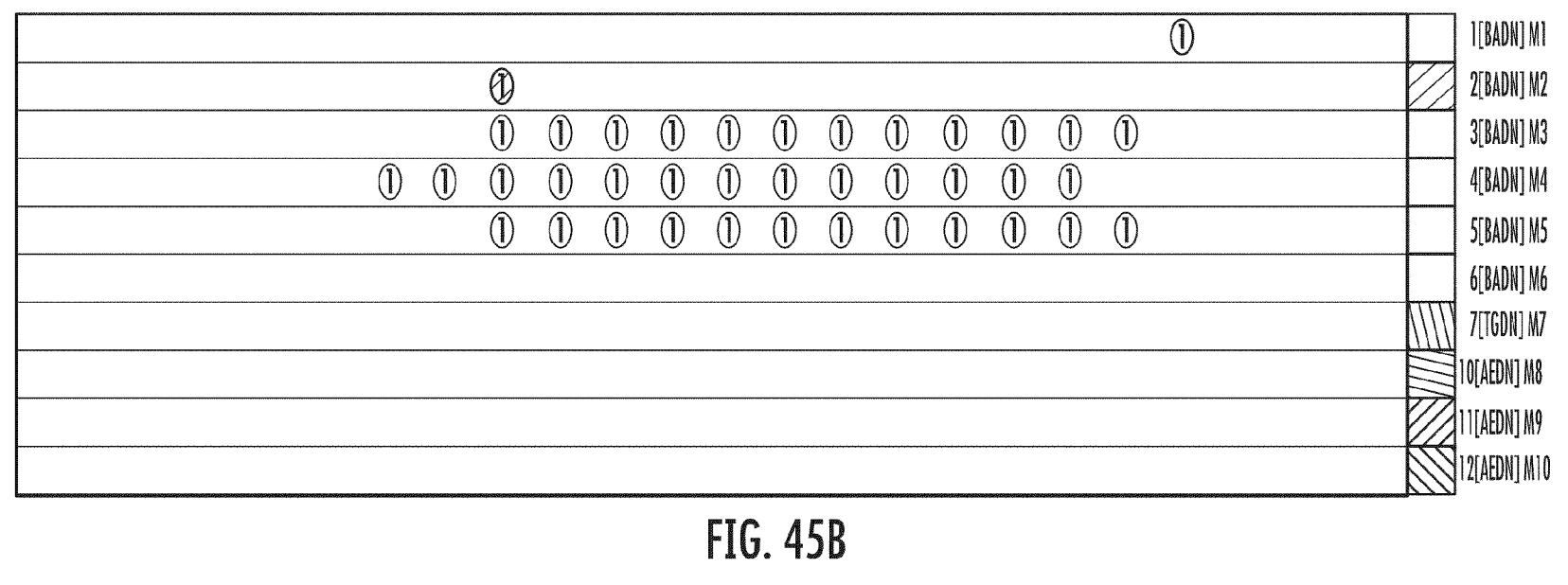
Figure 49:
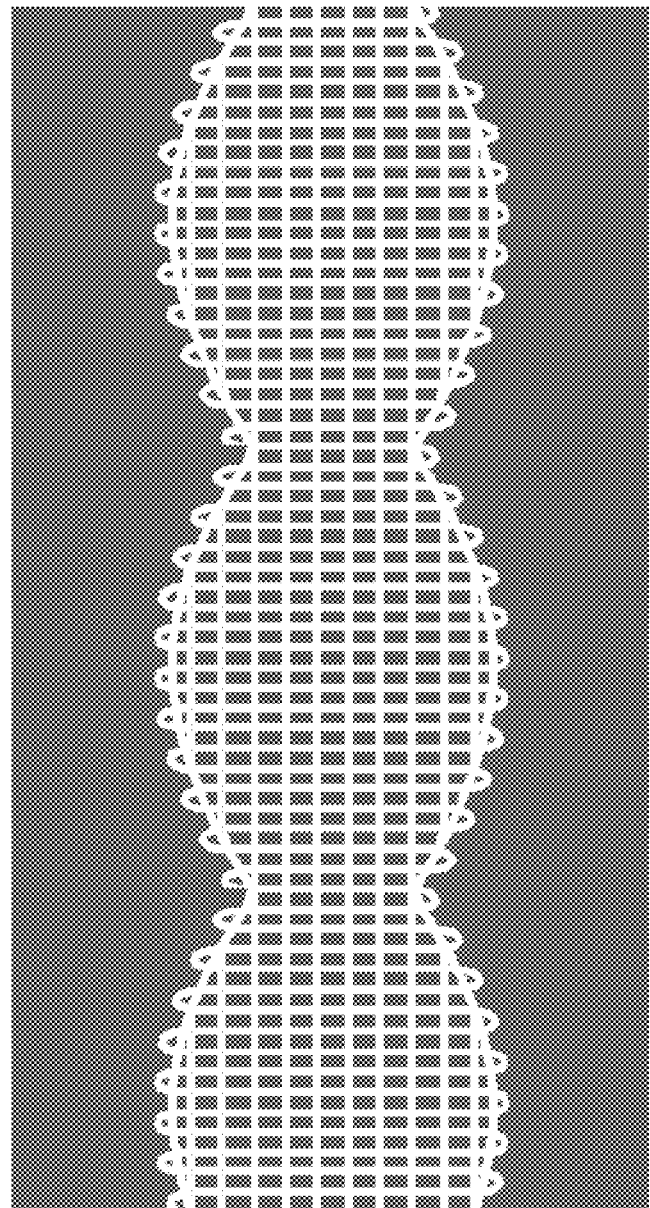
FIG. 49 illustrates an example pattern simulation for a double needle bed scaffold demonstrated in FIG. 43 according to aspects of the present invention.

The yarns creating the openings follow a repeat pattern of 9/9-9/9-7/7-9/9-7/7-9/9-7/7-9/9-7/7-9/9-1/1-1/1-2/2-1/1-2/ 2-1/1-2/2-1/1-2/2-1/1-9/9-9/9-7/7-9/9-7/7-9/9-7/7-9/9-7/7-9/9-1/1-1/1-2/2-1/1-2/2-1/1-2/2-1/1-2/2-1/1. There are two yarns creating the elliptical shape, one on each edge of the scaffold; they follow a repeat pattern of 1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-3/3-1/1-9/9-1/1-9/9 as reported in FIGS. 44A and 44B and 9/9-7/7-9/9-7/7-9/9-7/7-9/9-7/7-9/9-7/7-9/9-7/7-9/9-7/7-9/9-7/ 7-9/9-7/7-9/9-7/7-9/9-7/7-9/9-7/7-9/9-7/7-9/9-7/7-9/9-7/7-9/9-7/7-9/9-7/7-9/9-1/1-9/9-1/1 as reported in FIGS. 45A and 45B. The pattern simulation layout with a repeat from the basic pattern in FIGS. 43A and 43B is rendered with ComezDraw 3 software in FIG. 49 demonstrating the elliptical shape of the fabric. The pattern repeat is developed by repeating ten (10) times from movement 1 to movement 20 of the basic pattern, followed by repeating 1 (1) time from movement 21 to movement 40 of the basic pattern.

In embodiments employing silk yarn, the silk yarn may be twisted from yarn made by 20-22 denier raw silk fibers approximately 40 to 60 μm in diameter. Preferably, raw silk fibers ranging from 10 to 30 denier may be employed; however any fiber diameters that will allow the device to provide sufficient strength to the intended area are acceptable. Advantageously, a constant yarn size may maximize the uniformity of the surgical mesh mechanical properties, e.g. stiffness, elongation, etc., physical and/or biological properties within each region. However, the yarn size may be varied in sections of the surgical mesh in order to achieve different mechanical, physical and/or biological characteristics in the preferred surgical mesh locations. Factors that may influence the size of the yarn include, but are not limited to: ultimate tensile strength (UTS); yield strength, i.e. the point at which the yarn is permanently deformed; percent elongation; fatigue and dynamic laxity (creep); bioresorption rate; and transfer of cell/nutrients into and out of the scaffold.

The knit pattern illustrated in FIGS. 29A and B, FIGS. 36A and B, and FIGS. 43A and B, respectively, may be knitted to any width limited by the knitting machine width and could be knitted with any of the gauges available with the various crochet machines or warp knitting machines. TABLE 12 outlines the fabric widths that may be achieved using different numbers of needles on different gauge machines. It is understood that the dimensions in TABLE 12 are approximate due to the shrink factor which depends on stitch design, stitch density, and yarn size used.

TABLE 12

| Gauge | Needle Count | | Knitting Width (mm) | |
|---|---|---|---|---|
| | From | To | From | To |
| 48 | 2 | 5656 | 0.53 | 2997.68 |
| 24 | 2 | 2826 | 1.06 | 2995.56 |
| 20 | 2 | 2358 | 1.27 | 2994.66 |
| 18 | 2 | 2123 | 1.41 | 2993.43 |
| 16 | 2 | 1882 | 1.59 | 2992.38 |
| 14 | 2 | 1653 | 1.81 | 2991.93 |
| 12 | 2 | 1411 | 2.12 | 2991.32 |
| 10 | 2 | 1177 | 2.54 | 2989.58 |
| 5 | 2 | 586 | 5.08 | 2976.88 |

Figure 50:
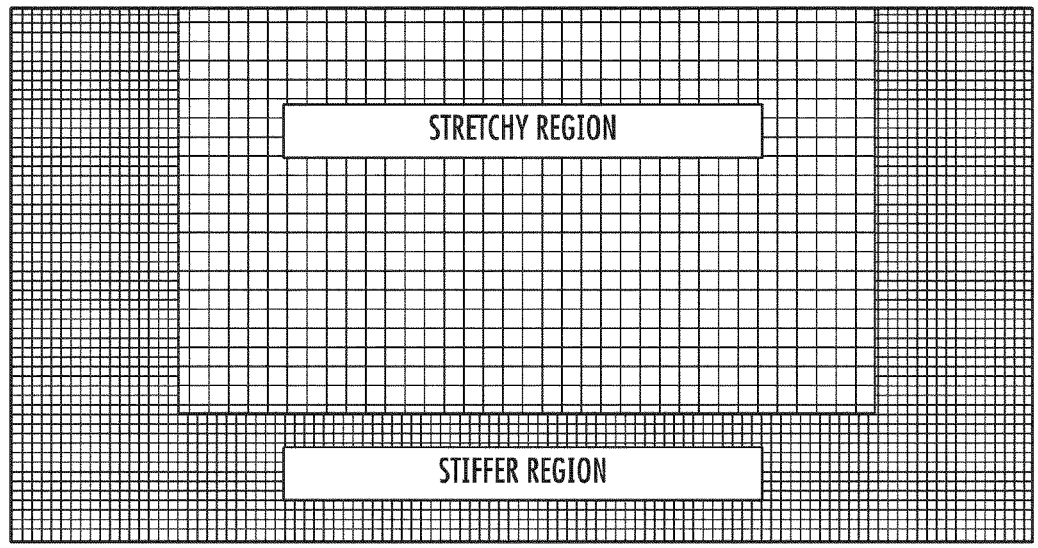
FIG. 50 illustrates another scaffold drawing with two regions: stretchy and stiffer, with the stretchy region being surrounded by the stiffer U-shaped region.

FIG. 50 illustrates another scaffold drawing with two regions: stretchy and stiffer, with the stretchy region being surrounded by the stiffer U-shaped region. As shown in FIG. 50, the scaffold incorporates regions of differing stiffness allowing the scaffold to stretch in particular regions. When used for breast reconstruction, for example, this design may help recreate a more normal breast shape, with an inframammary fold region, a region for medial and lateral reinforcement and a region to allow for breast projection.

Figure 51:
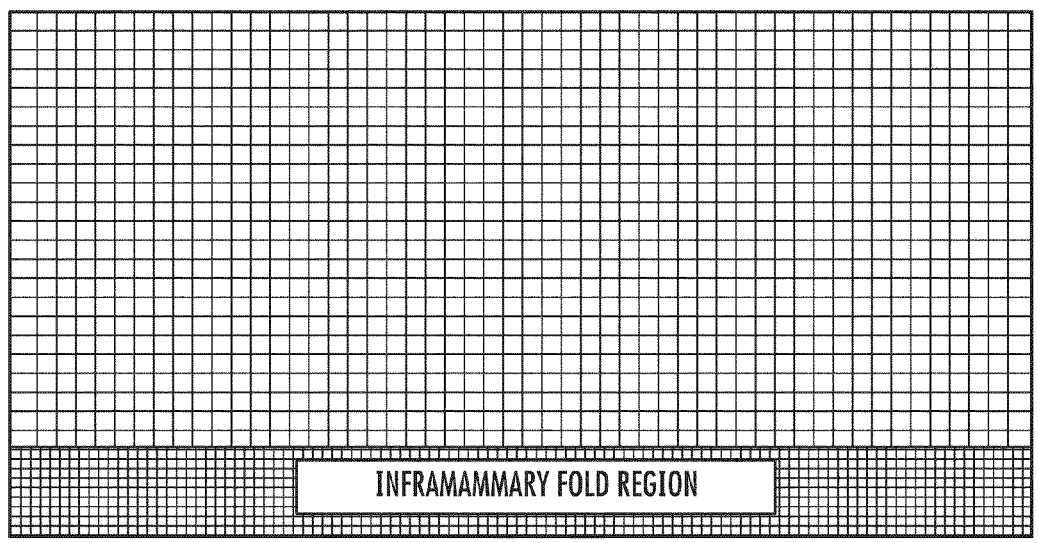
FIG. 51 illustrates another drawing with two regions with a stretchy region and a stiffer region, in the context of an inframammary fold region for use in breast applications.

FIG. 51 illustrates still yet another scaffold drawing with two regions, a stretchy region and a stiffer region, in the context of an inframammary fold region for use in breast applications. As shown in FIG. 51, this scaffold has a region of reinforcement. During breast reconstruction, for example, surgeons strive to recreate the inframammary fold. This scaffold includes a more dense knit region which will help create a more normal looking breast.

Figure 52:
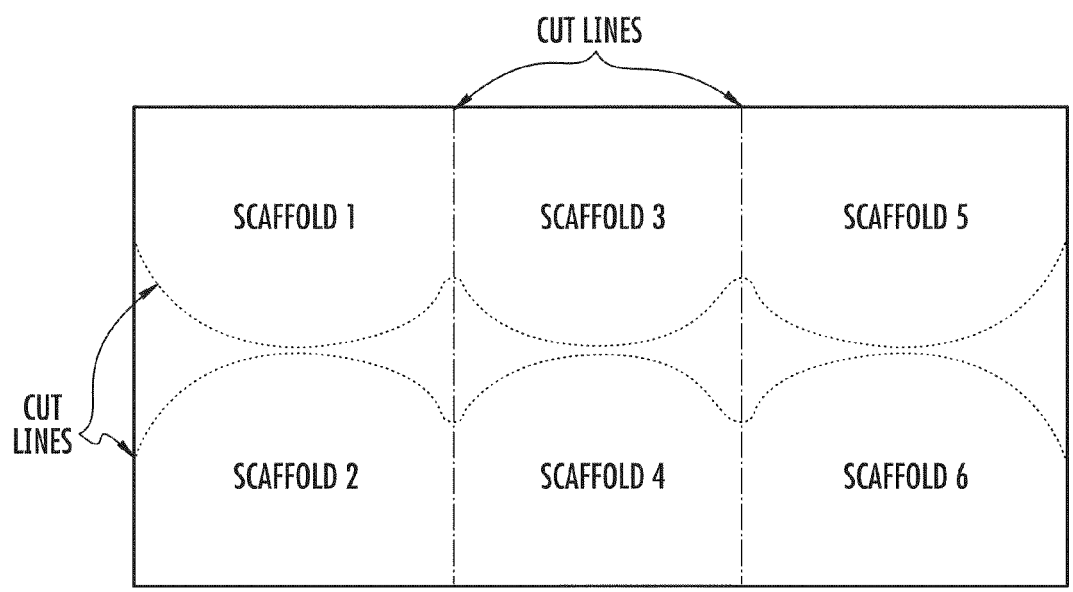
FIG. 52 illustrates the multiple scaffolds with representative cut lines for use in various applications.

FIG. 52 illustrates the multiple scaffolds with representative cut lines for use in various applications. As shown in FIG. 52, two silk scaffolds are knit at one time and when separated create two shaped scaffolds for breast reconstruction, for example. The shaped design may allow surgeons to create a more normal looking breast. The knit construction as shown produces two devices per unit length.

A scaffold with isotropic stretch, particularly more isotropic stretch in the fabric width and fabric formation direction, reduces the risk of a user placing the scaffold in the wrong direction, thus making the scaffold safer and easier to use.

Embodiments of the scaffold device according to the present invention may be knitted on a fine gauge crochet knitting machine. A non-limiting list of crochet machines capable of manufacturing the surgical mesh according to aspects of the present invention are provided by: Changde Textile Machinery Co., Ltd.; Gomez; China Textile Machinery Co., Ltd.; Huibang Machine; Jakkob Muller AG; Jingwei Textile Machinery Co., Ltd.; Zhejiang Jingyi Textile Machinery Co., Ltd.; Dongguan Kyang the Delicate Machine Co., Ltd.; Karl Mayer; Sanfang Machine; Sino Techfull; Suzhou Huilong Textile Machinery Co., Ltd.; Taiwan Giu Chun Ind. Co., Ltd.; Zhangjiagang Victor Textile; Liba; Lucas; Muller Frick; and Texma.

Embodiments of the scaffold device according to the present invention may be knitted on a fine gauge warp knitting machine. A non-limiting list of warp knitting machines capable of manufacturing the surgical mesh according to aspects of the present invention are provided by: Comez; Diba; Jingwei Textile Machinery; Liba; Lucas; Karl Mayer; Muller Frick; Runyuan Warp Knitting; Taiwan Giu Chun Ind.; Fujian Xingang Textile Machinery; and Yuejian Group.

Embodiments of the scaffold device according to the present invention may be knitted on a fine gauge flat bed knitting machine. A non-limiting list of flat bed machines capable of manufacturing the surgical mesh according to aspects of the present invention are provided by: Around Star; Boosan; Cixing Textile Machine; Fengshen; Flying Tiger; Machinery; Fujian Hongqi; G & P Gorteks; Jinlong; JP; Jy Leh; Kauo Heng Co., Ltd.; Matsuya; Nan Sing Machinery Limited; Nantong Sansi Instrument; Shima Seiki; Nantong Tianyuan; and Ningbo Yuren Knitting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of and/or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A biocompatible, bioresorbable, knitted surgical scaffold for soft tissue reconstruction or repair, comprising:
   (a) a first set of yarns and a second set of yarns, the first set of yarns interlacing with the second set of yarns to define nodes, the first set of yarns and the second set of yarns alternately applied in a wale direction to form staggered loops, wherein the alternating application of the first set of yarns and the second set of yarns causes the first set of yarns to have different tensions relative to the second set of yarns at the nodes, and the difference in tension substantially preventing the knitted scaffold from unraveling at the nodes; and
   (b) regions of varying stretch to contour to a soft tissue shape for replacement or repair, the regions of varying stretch comprising a stretchy region and a U-shaped stiffer region, the stretchy region being surrounded by the U-shaped stiffer region,
   wherein the scaffold is bioresorbable and consists essentially of sericin-depleted silk.

2. The biocompatible, knitted surgical scaffold according to claim 1, wherein the scaffold is porous to allow tissue in-growth.

3. The biocompatible, knitted surgical scaffold according to claim 1, wherein the scaffold degrades at a rate which allows for a smooth transfer of mechanical properties to new tissue from the scaffold.

4. The biocompatible, knitted surgical scaffold according to claim 1, wherein surgical scaffold is used for soft tissue reconstruction or repair in a breast reconstruction, mastopexy, breast augmentation revision, breast augmentation support, standard breast augmentation, chest wall repair, organ support, body contouring, abdominoplasty, facial reconstruction, hernia repair, or pelvic floor repair.

5. A knitted biocompatible, bioresorbable surgical scaffold consisting essentially of a first set of yarns and a second set of yarns, the first set of yarns interlacing with the second set of yarns to define nodes, the first set of yarns and the second set of yarns alternately applied in a wale direction to form staggered loops, wherein the alternating application of the first set of yarns and the second set of yarns causes the first set of yarns to have different tensions relative to the second set of yarns at the nodes, and the difference in tension substantially preventing the knitted scaffold from unraveling at the nodes, and, wherein the scaffold has at least two regions parallel to each other that differ in mechanical properties comprised of a stretchy region and a stiffer region, and
   wherein the scaffold is bioresorbable and consists essentially of sericin-depleted silk.

6. The knitted biocompatible surgical scaffold according to claim 5, wherein the stretchy region of the scaffold has lower stiffness and higher flexibility as compared to the stiffer region.

7. The knitted biocompatible surgical scaffold according to claim 6, wherein the stretchy region of the scaffold provides projection of a breast while offering shapeability.

8. The knitted biocompatible surgical scaffold according to claim 5, wherein the stiffer region of the scaffold has higher stiffness and lower flexibility as compared to the stretchy region.

9. The knitted biocompatible surgical scaffold according to claim 8, wherein the stiffer region provides definition of an inframammary fold with initial support for a tissue expander.

10. The knitted biocompatible surgical scaffold according to claim 5, wherein the stiffer region provides support for suture anchoring.

* * * * *